(12) United States Patent
Cheung et al.

(10) Patent No.: US 12,681,006 B2
(45) Date of Patent: Jul. 14, 2026

(54) METHODS OF GENERATING HUMAN ENDOMETRIAL STROMAL FIBROBLASTS AND THREE-DIMENSIONAL MULTI-LAYERED HUMAN ENDOMETRIAL TISSUE COMPOSITIONS

(71) Applicant: Northwestern University, Evanston, IL (US)

(72) Inventors: Virginia Chu Cheung, Evanston, IL (US); John Kessler, Evanston, IL (US); Chian-Yu Peng, Evanston, IL (US)

(73) Assignee: Northwestern University, Evanston, IL (US)

( * ) Notice: Subject to any disclaimer, the term of this patent is extended or adjusted under 35 U.S.C. 154(b) by 695 days.

(21) Appl. No.: 17/734,007

(22) Filed: Apr. 30, 2022

(65) Prior Publication Data

US 2022/0349874 A1 Nov. 3, 2022

Related U.S. Application Data

(60) Provisional application No. 63/201,494, filed on Apr. 30, 2021.

(51) Int. Cl.
*G01N 33/50* (2006.01)
*C12N 5/071* (2010.01)

(52) U.S. Cl.
CPC ....... *G01N 33/5005* (2013.01); *C12N 5/0682* (2013.01); *C12N 5/0697* (2013.01); *C12N 2501/155* (2013.01); *C12N 2501/392* (2013.01); *C12N 2501/415* (2013.01); *C12N 2503/04* (2013.01); *C12N 2506/45* (2013.01); *C12N 2513/00* (2013.01); *C12N 2533/90* (2013.01)

(58) Field of Classification Search
None
See application file for complete search history.

(56) References Cited

PUBLICATIONS

Díez, M., Przyborski, S., del Cerro, A. et al. Generation of a novel three-dimensional scaffold-based model of the bovine endometrium. Vet Res Commun 47, 1721-1733 (2023). https://doi.org/10.1007/s11259-023-10130-0 (Year: 2023).*
Cousins FL, Pandoy R, Jin S, Gargett CE. The Elusive Endometrial Epithelial Stem/Progenitor Cells. Front Cell Dev Biol. Apr. 9, 2021;9:640319. doi: 10.3389/fcell.2021.640319. PMID: 33898428; PMCID: PMC8063057. (Year: 2021).*
Igarashi TM, Bruner-Tran KL, Yeaman GR, Lessey BA, Edwards DP, Eisenberg E, Osteen KG. Reduced expression of progesterone receptor-B in the endometrium of women with endometriosis and in cocultures of endometrial cells exposed to 2,3,7,8-tetrachlorodibenzo-p-dioxin. Fertil Steril. Jul. 2005; (Year: 2005).*

(Continued)

*Primary Examiner* — Evelyn Y Pyla
*Assistant Examiner* — Jagamya Nmn Vijayaraghavan
(74) *Attorney, Agent, or Firm* — Quarles & Brady LLP

(57) ABSTRACT

Disclosed herein are methods for obtaining endometrial stromal fibroblast cells from pluripotent stem cells, such as induced pluripotent stem cells. The present disclosure also provides methods of obtaining a three-dimensional, multi-layered endometrial tissue composition. Methods of using the cells and tissue compositions in drug screening and therapeutic applications are also provided.

6 Claims, 38 Drawing Sheets
(37 of 38 Drawing Sheet(s) Filed in Color)
Specification includes a Sequence Listing.

(56)         References Cited

PUBLICATIONS

Suzuki, K., Koyanagi-Aoi, M., Uehara, K. et al. Directed differentiation of human induced pluripotent stem cells into mature stratified bladder urothelium. Sci Rep 9, 10506 (2019). https://doi.org/10.1038/s41598-019-46848-8 (Year: 2019).*

Yoda K, et al Optimization of the treatment conditions with glycogen synthase kinase-3 inhibitor towards enhancing the proliferation of human induced pluripotent stem cells while maintaining an undifferentiated state under feeder-free conditions. J Biosci Bioeng. Mar. 2019 (Year: 2019).*

Abbas, Y., Brunel, L. G., Hollinshead, M. S., Fernando, R. C., Gardner, L., Duncan, I., Moffett, A., Best, S., Turco, M. Y., Burton, G. J. & Cameron, R. E. 2020. Generation of a three-dimensional collagen scaffold-based model of the human endometrium. Interface Focus, 10, 20190079.

Aghajanova, L., Hamilton, A., Kwintkiewicz, J., VO, K. C. & Giudice, L. C. 2009. Steroidogenic enzyme and key decidualization marker dysregulation in endometrial stromal cells from women with versus without endometriosis. Biol Reprod, 80, 105-14.

Armstrong, G. M., Maybin, J. A., Murray, A. A., Nicol, M., Walker, C., Saunders, P. T. K., Rossi, A. G. & Critchley, H. O. D. 2017. Endometrial apoptosis and neutrophil infiltration during menstruation exhibits spatial and temporal dynamics that are recapitulated in a mouse model. Sci Rep, 7, 17416.

Ashburner, M., Ball, C. A., Blake, J. A., Botstein, D., Butler, H., Cherry, J. M., Davis, A. P., Dolinski, K., Dwight, S. S., Eppig, J. T., Harris, M. A., Hill, D. P., Issel-Tarver, L., Kasarskis, A., Lewis, S., Matese, J. C., Richardson, J. E., Ringwald, M., Rubin, G. M. & Sherlock, G. 2000. Gene ontology: tool for the unification of biology. The Gene Ontology Consortium. Nat Genet, 25, 25-9.

Boretto, M., Cox, B., Noben, M., Hendriks, N., Fassbender, A., Roose, H., Amant, F., Timmerman, D., Tomassetti, C., Vanhie, A., Meuleman, C., Ferrante, M. & Vankelecom, H. 2017. Development of organoids from mouse and human endometrium showing endometrial epithelium physiology and long-term expandability. Development, 144, 1775-1786.

Chen, E. Y., Tan, C. M., Kou, Y., Duan, Q., Wang, Z., Meirelles, G. V., Clark, N. R. & Ma'ayan, A. 2013. Enrichr: interactive and collaborative HTML5 gene list enrichment analysis tool. BMC Bioinformatics, 14, 128.

Consortium, E. P. 2011. A user's guide to the encyclopedia of DNA elements (ENCODE). PLoS Biol, 9, e1001046.

Coppock, H. A., White, A., Aplin, J. D. & Westwood, M. 2004. Matrix metalloprotease-3 and -9 proteolyze Insulin-like growth factor-binding protein-1. Biol Reprod, 71, 438-43.

Cunha, G. R. 1976. Stromal induction and specification of morphogenesis and cytodifferentiation of the epithelia of the Mullerian ducts and urogenital sinus during development of the uterus and vagina in mice. J Exp Zool, 196, 361-70.

Deane, J. A., Cousins, F. L. & Gargett, C. E. 2017. Endometrial organoids: in vitro models for endometrial research and personalized medicine. Biol Reprod, 97, 781-783.

Du, H. & Taylor, H. S. 2015. The Role of Hox Genes in Female Reproductive Tract Development, Adult Function, and Fertility. Cold Spring Harb Perspect Med, 6, a023002.

Egashira, M. & Hirota, Y. 2013. Uterine receptivity and embryo-uterine interactions in embryo implantation: lessons from mice. Reprod Med Biol, 12, 127-132.

Fitzgerald, H. C., Dhakal, P., Behura, S. K., Schust, D. J. & Spencer, T. E. 2019. Selfrenewing endometrial epithelial organoids of the human uterus. Proc Natl Acad Sci U S A, 116, 23132-23142.

Fullerton, P. T., Jr., Monsivais, D., Kommagani, R. & Matzuk, M. M. 2017. Follistatin is critical for mouse uterine receptivity and decidualization. Proc Natl Acad Sci U S A, 114, E4772-E4781.

Ganeff, C., Chatel, G., Munaut, C., Frankenne, F., Foidart, J. M. & Winkler, R. 2009. The IGF system in In-vitro human decidualization. Mol Hum Reprod, 15, 27-38.

Gellersen, B. & Brosens, J. J. 2014. Cyclic decidualization of the human endometrium in reproductive health and failure. Endocr Rev, 35, 851-905.

Goffin, F., Munaut, C., Frankenne, F., Perrier D'hauterive, S., Beliard, A., Fridman, V., Nervo, P., Colige, A. & Foidart, J. M. 2003. Expression pattern of metalloproteinases and tissue inhibitors of matrix- metalloproteinases in cycling human endometrium. Biol Reprod, 69, 976-84.

Gurung, S., Williams, S., Deane, J. A., Werkmeister, J. A. & Gargett, C. E. 2018. The Transcriptome of Human Endometrial Mesenchymal Stem Cells Under TGFbetaR Inhibition Reveals Improved Potential for Cell-Based Therapies. Front Cell Dev Biol, 6, 164.

Haider, S., Gamperl, M., Burkard, T. R., Kunihs, V., Kaindl, U., Junttila, S., Fiala, C., Schmidt, K., Mendjan, S., Knofler, M. & Latos, P. A. 2019. Estrogen signaling drives ciliogenesis in human endometrial organoids. Endocrinology, 160(10), 2282-2297.

Hallman, M., Haapalainen, A., Huusko, J. M., Karjalainen, M. K., Zhang, G., Muglia, L. J. & Ramet, M. 2019. Spontaneous premature birth as a target of genomic research. Pediatr Res, 85, 422-431.

Hantak, A. M., Bagchi, I. C. & Bagchi, M. K. 2014. Role of uterine stromal-epithelial crosstalk in embryo Implantation. Int J Dev Biol, 58, 139-46.

Hemberger, M., Hanna, C. W. & Dean, W. 2020. Mechanisms of early placental development in mouse and humans. Nat Rev Genet, 21, 27-43.

Huang, R., Grishagin, I., Wang, Y., Zhao, T., Greene, J., Obenauer, J. C., Ngan, D., Nguyen, D. T., Guha, R., Jadhav, A., Southall, N., Simeonov, A. & Austin, C. P. 2019. The NCATS BioPlanet—An Integrated Platform for Exploring the Universe of Cellular Signaling Pathways for Toxicology, Systems Biology, and Chemical Genomics. Front Pharmacol, 10, 445.

Ing, N. H. & Tornesi, M. B. 1997. Estradiol up-regulates estrogen receptor and progesterone receptor gene expression in specific ovine uterine cells. Biol Reprod, 56, 1205-15.

Jin, S. 2019. Bipotent stem cells support the cyclical regeneration of endometrial epithelium of the murine uterus. Proc Natl Acad Sci U S A, 116, 6848-6857.

Kin, K., Nnamani, M. C., Lynch, V. J., Michaelides, E. & Wagner, G. P. 2015. Cell-type phylogenetics and the origin of endometrial stromal cells. Cell Rep, 10, 1398-409.

Kuleshov, M. V., Jones, M. R., Rouillard, A. D., Fernandez, N. F., Duan, Q., Wang, Z., Koplev, S., Jenkins, S. L., Jagodnik, K. M., Lachmann, A., Mcdermott, M. G., Monteiro, C. D., Gundersen, G. W. & Ma'ayan, A. 2016. Enrichr: a comprehensive gene set enrichment analysis web server 2016 update. Nucleic Acids Res, 44, W90-7.

Lachmann, A., Xu, H., Krishnan, J., Berger, S. I., Mazloom, A. R. & Ma'ayan, A. 2010. ChEA: transcription factor regulation inferred from integrating genome-wide ChIP-X experiments. Bioinformatics, 26, 2438-44.

Lee, K. Y., Jeong, J. W., Wang, J., Ma, L., Martin, J. F., Tsai, S. Y., Lydon, J. P. & Demayo, F. J. 2007. Bmp2 is critical for the murine uterine decidual response. Mol Cell Biol, 27, 5468-78.

Leek, J. T. 2014. svaseq: removing batch effects and other unwanted noise from sequencing data. Nucleic Acids Res, 42.

Li, Q., Kannan, A., Das, A., Demayo, F. J., Hornsby, P. J., Young, S. L., Taylor, R. N., Bagchi, M. K. & Bagchi, I. C. 2013. WNT4 acts downstream of BMP2 and functions via beta-catenin signaling pathway to regulate human endometrial stromal cell differentiation. Endocrinology, 154, 446-57.

Love, M. I., Huber, W. & Anders, S. 2014. Moderated estimation of fold change and dispersion for RNA-seq data with DESeq2. Genome Biol, 15, 550.

Male, V., Gardner, L. & Moffett, A. 2012. Isolation of cells from the feto-maternal interface. Curr Protoc Immunol, Chapter 7, Unit 7 40 1-11.

Marinic, M. & Lynch, V. J. 2019. Derivation of endometrial gland organoids from term postpartum placenta. bioRxiv 753780.

Marinic, M., Rana, S. & Lynch, V. J. 2020. Derivation of endometrial gland organoids from term placenta. Placenta, 101, 75-79.

Masuda, H., Anwar, S. S., Buhring, H. J., Rao, J. R. & Gargett, C. E. 2012. A novel marker of human endometrial mesenchymal stem-like cells. Cell Transplant, 21, 2201-14.

(56) References Cited

PUBLICATIONS

Mclean, M., Davis, A. J. & Reindollar, R. H. 2000. Abnormalities of Female Pubertal Development. In: Endotext. South Dartmouth (MA).

Feingold, K. R., Anawalt, B., Boyce, A., Chrousos, G., Dungan, K., Grossman, A., Hershman, J. M., Kaltsas, G., Koch, C., Kopp, P., Korbonits, M., Mclachlan, R., Morley, J. E., New, M., Perreault, L., Purnell, J., Rebar, R., Singer, F., Trence, D. L., Vinik, A. & Wilson, D. P. (eds.). 2000. Lipoprotein (a) in Youth. Endotext, South Dartmouth (MA).

Miyazaki, K., Dyson, M. T., Coon, V. J., Furukawa, Y., Yilmaz, B. D., Maruyama, T. & Bulun, S. E. 2018. Generation of Progesterone-Responsive Endometrial Stromal Fibroblasts from Human Induced Pluripotent Stem Cells: Role of the WNT/CTNNB1 Pathway. Stem Cell Reports, 11, 1136-1155.

Morizane, R., Lam, A. Q., Freedman, B. S., Kishi, S., Valerius, M. T. & Bonventre, J. V. 2015. Nephron organoids derived from human pluripotent stem cells model kidney development and injury. Nat Biotechnol, 33, 1193-200.

Muruganandan, S., Fan, X., Dhal, S. & Nayak, N. R. 2020. Development of a 3D Tissue Slice Culture Model for the Study of Human Endometrial Repair and Regeneration. Biomolecules, 10.

Nawaz, G. & Rogol, A. D. 2020. Amenorrhea. StatPearls. Treasure Island (FL).

Patro, R., Duggal, G., Love, M. I., Irizarry, R. A. & Kingsford, C. 2017. Salmon provides fast and bias-aware quantification of transcript expression. Nat Methods, 14, 417-419.

Saatcioglu, H. D., Kano, M., Horn, H., Zhang, L., Samore, W., Nagykery, N., Meinsohn, M. C., Hyun, M., Suliman, R., Poulo, J., Hsu, J., Sacha, C., Wang, D., Gao, G., Lage, K., Oliva, E., Morris Sabatini, M. E., Donahoe, P. K. & Pepin, D. 2019. Single-cell sequencing of neonatal uterus reveals an Misr2+ endometrial progenitor indispensable for fertility. Elife, 8.

Sakabe, N., Aneas, 1., Knoblauch, N., Sobreira, D. R., Clark, N., Paz, C., Horth, C., Ziffra, R., Kaur, 4., Liu, X., Anderson, R., Morrison, J., Cheung, V. C., Grotegut, C., Reddy, T. E., Jacobsson, B., Hallman, M., Teramo, K., Murtha, A., Kessler, J., Grobman, W., Zhang, G., Muglia, L. J., Rana, S., Lynch, V. J., Crawford, G. E., Ober, C., He, X. & Nobrega, M. A. 2020. Transcriptome and regulatory maps pf decidua-derived stromal cells inform gene discovery in preterm birth. bioRxiv, 2020.04.06.017079.

Schuring, A. N., Schulte, N., Kelsch, R., Ropke, A., Kiesel, L. & Gotte, M. 2011. Characterization of endometrial mesenchymal stem-like cells obtained by endometrial biopsy during routine diagnostics. Fertil Steril, 95, 423-6.

Schwab, K. E. & Gargett, C. E. 2007. Co-expression of two perivascular cell markers isolates mesenchymal stem- ike cells from human endometrium. Hum Reprod, 22, 2903-11.

Scotti, S., Regidor, P. A., Schindler, A. E. & Winterhager, E. 2000. Reduced proliferation and cell adhesion in endometriosis. Mol Hum Reprod, 6, 610-7.

Su, R. W., Strug, M. R., Jeong, J. W., Miele, L. & Fazleabas, A. T. 2016. Aberrant activation of canonical Notch1 signaling in the mouse uterus decreases progesterone receptor by hypermethylation and leads to infertility. Proc Natl Acad Sci U S A, 113, 2300-5.

Suryawanshi, H., Morozov, P., Straus, A., Sahasrabudhe, N., Max, K. E. A., Garzia, A., Kustagi, M., Tuschl, T. & Williams, Z. 2018. A single-cell survey of the human firsttrimester placenta and decidua. Sci Adv, 4, eaau4788.

Takasato, M., Er, P. X., Becroft, M., Vanslambrouck, J. M., Stanley, E. G., Elefanty, A. G. & Little, M. H. 2014. Directing human embryonic stem cell differentiation towards a renal lineage generates a self-organizing kidney. Nat Cell Biol, 16, 118-26.

Turco, M. Y., Gardner, L., Hughes, J., Cindrova-Davies, T., Gomez, M. J., Farrell, L., Hollinshead, M., Marsh, S. G. E., Brosens, J. J., Critchley, H. O., Simons, B. D., Hemberger, M., Koo, B. K., Moffett, A. & Burton, G. J. 2017. Long-term, hormoneresponsive organoid cultures of human endometrium in a chemically defined medium. Nat Cell Biol, 19, 568-577.

Van Sinderen, M., Cuman, C., Gamage, T., Rainczuk, K., Osianlis, T., Rombauts, L. & Dimitriadis, E. 2014. Localisation of the Notch family in the human endometrium of fertile and infertile women. J Mol Histol, 45, 697-706.

Vaskivuo, T. E., Stenback, F., Karhumaa, P., Risteli, J., Dunkel, L. & Tapanainen, J. S. 2000. Apoptosis and apoptosis-related proteins in human endometrium. Mol Cell Endocrinol, 165, 75-83.

Vasquez, Y. M., Wang, X., Wetendorf, M., Franco, H. L., Mo, Q., Wang, T., Lanz, R. B., Young, S. L., Lessey, B. A., Spencer, T. E., Lydon, J. P. & Demayo, F. J. 2018. FOXO1 regulates uterine epithelial integrity and progesterone receptor expression critical for embryo implantation. PLoS Genet, 14, e1007787.

Vassilev, V., Pretto, C. M., Cornet, P. B., Delvaux, D., Eeckhout, Y., Courtoy, P. J., Marbaix, E. & Henriet, P. 2005. Response of matrix metalloproteinases and tissue inhibitors of metalloproteinases messenger ibonucleic acids to ovarian steroids in human endometrial explants mimics their gene- and phase-specific differential control in vivo. J Clin Endocrinol Metab, 90, 5848-57.

Vento-Tormo, R., et al. 2018. Single-cell reconstruction of the early maternal-fetal interface in humans. Nature, 563, 347-353.

Wang, W., Vilella, F., Moreno, I., Pan, W., Quake, S. & Simon, C. 2018. Single Cell Rnaseq Provides a Molecular and Cellular Cartography of Changes to the Human Endometrium through the Menstrual Cycle. Fertility and Sterility, 110, E2-E2.

Wiwatpanit, T., Murphy, A. R., Lu, Z., Urbanek, M., Burdette, J. E., Woodruff, T. K. & Kim, J. J. 2020. Scaffold-Free Endometrial Organoids Respond to Excess Androgens Associated With Polycystic Ovarian Syndrome. J Clin Endocrinol Metab, 105.

Yin, M., Zhou, H. J., Lin, C., Long, L., Yang, X., Zhang, H., Taylor, H. & Min, W. 2019. CD34(+)KLF4(+) Stromal Stem Cells Contribute to Endometrial Regeneration and Repair. Cell Rep, 27, 2709-2724 e3.

Yucer, N., Holzapfel, M., Jenkins Vogel, T., Lenaeus, L., Ornelas, L., Laury, A., Sareen, D., Barrett, R., Karlan, B. Y. & Svendsen, C. N. 2017. Directed Differentiation of Human Induced Pluripotent Stem Cells into Fallopian Tube Epithelium. Sci Rep, 7, 10741.

Zondervan, K. T., Rahmioglu, N., Morris, A. P., Nyholt, D. R., Montgomery, G. W., Becker, C. M. & Missmer, S. A. 2016. Beyond Endometriosis Genome-Wide Association Study: From Genomics to Phenomics to the Patient. Semin Reprod Med, 34, 242-54.

* cited by examiner

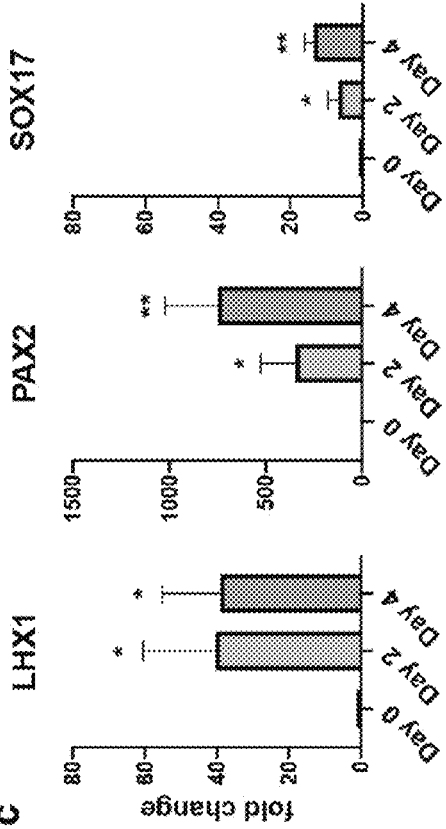
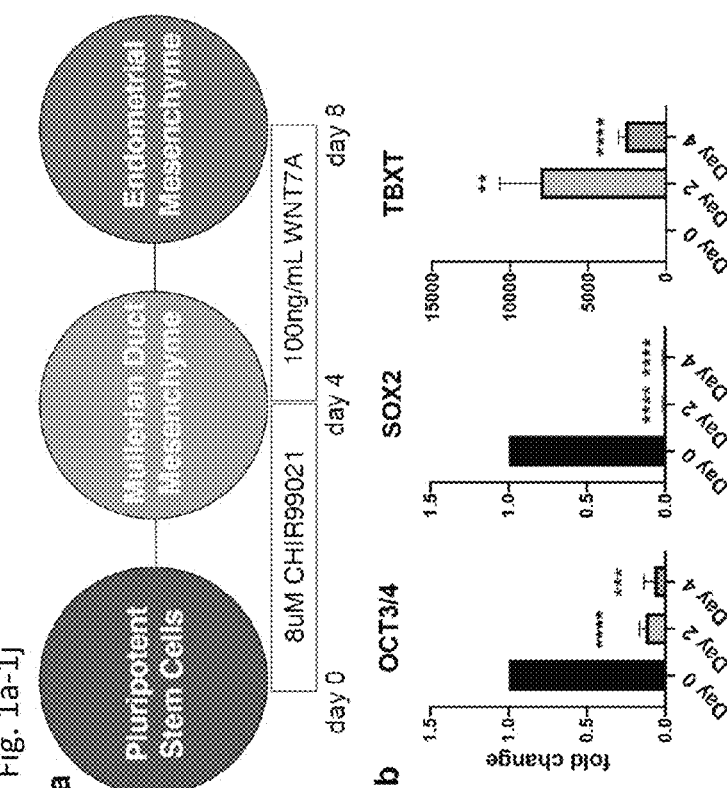
Fig. 1a-1j

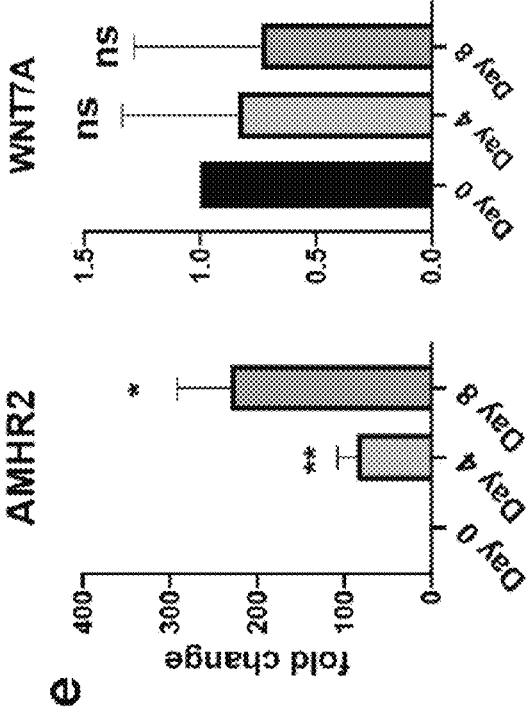
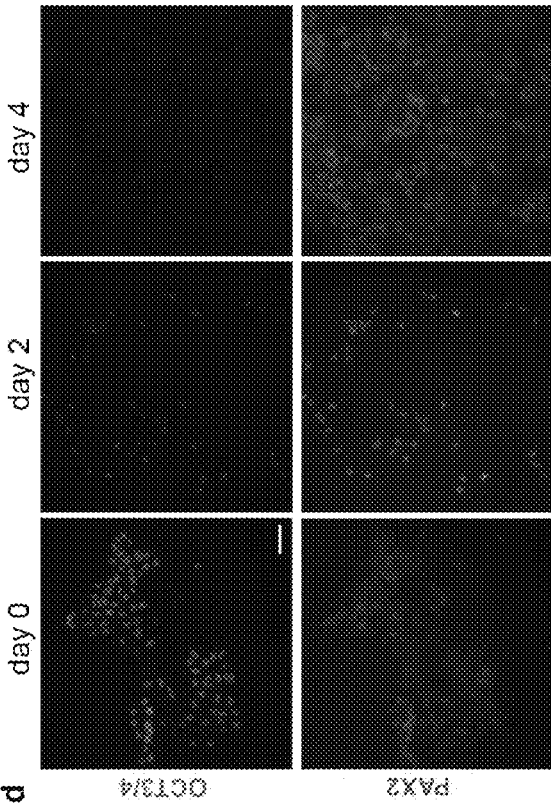
Fig. 1a-1j continued

Fig. 3a- Fig. 3g continued

Decidualized ESF Enriched Genes (67)

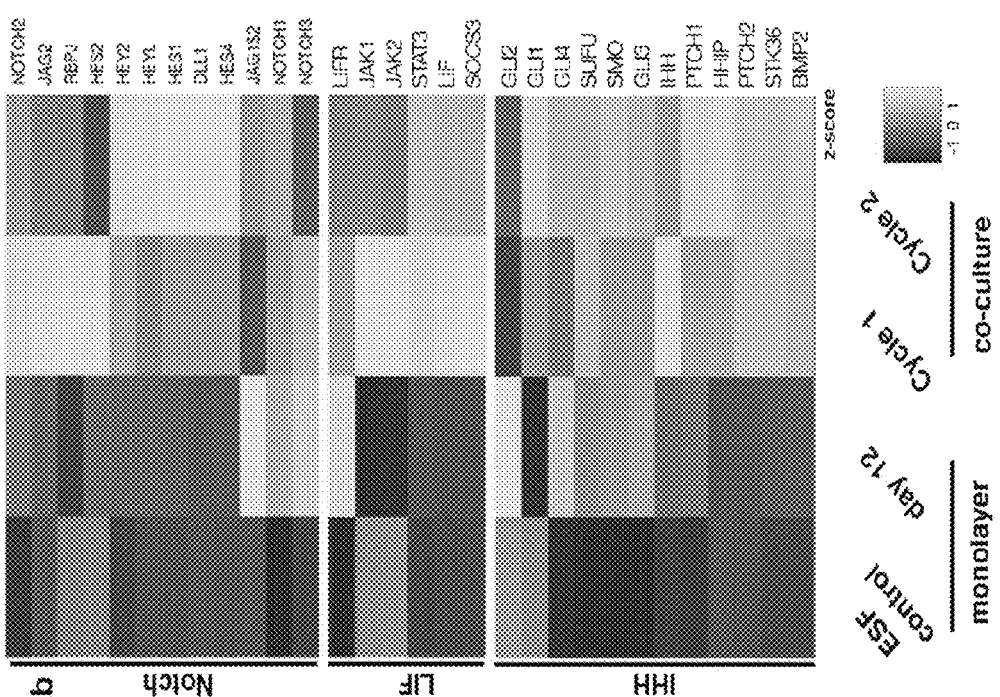
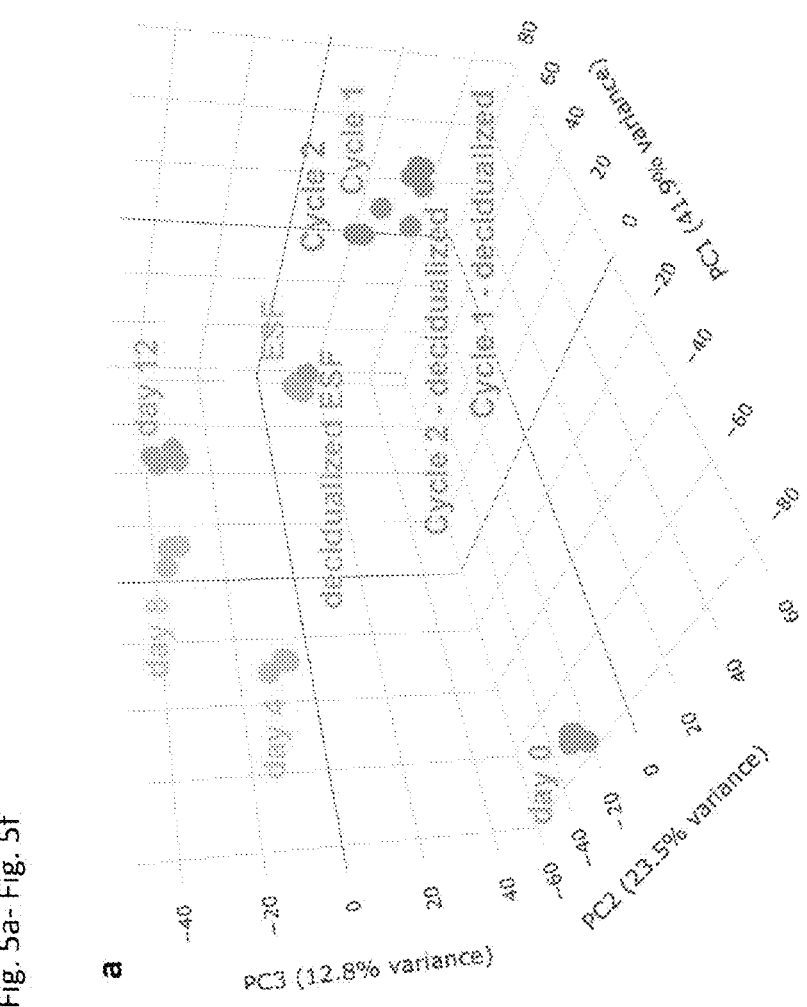
Fig. 5a- Fig. 5f

Fig. 5a- Fig. 5f
continued
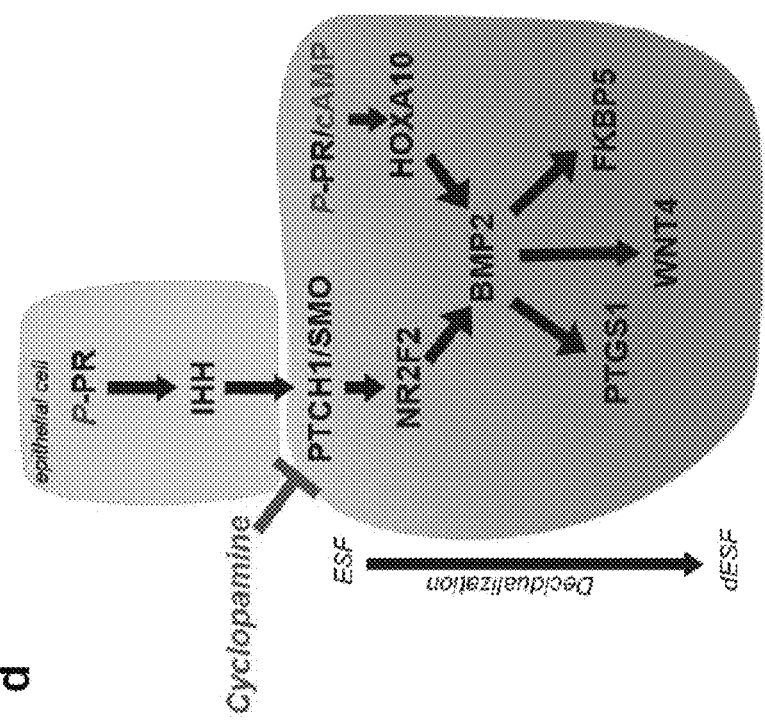
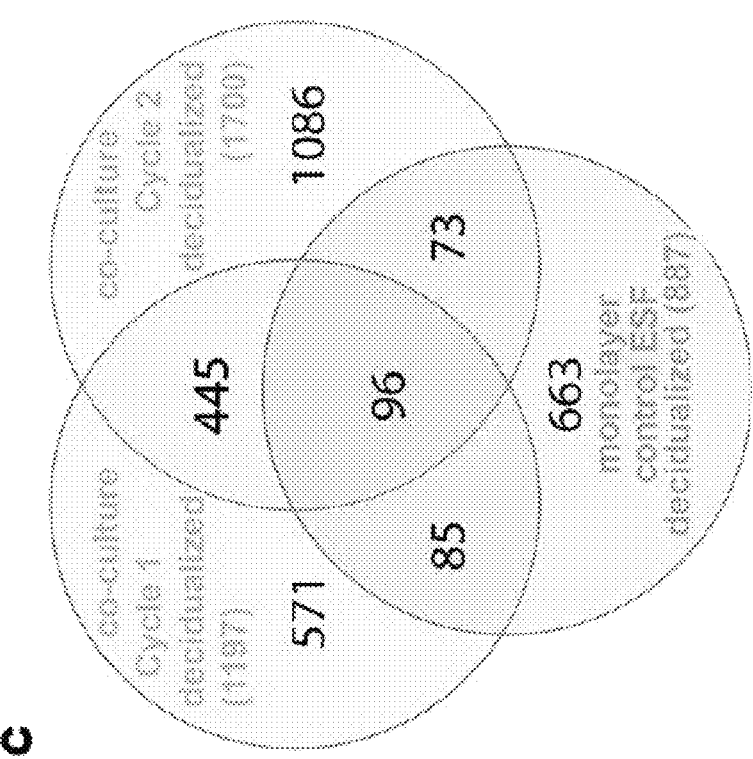

Fig. 5a- Fig. 5f
continued
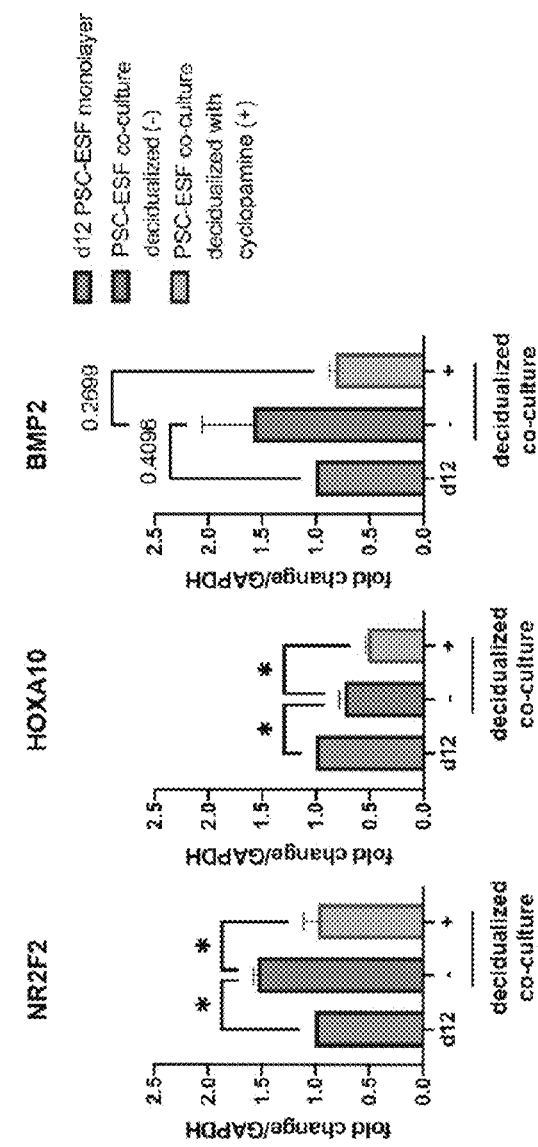
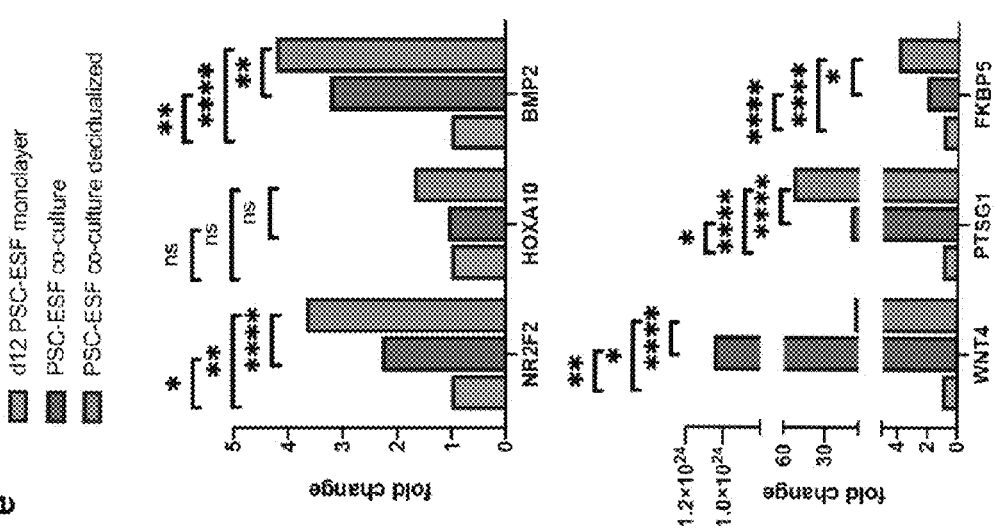

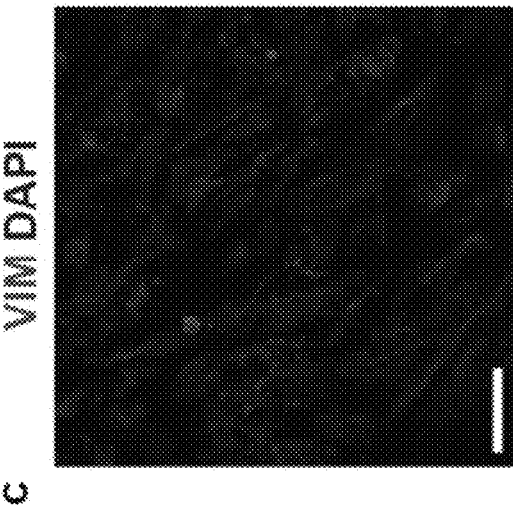
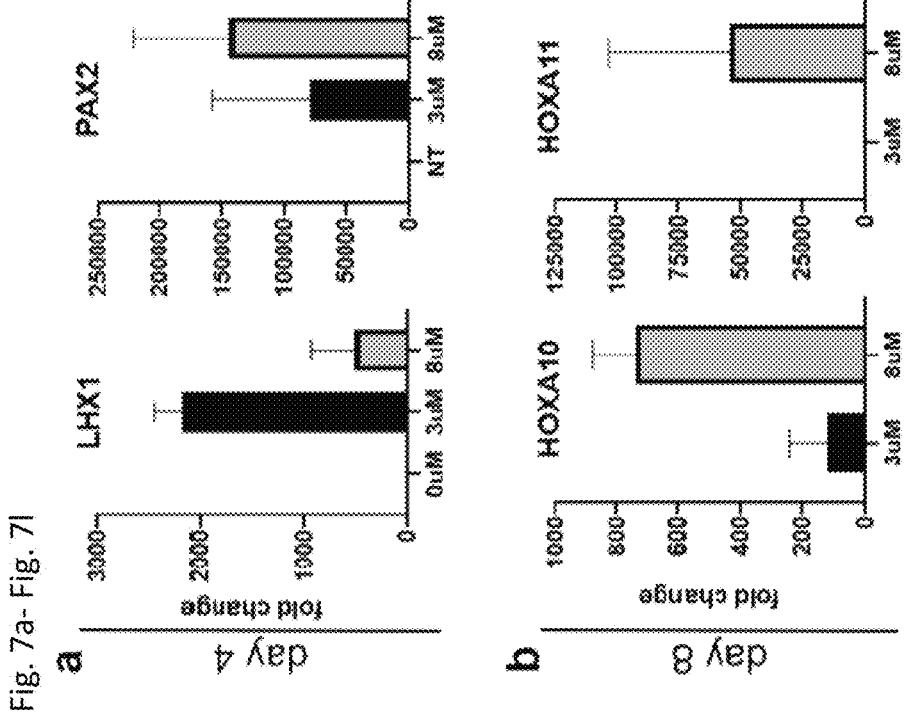
Fig. 7a - Fig. 7l

Fig. 7a- Fig. 7l continued
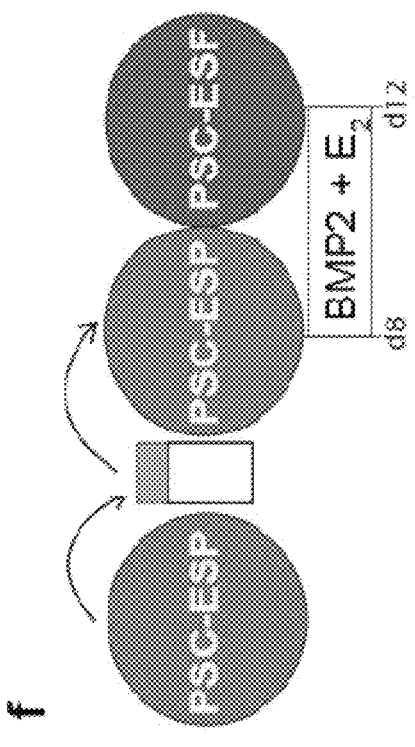
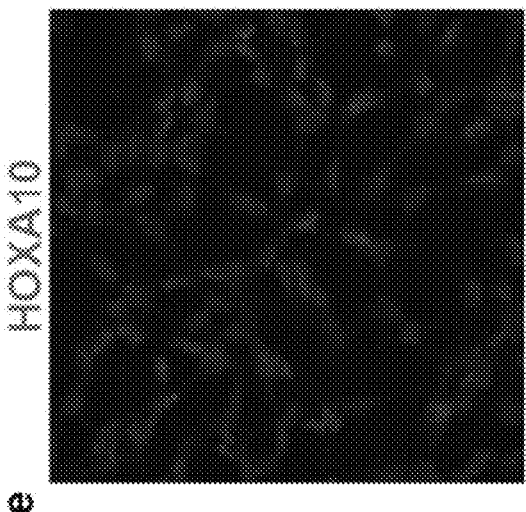
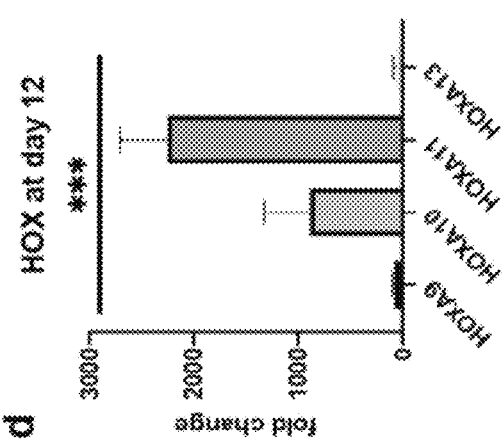

Fig. 8a- Fig. 8h
continued

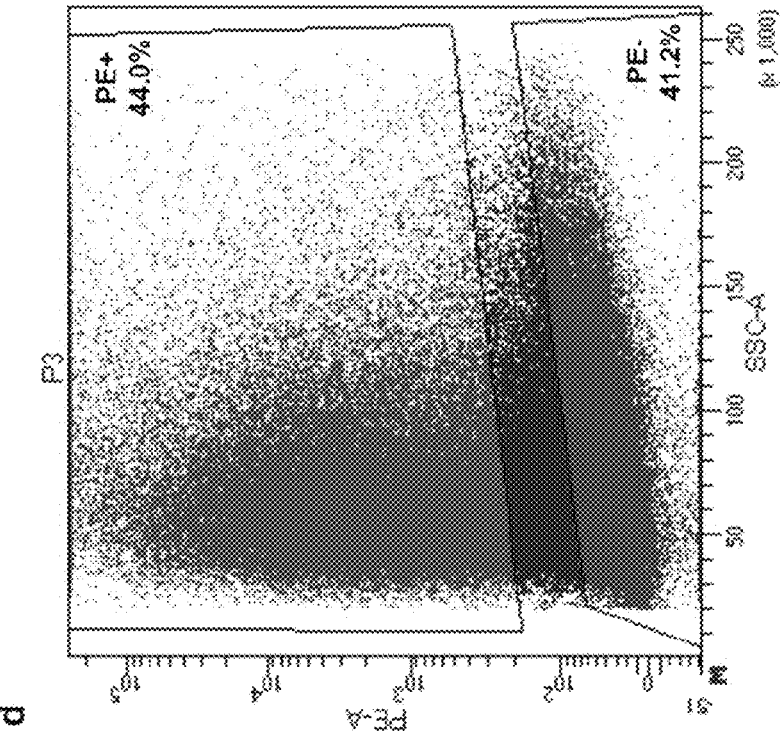
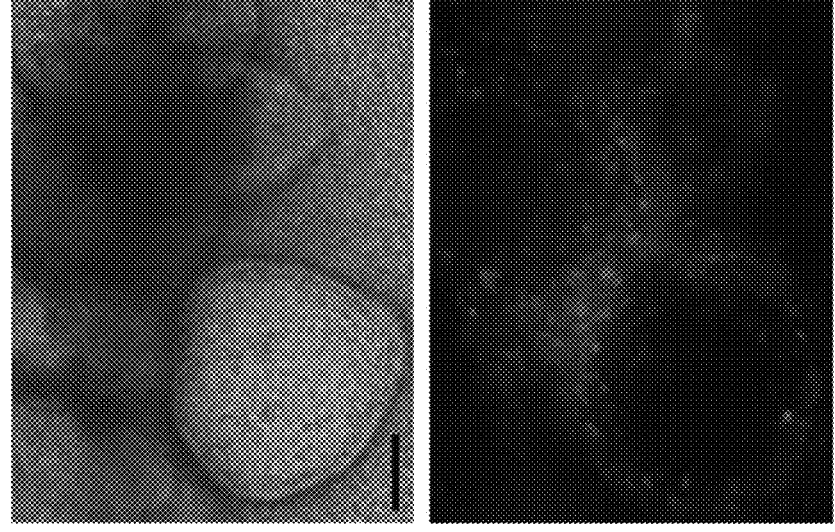
Fig. 11a- Fig. 11d continued

Fig. 12a- Fig. 12d
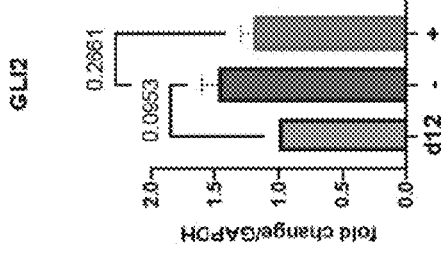
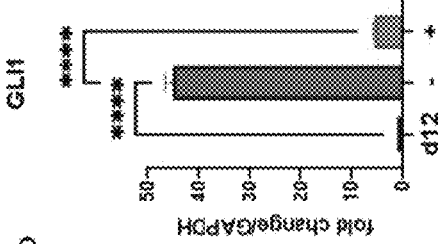
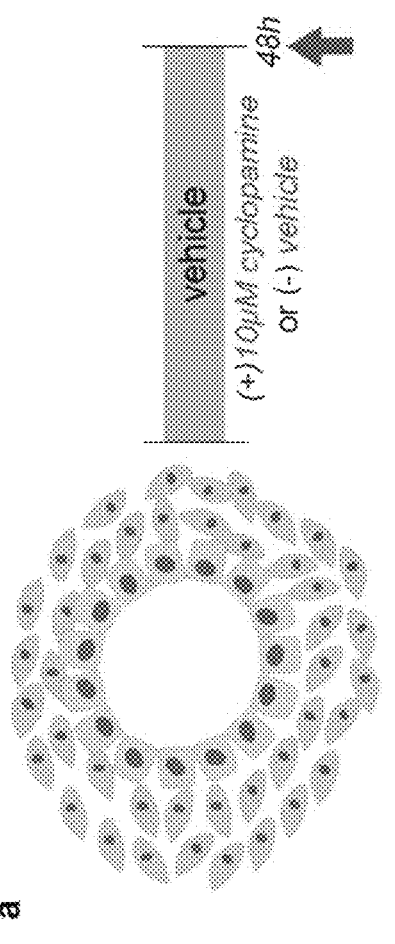

c d

Fig. 13a- Fig. 13b a   Rb-IgG Control for
PAX2, PDGFRβ,
HAND2, HOXA11, HOXA10

Fig. 13a- Fig. 13b continued b

Figures 13A, 13B:
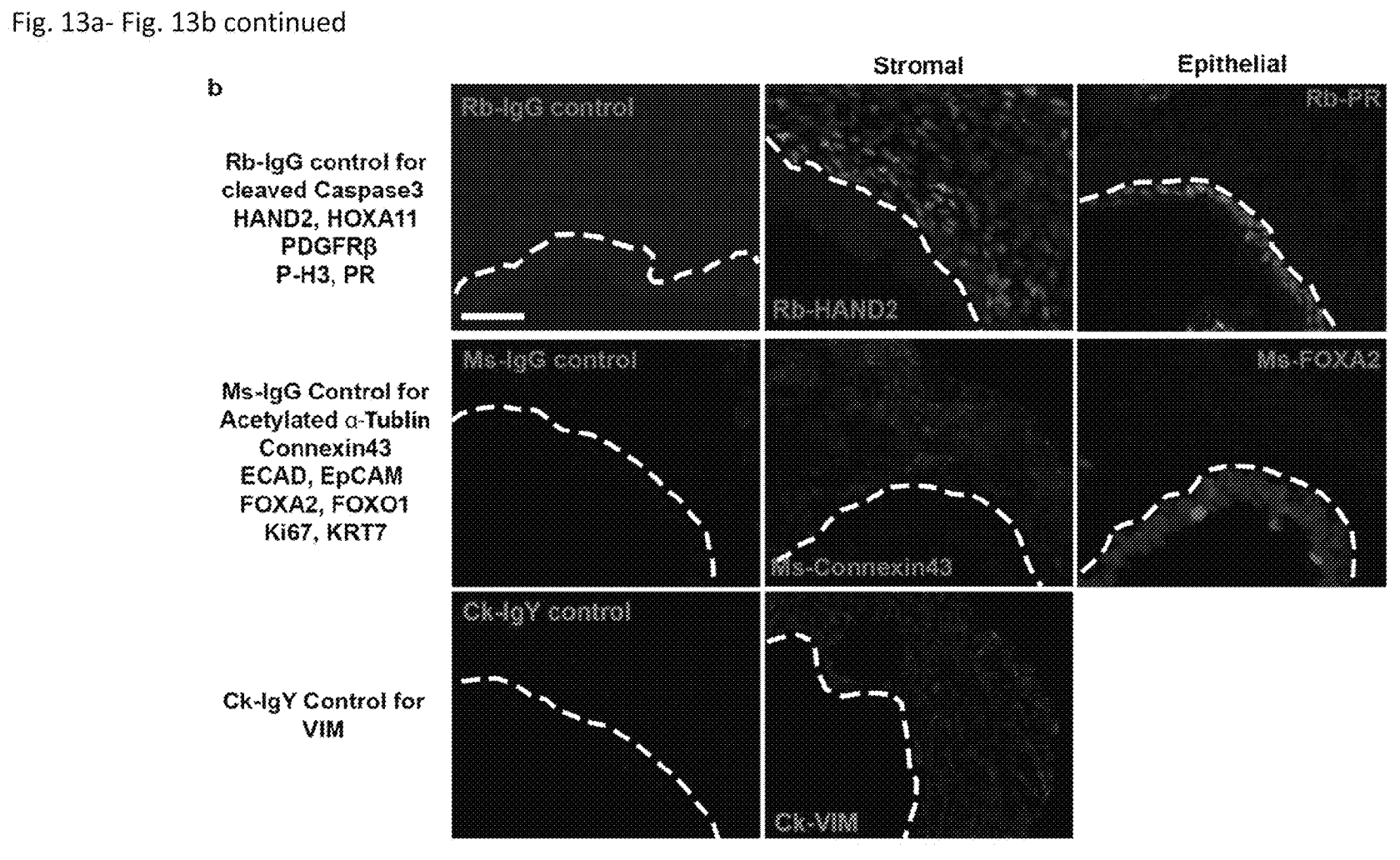

Rb-IgG control for
cleaved Caspase3
HAND2, HOXA11
PDGFRβ
P-H3, PR

Ms-IgG Control for
Acetylated α-Tublin
Connexin43
ECAD, EpCAM
FOXA2, FOXO1
Ki67, KRT7

Ck-IgY Control for
VIM

SEQUENCE LISTING

<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Synthetic- GAPDH forward primer

<400> SEQUENCE: 1
acaccatggg gaaggtgaag                                          20

<210> SEQ ID NO 2
<211> LENGTH: 18
<212> TYPE: DNA
<213> ORGANISM: Artificial Sequence
<220> FEATURE:
<223> OTHER INFORMATION: Synthetic- reverse primer-  GAPDH

<400> SEQUENCE: 2
gtgaccaggc gcccaata                                             18

<210> SEQ ID NO 3
<211> LENGTH: 26
<212> TYPE: DNA
<213> ORGANISM: Artificial Sequence
<220> FEATURE:
<223> OTHER INFORMATION: Synthetic- forward primer- BRACHYURY

<400> SEQUENCE: 3
gccctctccc tccctccac gcacag                                  26

<210> SEQ ID NO 4
<211> LENGTH: 26
<212> TYPE: DNA
<213> ORGANISM: Artificial Sequence
<220> FEATURE:
<223> OTHER INFORMATION: Synthetic- reverse primer- BRACHYURY

<400> SEQUENCE: 4
cggcgccgtt gctcacagac cacagg                                  26

<210> SEQ ID NO 5
<211> LENGTH: 20
<212> TYPE: DNA
<213> ORGANISM: Artificial Sequence
<220> FEATURE:
<223> OTHER INFORMATION: Synthetic- forward primer- LHX1

<400> SEQUENCE: 5
atgcaacctg accgagaagt                                          20

<210> SEQ ID NO 6
<211> LENGTH: 19
<212> TYPE: DNA
<213> ORGANISM: Artificial Sequence
<220> FEATURE:
<223> OTHER INFORMATION: Synthetic- reverse primer-LHX1

<400> SEQUENCE: 6
caggtcgcta ggggagatg                                           19

<210> SEQ ID NO 7
<211> LENGTH: 19
<212> TYPE: DNA
<213> ORGANISM: Artificial Sequence
<220> FEATURE:
<223> OTHER INFORMATION: Synthetic- forward primer- PAX2

<400> SEQUENCE: 7 gcaacccgc cttactaat                                                                          19

<210> SEQ ID NO 8
<211> LENGTH: 20
<212> TYPE: DNA
<213> ORGANISM: Artificial Sequence
<220> FEATURE:
<223> OTHER INFORMATION: Synthetic- reverse primer- PAX2

<400> SEQUENCE: 8
aactagtggc ggtcataggc                                                                        20

<210> SEQ ID NO 9
<211> LENGTH: 24
<212> TYPE: DNA
<213> ORGANISM: Artificial Sequence
<220> FEATURE:
<223> OTHER INFORMATION: Synthetic- forward primer- OCT3/4

<400> SEQUENCE: 9
gacaggggga ggggaggagc tagg                                                                   24

<210> SEQ ID NO 10
<211> LENGTH: 26
<212> TYPE: DNA
<213> ORGANISM: Artificial Sequence
<220> FEATURE:
<223> OTHER INFORMATION: Synthetic- reverse primer- OCT3/4

<400> SEQUENCE: 10
cttccctcca accagttgcc ccaaac                                                                 26

<210> SEQ ID NO 11
<211> LENGTH: 26
<212> TYPE: DNA
<213> ORGANISM: Artificial Sequence
<220> FEATURE:
<223> OTHER INFORMATION: Synthetic- forward primer- SOX2

<400> SEQUENCE: 11
gggaaatggg aggggtgcaa aagagg                                                                 26

<210> SEQ ID NO 12
<211> LENGTH: 26
<212> TYPE: DNA
<213> ORGANISM: Artificial Sequence
<220> FEATURE:
<223> OTHER INFORMATION: Synthetic- reverse primer- SOX2

<400> SEQUENCE: 12
ttgcgtgagt gtggatggga ttggtg                                                                 26

<210> SEQ ID NO 13
<211> LENGTH: 26
<212> TYPE: DNA
<213> ORGANISM: Artificial Sequence
<220> FEATURE:
<223> OTHER INFORMATION: Synthetic- forward primer-  SOX17

<400> SEQUENCE: 13
cgctttcatg gtgtgggcta aggacg                                                                 26

-continued

```
<210> SEQ ID NO 14
<211> LENGTH: 26
<212> TYPE: DNA
<213> ORGANISM: Artificial Sequence
<220> FEATURE:
<223> OTHER INFORMATION: Synthetic- reverse primer- SOX17

<400> SEQUENCE: 14
tagttggggt ggtcctgcat gtgctg                                    26

<210> SEQ ID NO 15
<211> LENGTH: 23
<212> TYPE: DNA
<213> ORGANISM: Artificial Sequence
<220> FEATURE:
<223> OTHER INFORMATION: Synthetic- forward primer- AMHR2

<400> SEQUENCE: 15
cgaccacatt gtccgattta tca                                       23

<210> SEQ ID NO 16
<211> LENGTH: 19
<212> TYPE: DNA
<213> ORGANISM: Artificial Sequence
<220> FEATURE:
<223> OTHER INFORMATION: Synthetic- reverse primer- AMHR2

<400> SEQUENCE: 16
cccttgggat gcagttcca                                            19

<210> SEQ ID NO 17
<211> LENGTH: 21
<212> TYPE: DNA
<213> ORGANISM: Artificial Sequence
<220> FEATURE:
<223> OTHER INFORMATION: Synthetic- forward primer- WNT7A

<400> SEQUENCE: 17
ctgtggctgc gacaaagaga a                                         21

<210> SEQ ID NO 18
<211> LENGTH: 19
<212> TYPE: DNA
<213> ORGANISM: Artificial Sequence
<220> FEATURE:
<223> OTHER INFORMATION: Synthetic- reverse primer- WNT7A

<400> SEQUENCE: 18
gccgtggcac ttacattcc                                            19

<210> SEQ ID NO 19
<211> LENGTH: 20
<212> TYPE: DNA
<213> ORGANISM: Artificial Sequence
<220> FEATURE:
<223> OTHER INFORMATION: Synthetic- forward primer- HOXA9

<400> SEQUENCE: 19
tacgtggact cgttcctgct                                           20

<210> SEQ ID NO 20
<211> LENGTH: 19
<212> TYPE: DNA
<213> ORGANISM: Artificial Sequence
<220> FEATURE:
<223> OTHER INFORMATION: Synthetic- reverse primer- HOXA9
```

```
<400> SEQUENCE: 20
cgtcgccttg gactggaag                                          19

<210> SEQ ID NO 21
<211> LENGTH: 19
<212> TYPE: DNA
<213> ORGANISM: Artificial Sequence
<220> FEATURE:
<223> OTHER INFORMATION: Synthetic- forward primer- HOXA10

<400> SEQUENCE: 21
ctcgcccata gacctgtgg                                          19

<210> SEQ ID NO 22
<211> LENGTH: 19
<212> TYPE: DNA
<213> ORGANISM: Artificial Sequence
<220> FEATURE:
<223> OTHER INFORMATION: Synthetic- reverse primer- HOXA10

<400> SEQUENCE: 22
gttctgcgcg aaagagcac                                          19

<210> SEQ ID NO 23
<211> LENGTH: 18
<212> TYPE: DNA
<213> ORGANISM: Artificial Sequence
<220> FEATURE:
<223> OTHER INFORMATION: Synthetic- forward primer- HOXA11

<400> SEQUENCE: 23
cggccacact gaggacaa                                           18

<210> SEQ ID NO 24
<211> LENGTH: 22
<212> TYPE: DNA
<213> ORGANISM: Artificial Sequence
<220> FEATURE:
<223> OTHER INFORMATION: Synthetic- reverse primer- HOXA11

<400> SEQUENCE: 24
ctgaagaaga actcccgttc ca                                      22

<210> SEQ ID NO 25
<211> LENGTH: 20
<212> TYPE: DNA
<213> ORGANISM: Artificial Sequence
<220> FEATURE:
<223> OTHER INFORMATION: Synthetic- forward primer- HOXA13

<400> SEQUENCE: 25
ctgccctatg gctacttcgg                                         20

<210> SEQ ID NO 26
<211> LENGTH: 19
<212> TYPE: DNA
<213> ORGANISM: Artificial Sequence
<220> FEATURE:
<223> OTHER INFORMATION: Synthetic- reverse primer- HOXA13

<400> SEQUENCE: 26
ccggcggtat ccatgtact                                          19

<210> SEQ ID NO 27
```

```
<211> LENGTH: 22
<212> TYPE: DNA
<213> ORGANISM: Artificial Sequence
<220> FEATURE:
<223> OTHER INFORMATION: Synthetic- forward primer- PGR

<400> SEQUENCE: 27
agccaagaag agttcctctg ta                                          22

<210> SEQ ID NO 28
<211> LENGTH: 20
<212> TYPE: DNA
<213> ORGANISM: Artificial Sequence
<220> FEATURE:
<223> OTHER INFORMATION: Synthetic- reverse primer- PGR

<400> SEQUENCE: 28
ttgacttcgt agcccttcca                                             20

<210> SEQ ID NO 29
<211> LENGTH: 20
<212> TYPE: DNA
<213> ORGANISM: Artificial Sequence
<220> FEATURE:
<223> OTHER INFORMATION: Synthetic- forward primer- PRL

<400> SEQUENCE: 29
catcaacagc tgccacactt                                             20

<210> SEQ ID NO 30
<211> LENGTH: 20
<212> TYPE: DNA
<213> ORGANISM: Artificial Sequence
<220> FEATURE:
<223> OTHER INFORMATION: Synthetic- reverse primer-  PRL

<400> SEQUENCE: 30
cgtttggttt gctcctcaat                                             20

<210> SEQ ID NO 31
<211> LENGTH: 23
<212> TYPE: DNA
<213> ORGANISM: Artificial Sequence
<220> FEATURE:
<223> OTHER INFORMATION: Synthetic- forward primer- FOXO1

<400> SEQUENCE: 31
tgataactgg agtacatttc gcc                                         23

<210> SEQ ID NO 32
<211> LENGTH: 22
<212> TYPE: DNA
<213> ORGANISM: Artificial Sequence
<220> FEATURE:
<223> OTHER INFORMATION: Synthetic- reverse primer- FOXO1

<400> SEQUENCE: 32
cggtcataat gggtgagagt ct                                          22

<210> SEQ ID NO 33
<211> LENGTH: 20
<212> TYPE: DNA
<213> ORGANISM: Artificial Sequence
<220> FEATURE:
<223> OTHER INFORMATION: Synthetic- forward primer- IGFBP1

<400> SEQUENCE: 33
```

-continued

```
ctatgatggc tcgaaggctc                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic- reverse primer- IGFBP1

<400> SEQUENCE: 34
ttcttgttgc agtttggcag                                             20

<210> SEQ ID NO 35
<211> LENGTH: 23
<212> TYPE: DNA
<213> ORGANISM: Artificial Sequence
<220> FEATURE:
<223> OTHER INFORMATION: Synthetic- forward primer- GLI1

<400> SEQUENCE: 35
ccaactccac aggcatacag gat                                         23

<210> SEQ ID NO 36
<211> LENGTH: 22
<212> TYPE: DNA
<213> ORGANISM: Artificial Sequence
<220> FEATURE:
<223> OTHER INFORMATION: Synthetic- reverse primer- GLI1

<400> SEQUENCE: 36
cacagattca ggctcacgct tc                                          22

<210> SEQ ID NO 37
<211> LENGTH: 24
<212> TYPE: DNA
<213> ORGANISM: Artificial Sequence
<220> FEATURE:
<223> OTHER INFORMATION: Synthetic- forward primer- GLI2

<400> SEQUENCE: 37
aagtcactca aggattcctg ctca                                        24

<210> SEQ ID NO 38
<211> LENGTH: 22
<212> TYPE: DNA
<213> ORGANISM: Artificial Sequence
<220> FEATURE:
<223> OTHER INFORMATION: Synthetic- reverse primer- GLI2

<400> SEQUENCE: 38
gttttccagg atggagccac tt                                          22

<210> SEQ ID NO 39
<211> LENGTH: 23
<212> TYPE: DNA
<213> ORGANISM: Artificial Sequence
<220> FEATURE:
<223> OTHER INFORMATION: Synthetic- forward primer- NR2F2

<400> SEQUENCE: 39
tcatgggtat cgagaacatt tgc                                         23

<210> SEQ ID NO 40
<211> LENGTH: 21
<212> TYPE: DNA
```

-continued

```
<213> ORGANISM: Artificial Sequence
<220> FEATURE:
<223> OTHER INFORMATION: Synthetic- reverse primer- NR2F2

<400> SEQUENCE: 40
ttcaacacaa acagctcgct c                                              21

<210> SEQ ID NO 41
<211> LENGTH: 20
<212> TYPE: DNA
<213> ORGANISM: Artificial Sequence
<220> FEATURE:
<223> OTHER INFORMATION: Synthetic- forward primer-  BMP2

<400> SEQUENCE: 41
ggaacggaca ttcggtcctt                                                20

<210> SEQ ID NO 42
<211> LENGTH: 21
<212> TYPE: DNA
<213> ORGANISM: Artificial Sequence
<220> FEATURE:
<223> OTHER INFORMATION: Synthetic- reverse primer- BMP2

<400> SEQUENCE: 42
caccatggtc gacctttagg a                                              21
```

METHODS OF GENERATING HUMAN ENDOMETRIAL STROMAL FIBROBLASTS AND THREE-DIMENSIONAL MULTI-LAYERED HUMAN ENDOMETRIAL TISSUE COMPOSITIONS

CROSS-REFERENCE TO RELATED APPLICATIONS

This patent application claims the benefit of priority of U.S. Provisional Patent Application No. 63/201,494 filed on Apr. 30, 2021, which is incorporated herein by reference in its entirety.

SEQUENCE LISTING

This application contains, as a separate part of the disclosure, a Sequence Listing in computer readable form (filename: 702581.02133_SeqList.txt; Created: 29 Apr. 2022; 88,000 bytes), which is incorporated by reference in its entirety.

FIELD OF INVENTION

The field of the invention relates to stem cell differentiation methods and the generation of three-dimensional, multilayered tissues, such as endometrial tissues, to treat, for example, pregnancy related disease, to provide a platform for drug screening and testing, and to provide cells for replacement therapy.

BACKGROUND

The human endometrium cyclically proliferates, differentiates, and sheds in response to hormones. This cyclic process, also known as spontaneous decidualization, occurs in response to ovulation in the absence of a fertilized oocyte and implantation (Kin et al., 2015). In the event of successful fertilization, implantation of a blastocyst results in further differentiation in response to molecular signaling and cellular invasion by fetal trophectoderm. Many laboratory animal models, such as mice and rats, lack both spontaneous decidualization and the cellular profile and dynamics of human placentation and thus are imperfect models for many of the unique features of the human endometrium (Hemberger et al., 2020).

Human endometrial stromal fibroblasts (hESF) established from patient biopsies have been widely used to understand the process of decidualization. While these primary cells have greatly informed the mechanisms governing hESF function, they have provided only limited knowledge of the factors governing the development of hESF. Numerous studies have demonstrated the presence of a stem cell population in the basalis layer of the endometrium capable of generating hESF (Yin et al., 2019, Schwab and Gargett, 2007, Masuda et al., 2012). The ability to identify and isolate adult endometrial mesenchymal stem cells (eMSC) is a significant advance for the study of endometrial disease, however the mechanisms for maintenance and expansion of the eMSC and subsequent differentiation into hESF remain to be defined (Gurung et al., 2018). Further, it is unknown whether the etiology of endometrial and reproductive disease is developmental or develops de novo in the adult.

In the past decade, induced pluripotent stem cells (iPSC) have proven to be invaluable for the study of both normal development and human disease. Differentiation protocols from iPSC to many cell types of interest have been continually optimized for improved yield, purity, and functional application. However, the development of differentiation protocols for hESF-like cells from iPSC has just begun (Miyazaki et al., 2018). This initial protocol used embryoid bodies to produce hESF-like cells that responded to hormones to decidualize, but it remains to be determined whether these cells interact with other endometrial cell types and faithfully model endometrial development or disease states.

While ESFs represent the bulk of the cells in the endometrium, epithelial cells also participate in decidualization and are necessary for endometrial processes related to implantation. Three-dimensional (3D) hormone responsive organoid models of the human epithelium have been established by several groups from endometrial biopsy and first trimester placenta (Turco et al., 2017, Boretto et al., 2017). While decidual ESF are also present when endometrial epithelial organoid (EEO) cultures are being established (Male et al., 2012, Haider et al., 2019), they do not associate with the EEOs and are not maintained over time in co-cultures (Turco et al., 2017, Marinic and Lynch, 2019, Boretto et al., 2017). Endometrial spheroids containing both stromal and epithelial cells can be generated from endometrial biopsies, but they cannot be maintained long term, and have not been characterized for epithelial and stromal decidualization and interactions (Wiwatpanit et al., 2020).

SUMMARY

Disclosed herein are methods for directing differentiation of human pluripotent stem cells into endometrial stromal fibroblasts (PSC-ESF) that are capable of co-culturing with endometrial epithelial organoid cells derived from placenta, such as term placenta. Also provided herein are compositions comprising the PSC-ESF cells, and methods of using the cells.

In some embodiments, methods disclosed herein comprise obtaining human endometrial stromal fibroblasts (PSC-ESF). In some embodiments, the methods comprise (a) culturing pluripotent stem cells (PSCs) with a first Wnt/β-catenin agonist for about 4 days; (b) culturing the cells of (a) with a second Wnt/β-catenin agonist for about 4 days; (c) culturing the cells of (b) with Bone Morphogenetic Protein 2 (BMP-2) and β-estradiol for about 4 days; wherein the cultured cells of (c) comprise PSC-ESF cells.

Also disclosed are methods of obtaining a three-dimensional, multilayered human endometrial tissue composition responsive to cyclic hormone treatment. In some embodiments, the methods comprise (a) combining (i) dissociated cells from endometrial epithelial organoids (EEO), and (ii) dissociated PSC-ESF in a porous substrate comprising extracellular matrix components; (b) culturing the combined cells in the porous substrate for about 10 days, wherein the combined cells self-assemble to form a three-dimensional human endometrial tissue comprising an outer layer of PSC-ESF and an inner layer of epithelial cells, and wherein the three-dimensional human endometrial tissue is responsive to cyclic hormone treatment.

Also disclosed are engineered, three-dimensional, multi-layered human endometrial tissue composition. In some embodiments, the compositions comprise an outer layer of PSC-ESF and an inner layer of epithelial cells, wherein outer layer of PSC-ESF and an inner layer of epithelial cells are in direct contact, and wherein the outer layer of PSC-ESF cells interface with the inner layer of epithelial cells along the Laminin[+] basolateral surface of the epithelial cells.

Also disclosed herein are methods of testing a compound for effects on endometrial tissue. In some embodiments, the method comprises (a) contacting a test compound to a three-dimensional multilayered human endometrial tissue composition; and (b) detecting an effect of the agent on one or more cell types within the contacted endometrial tissue. In some embodiments, a three-dimensional multilayered endometrial composition of the present disclosure is used in a drug discovery screen.

Also disclosed are method for modeling decidualization of the human endometrium. In some embodiments, the methods comprise (a) culturing the three-dimensional, multilayered human endometrial tissue composition of the present disclosure with estradiol ($E_2$) for about 2 days; (b) culturing the cells of (a) with 8-bromoadenosine-cAMP (cAMP), medroxyprogesterone 17-acetate, and $E_2$ for about 14 days; wherein the cells of (b) express prolactin (PRL), forkhead box O1 (FOXO1), insulin growth factor binding protein (IGFBP1), gap junction protein alpha 1 (GJA1), and heart and neural crest derivatives expressed transcript 2 (HAND2).

Methods of using the PSC-ESF cells, and/or the three-dimensional endometrial tissue compositions for drug screening and therapeutic purposes are also disclosed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figures 1A, 1B, 1C, 1D, 1E, 1F, 1G, 1H, 1I, 1J:
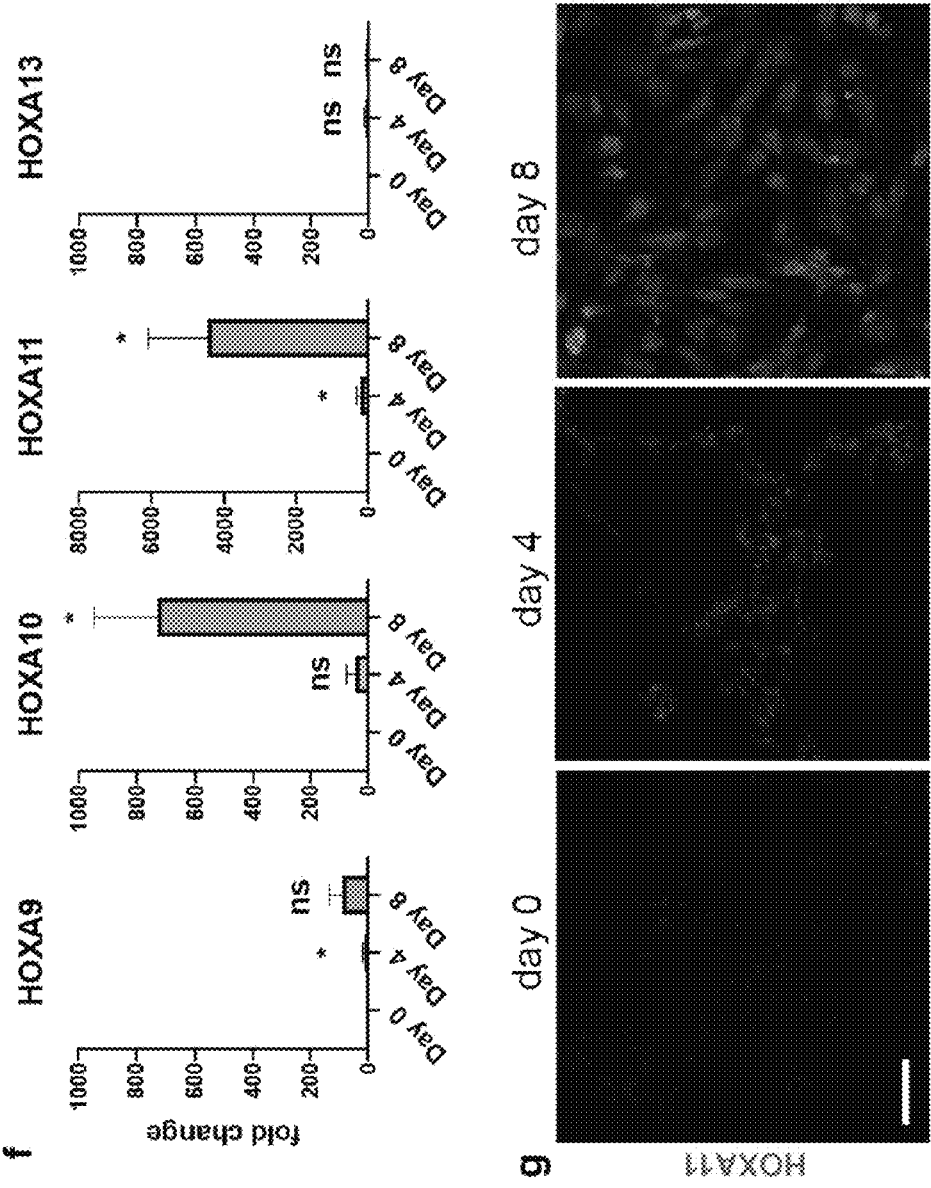
FIG. 1a-1j. Differentiation of pluripotent stem cells to endometrial mesenchyme progenitors. a. Schematic of differentiation protocol. b. Quantitative PCR (qPCR) analysis of mRNA expression showing down regulation of pluripotency markers OCT3/4 (d0 vs d2 **p<0.0001, n=3) and SOX2 (d0 vs d2 p<0.0001, n=6), along with upregulation of mesodermal marker Brachyury (d0 vs d2 p=0.0049, n=8) by day 2 of 8 μM of CHIR9902 treatment. c. Upregulation of intermediate mesoderm and Müllerian duct markers LHX1 (d0 vs d2 *p=0.0226, n=7) and PAX2 (d0 vs d2 *p=0.0250, n=5) were detected by day 2 and maintained at day 4 (LHX1 d0 vs d4 *p=0.0269, n=11; PAX2 d0 vs d4 **p=0.0071, n=7). A small but significant upregulation of SOX17 (d0 vs d2 *p=0.0348, n=3; d0 vs d4 p=0.0015, n=5), a marker of endoderm and mesoendoderm precursors, was also detected. d. Immunocytochemical analyses showing decreased nuclear OCT3/4 and increased nuclear PAX2 protein day 0-day 4. e. qPCR analyses of AMHR2 and WNT5A, markers of Müllerian mesenchyme, showing a significant increase of expression (AMHR2 d0 vs d4 p=0.0016, n=8). Day 4 treatment of 100 ng/mL WNT7A led to increased or maintained expression of Müllerian duct mesenchyme markers (AMHR2 d4 vs d8 *p=0.0340, n=7; WNT7A d4 vs d8 ****p<0.0001, n=6) and no activation of Müllerian duct epithelial cell marker WNT7A (d0 vs d4 ns p=0.7216, n=4; d4 vs d8 ns p=0.8982, n=4). f. WNT7A treatment between day 4 through 8 also significantly increased expression of the uterine stroma specific Homeobox genes, HOXA10 (d4 vs d8 * p=0.0219, n=4) and HOXA11 (d4 vs d8 * p=0.0199, n=8). Regionalization genes expressed by the fallopian tube (HOXA9, d4 vs d8 ns p=0.1748, n=4) and vagina (HOXA13, d4 vs d8 ns p=0.5174, n=5) were not significantly upregulated. g. Immunocytochemistry showing increasing nuclear HOXA11 protein between day 0 and day 8. h. Immunocytochemistry showing expression of mesenchyme markers PDGFRβ (red)

and VIM (magenta) with VIM co-expressed with HOXA11 (green). i. Immunocytochemistry showing co-expression of Müllerian mesenchyme specific AMHR2 (magenta) and HOXA11 (green). Ki67 (red) staining indicates that the majority of AMHR2$^+$HOXA11$^+$ cells are in cell cycle at Day 8 of differentiation. j. Quantification of the percentage of day 8 cells that express AMHR2 and HOXA11 (78.5%, n=3), HOXA11 (92.3%, n=3), and Ki67 (93.3%, n=2). For qPCR analyses, gene expression is normalized to GAPDH and calculated as fold change over expression at day 0. Data is represented as mean±SEM in b, c, e, f, and j. Scale bars, 50 μm in d, g, h, i.

FIG. 2a-FIG. 2i. Maturation of endometrial mesenchyme progenitors to decidualized endometrial stroma a. Schematic of decidualization protocol. b. Immunocytochemical analyses of HOXA11 (green), AMHR2 (magenta), and Ki67 (red) expression in PSC-ESP at day 12 after by treatment of 10 ng/mL BMP2 and 10 nM $E_2$. c. Quantification of the percentage of day 12 cells that express both AMHR2 and HOXA11 (Magenta, 0.95%, n=3), HOXA11$^+$ (Green, 92%, n=3) and Ki67$^+$ (Red, 92.9%, n=2). d. Progesterone (PRA) and Estrogen (ERβ) receptor expression between day 8 and 12 as measured by immunoblot. e. Significant upregulation of both receptor proteins (PRA *p=0.0279, n=3; ERβ *p=0.0120, n=3) was detected between day 8 and day 12. Proteins were normalized to GAPDH for quantification. f. qPCR analysis of decidualization induced genes PRL (CEP vs. ESF *p=0.0154, n=6), FOXO1 (CEP vs. ESF *p=0.0188, n=4), and IGFBP1 (CEP vs. ESF n.s. p=0.0666, n=6), after 14 days of decidualization treatment compared to vehicle only and untreated ESF controls. Each gene was normalized to GAPDH and calculated as fold change over primary ESF. g. Brightfield phase images of PSC-ESF after 14 days of decidualization (cAMP+MPA+$E_2$, CEP) treatment had a cuboidal and compact cell morphology in comparison to vehicle treated. h. Immunocytochemistry showing increased nuclear HOXA11, nuclear FOXO1, cytoplasmic Connexin43 and nuclear HAND2 after 14 days of cAMP+MPA+$E_2$ treatment in comparison to vehicle only control. i. Heatmap highlighting gene expression of the various developmental stages of ESF development. As differentiation progresses from day 0 to day 12, gene expression is gained and lost to show a step-wise progression from pluripotency to ESF control. Data is represented as mean±SEM in c, e, and f. Scale bars, 100 μm in b, g, and h.

FIG. 3a-FIG. 3g. Self-aggregation of PSC-ESF and EEO to form a hormone responsive organoid co-culture. a. Schematic of co-culture protocol. b. Brightfield phase images showing EEO and PSC-ESF directly after plating and spontaneous co-culture formation by day 3. c. Schematic of co-culture decidualization treatment. d. Brightfield phase images of co-culture before and after decidualization treatment. Increased stromal cell layer thickness over the course of decidualization can be observed. e. In situ hybridization showing WNT5A transcript (green) expression is enriched in the stromal cell layer. The epithelial-stromal interface is marked by the perforated line. f. Immunocytochemistry demonstrating expression of endometrial stromal and epithelial markers in the appropriate compartments. The stromal compartment was indicated by PDGFRβ (green), nuclear HOXA11 (magenta), Laminin (green, arrows indicate basal surface of epithelium), and Vimentin (VIM, magenta). Epithelial cells expressed KRT7+(red), nuclear FOXA2+(red), E-cadherin+(red), EpCAM+(red). g. Immunocytochemical analysis of decidualization-induced proteins expression in the endometrial stromal and epithelial compartments after hormone or vehicle treatment including FOXO1 (green), HAND2 (green), Connexin43 (red), and PR (red). Scale bars 100 μm in b, d, and e-g.

FIG. 4a-FIG. 4h. Organoid co-cultures respond to cyclic hormone treatment and withdrawal a. Schematic of co-culture hormone cycling protocol. b. Inverted brightfield phase images and quantification showing thickened stromal layer morphology at the end of hormone treatment at Cycle 1 and Cycle 2 and a loosened stromal cell layer in response to hormone withdrawal. Radial profile plots illustrate integrated intensities around concentric circles as a function of distance from the center of the organoid. Quantification is normalized to the signal at the center of the organoid. The mean (red, blue, and green) and error (orange) (n=3) signal intensity is represented on the graph. c. Immunocytochemistry showing that loosened stromal cell morphology at 6 days after hormone withdrawal is associated with increased Ki67$^+$ cells. d. Quantification of percentage of stromal and epithelial cells in the organoid expressing Ki67 in each of the three phases. Significantly higher number stromal cells express Ki67 is observed during hormonal withdraw (F (2, 7)=5.457 *p=0.0373). No significant changes in Ki67$^+$ cells were detected epithelial cells (F (2, 7)=0.4422 ns p=0.6594). e. Immunocytochemistry demonstrates the co-culture remains hormone responsive after one hormone treatment cycle (Cycle 1). The co-culture remained hormone responsive as shown by a loss of decidualization markers FOXO1 (green), PR (magenta), and HOXA11 (red) during hormone withdrawal and a regaining of these markers after another 16 days of hormone treatment (Cycle 2). Epithelial marker KRT7 (green) expression did not changed across the three phases. f. Immunocytochemical analysis of HAND2 (green) and IGFBP1 (green) showed differential expression in Cycle 1 and Cycle 2 while Connexin 43 (red) and EpCAM (magenta) expression are not significantly different between the two cycles. g. Graphical representation of the number of decidualization-enriched genes detected in Cycles 1 and Cycle 2. Decidualization-enriched genes were selected from published single-cell RNA-sequencing studies (Suryawanshi et al., 2018; Vento-Tormo et al., 2018; Wang et al., 2020). Decidualization-enriched genes are mostly shared between Cycle 1 and Cycle 2 (28), however more were detected in Cycle 2 (36) compared to Cycle 1 (31). h. Transcripts per million (TPM) quantification of genes related to IGFBP1 processing and signaling in Cycle 1 and Cycle 2 decidualized PSC-ESF. TIMP3 is increased by decidualization over vehicle however, expression level was higher at the end of Cycle 2 (TIMP3 Cycle 1 vehicle v. Cycle 1 decidualized **padj=2.78E-13, Cycle 2 vehicle v. Cycle 2 decidualized padj=8.88E-93, Cycle 1 decidualized v. Cycle 2 vehicle **padj=7.07E-08). MMP9 and IGF1 are both decreased by decidualization over vehicle, but expression level of both was higher at the end of Cycle 1 (IGF1 Cycle 1 vehicle v. Cycle 1 decidualized *adjusted p-value, DESeq2 (padj)= 0.01019077, Cycle 2 vehicle v. Cycle 2 decidualized **padj=1.31E-31, Cycle 1 decidualized v. Cycle 2 vehicle padj=1.37E-15; MMP9 Cycle 1 vehicle v. Cycle 1 decidualized padj=7.52E-20, Cycle 2 vehicle v. Cycle 2 decidualized n. s. padj=0.54200741, Cycle 1 decidualized v. Cycle 2 vehicle **padj=5.67E-05). PSC-ESF appropriately changed gene expression in response to hormone treatment, however, differences in expression levels of TIMP3 and MMP9 could differentially regulate expression of IGFBP1 between Cycle 1 and Cycle 2. Gene expression is represented as TPM to show absolute expression level. Data is represented as mean±SEM in d; mean±SD in h. Scale bars, 200 μm in b, 100 μm in c, e, and f.

FIG. 5a-FIG. 5f. Developmental progression of PSC-ESF and signaling interactions with epithelial organoid in the co-culture model. a. 3D PCA plot illustrating progression from PSC toward ESF control. Day 12 PSC-ESF and co-cultured PSC-ESF cluster closely to ESF control. ESF and decidualized ESF control RNA libraries were generated previously from cultured ESF derived from the decidual membrane of term placenta and used with permission (Sakabe, 2020). b. Gene expression heatmap of selected molecular pathways know to be activated by endometrial epithelial to stromal signaling. Co-cultured cells Cycles 1 and 2 exhibit higher expression of signaling components than monolayer day 12 PSC-ESP and the ESF control. c. Venn Diagram showing overlap of genes significantly (adjusted p-value<0.05, calculated by DESeq2) upregulated>2-fold by decidualized monolayer (ESF control) or co-cultured (PSC-ESF Cycle 1 and Cycle 2) over respective vehicle treated groups. d. Schematic diagram of epithelial to stromal signaling mediated by IHH and BMP during decidualization. Cyclopamine inhibits hedgehog signaling as a SMO receptor antagonist. e. Fold change of BMP2 and upstream activators NR2F2 and HOXA10 relative to day 12 PSC-ESF (monolayer) after co-culture and after hormone treatment as measured by RNA sequencing. (NR2F2 d12 PSC-ESF monolayer v. PSC-ESF co-culture *adjusted p-value, DESeq2 (padj)=0.04577901, NR2F2 d12 PSC-ESF monolayer v. PSC-ESF co-culture decidualized *padj=0.00017372, PSC-ESF co-culture v. PSC-ESF co-culture decidualized padj=2.42E-09; HOXA10 d12 PSC-ESF monolayer v. PSC-ESF co-culture n.s. padj=1, d12 PSC-ESF monolayer v. PSC-ESF co-culture decidualized (n=3) n.s. padj=0.05040593, PSC-ESF co-culture v. PSC-ESF co-culture decidualized n.s. padj=0.11697528; BMP2 d12 PSC-ESF monolayer v. PSC-ESF co-culture padj=0.00590321, d12 PSC-ESF monolayer v. PSC-ESF co-culture decidualized **padj=4.74E-05, PSC-ESF co-culture v. PSC-ESF co-culture decidualized padj=0.0024381). Fold change of BMP2 targets WNT4, FKBP5, PTGS1, and TIMP3 transcripts relative to day 12 PSC-ESF (monolayer) after co-culture and after hormone treatment. (WNT4 d12 PSC-ESF monolayer v. PSC-ESF co-culture **padj=0.00246339, d12 PSC-ESF monolayer v. PSC-ESF co-culture decidualized *padj=0.04589137, PSC-ESF co-culture v. PSC-ESF co-culture decidualized ****padj=9.66E-09; FKBP5 d12 PSC-ESF monolayer v. PSC-ESF co-culture *padj=0.03331652, d12 PSC-ESF monolayer v. PSC-ESF co-culture decidualized **padj=3.73E-07, PSC-ESF co-culture v. PSC-ESF co-culture decidualized padj=1.48E-40; PTGS1 d12 PSC-ESF monolayer v. PSC-ESF co-culture padj=0.00051017, d12 PSC-ESF monolayer v. PSC-ESF co-culture decidualized **padj=8.13E-12, PSC-ESF co-culture v. PSC-ESF co-culture decidualized *padj=0.04402734). f. Gene expression analyses by qPCR of BMP2 signaling activators NR2F2, HOXA10, and BMP2 in decidualized co-cultures with (+) and without (−) 48 hr treatment of cyclopamine. Expression of NR2F2 (d12 v.− *p=0.0353, n=2) and BMP2 (d12 v.− ns p=0.4096, n=2) are increased in co-culture relative to d12 monolayer PSC-ESF; while expression of HOXA10 is reduced (d12 v.−*p=0.0190, n=2). The presence of cyclopamine decrease co-culture expression of NR2F2 (−v.+*p=0.0321), HOXA10 (−v.+*p=0.0314), and BMP2 (−v+*=0.2699). Data is represented as fold change in e and f; mean±SEM in f.

Figure 6:
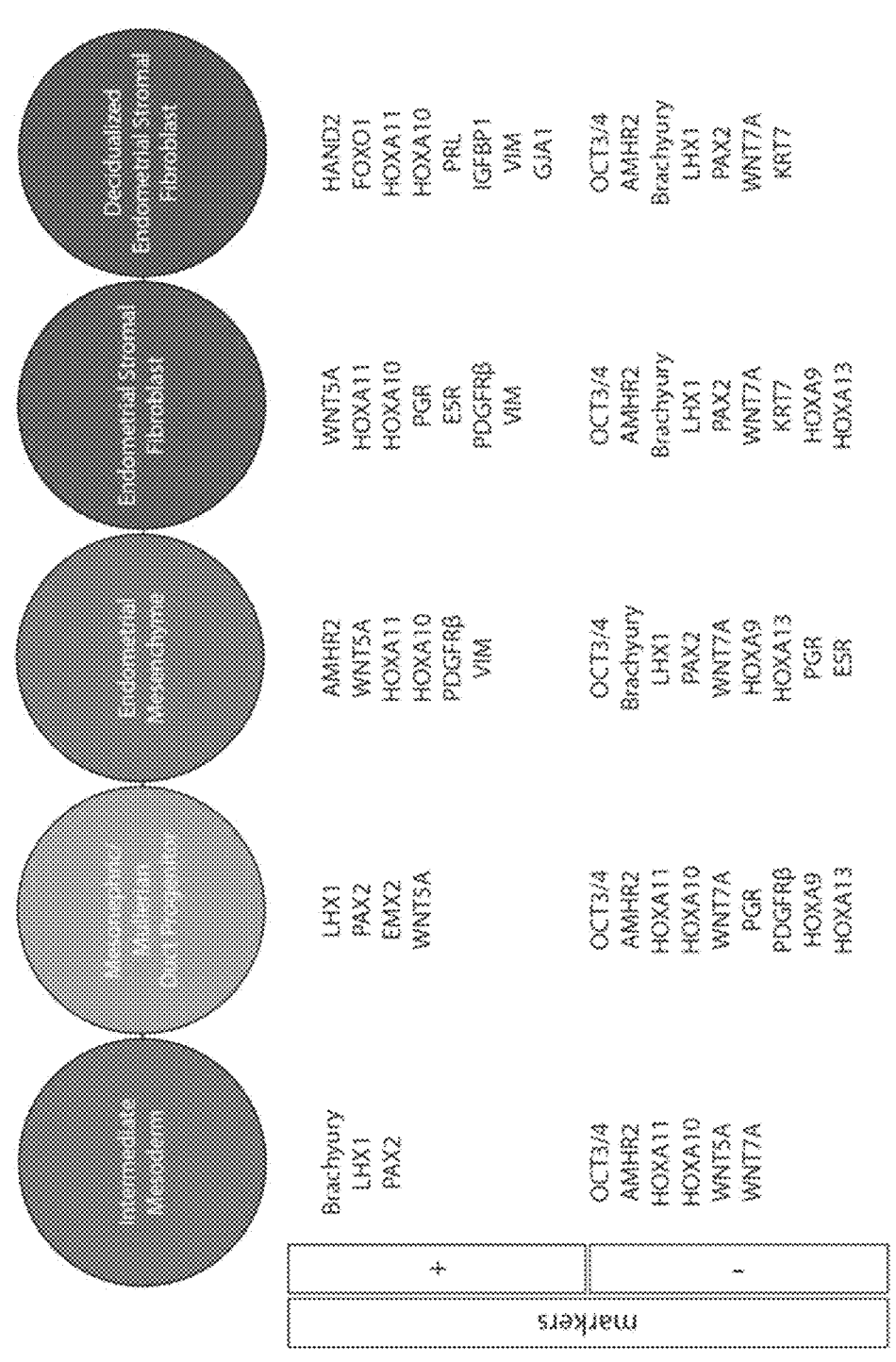

FIG. 6. Overview of developmental stages from pluripotency to decidual endometrial stromal fibroblasts select marker gene expression. Related to FIGS. 1 and 2. Positive and negative markers were selected prospectively and measured throughout protocol development.

FIG. 7a-FIG. 7l. Maturation and maintenance of endometrial mesenchyme progenitors to endometrial stromal fibroblasts. Related to FIG. 2 a. Comparison of different concentrations of CHIR99021 from day 0 to day 4 for IM induction from ESC. At day 4, LHX1 (ns p=0.828, n=2) and PAX2 (ns p=0.6167, n=2) are both highly, but differently induced by both concentrations of CHIR99021. b. However, subsequent treatment with 100 ng/mL WNT7A from day 4 to day 8 only induced high expression of endometrium specific genes HOXA10 (ns=0.0792, n=2) and HOXA11 (ns p=0.3875, n=2) in the 8 uM condition. c. Expression of mesenchymal cell marker vimentin (VIM, red) expression at day 12 confirmed the maintenance of stromal cell fate. d. Quantitative PCR (qPCR) analysis of mRNA expression of HOX genes demonstrating maintenance of region specificity at day 12 n=5. (F (3, 23)=10.63 *P=0.0001, Tukey's posthoc HOXA9 vs HOXA10, ns p=0.4642; HOXA11 v. HOXA9, *p=0.0006; HOXA13 vs HOXA10 ns p=0.4195; HOXA13 vs HOXA11 *p=0.0003; HOXA13 vs HOXA9, ns p>0.9999; HOXA11 vs HOXA10 ns p=0.0504) e. HOXA10 expression by immunocytochemistry (ICC) at day 12 of differentiation. f. Schematic of freeze-thaw experiment timeline. PSC-ESP at day 8 were cryofrozen for storage in liquid nitrogen. Thawed cells were subsequently matured to PSC-ESF by treatment with 10 ng/mL BMP2 and 10 nM $E_2$ for 4 days. g. Expression of Ki67 (red), VIM (green), and HOXA10 (green) by ICC in PSC-ESF matured from freeze-thawed PSC-ESP. Low expression of AMHR2 (red) was observed after thawing, similar to freshly derived PSC-ESF at day 12 of differentiation. h. Expression of adult endometrial mesenchymal stem cell (eMSC) marker SUSD2 at day 0 (n=4), 4 (n=4), 8 (n=3), and 12 (n=4) of differentiation as measured by RNA-sequencing, shown in transcripts per million (TPM). i. qPCR mRNA expression analysis confirms a gain of hormone receptor, PGR, between day 8 and day 12. (day 0 vs day 12 p<0.0001, n=6; day 8 vs day 12 *p=0.000, n=5). j. Schematic illustrating decidualization treatment 3 passages after initial derivation of PSC-ESF. k. Bright phase images of passaged cells showing a fibroblast morphology in vehicle treated cells and a cuboidal morphology after CEP treatment. 1. qPCR data showing an increase in PRL (ESF vs CEP p=0.0055, n=2), IGFBP1 (ESF vs CEP ns=0.1019, n=2), and FOXO1 (ESF vs. CEP *p=0.000'7, n=2) gene expression in CEP treated passaged PSC-ESF. Data is represented as mean±SEM in a, b, d, h, i and 1. Scale bars, 50 µm in c, e, and g, 100 µm in k.

FIG. 8a-FIG. 8h. Primary stromal and mesenchymal cells do no co-culture with EEO while PSC-ESF expands while in co-culture and promote maturation of the epithelium after decidualization. Related to FIG. 3 a. Characterization of EEO from term placenta for EpCAM (red), glandular marker FOXA2 (green), cell cycle maker Ki67 (red), and progesterone receptor PR (green).b. Schematic of co-culture protocol for monolayer primary cells and EEO. c. Bright phase image of EEOs after 10 days of co-culture with: PSC-ESF, primary ESF, primary bone marrow derived mesenchymal stem cells (BM-MSC), primary dermal stromal fibroblasts. Only PSC-ESF clustered around the EEO. d. EEO when cultured alone with the treatment paradigm described in FIG. 3c. e. Immunocytochemical analysis of mesenchyme marker PDGFRβ+(green) and epithelial cell marker keratin 7 (KRT7, magenta) in EEO alone, co-cultures prior to decidualization, and co-cultures after 16 days of CEP treatment. f. Quantification of WNT5A transcript, as measured by fluorescent puncta per cell after RNAscope assay, demonstrates that WNT5A is preferentially expressed in stromal cells of co-cultured organoids. (***p-value=0.0005, n=5) g. Epithelial FOXA2 (green) and stromal HOXA11 (red) double staining. The stromal-epithelial cell interface is represented by the perforated line. h. Ciliated epithelial cells, marked by acetylated a-tubulin (magenta) at the apical surface, is present with co-culture and the number increases after decidualization treatment for 14 days. Data is represented as mean±SEM in f. Scale bar, 100 µm. c and d, 50 µm in a, e, g, and h. inset 25 µm in h.

FIG. 9a-FIG. 9h. Hormone and vehicle response after Cycle 1 and Cycle 2. Related to FIG. 4 a. Proliferative marker phosphorylated-Histone H3 (green) showing a greater number of PSC-ESF in M phase during the hormone withdrawal phase than at the end of Cycle 1 and Cycle 2 hormone treatment. E-Cadherin ECAD (red) specifically stains the epithelial cell population and is unchanged in response to hormone treatment. b. Cleaved Caspase 3 (green), showing increased PSC-ESF and epithelial cells undergoing apoptosis at the end of Cycle 1 and Cycle 2 in comparison to during hormone withdrawal. c. Quantification of cleaved Caspase stromal and epithelial cells across hormone treatment. Stroma: F (2,5)=3.425 ns p-value=0.1156. Epithelium: F (2,6)=2.239 ns p=0.1878. Cycle 1, n=2; withdrawal, n=3; Cycle 2, n=3. d. Immunocytochemistry showing low expression of decidualization associated cell markers (FOXO1, PR, HOXA11, HAND2, IGFBP1) and epithelial cells markers (KRT7, EpCAM) with vehicle treatment at matched time points. e. Endometrial-associated biological process gene ontology (GO) terms upregulated by hormone treatment over vehicle enriched in both Cycle 1 PSC-ESF and Cycle 2 PSC-ESF. f. Top 10 gene ontology (GO) terms enriched for by genes upregulated in Cycle 1 only or Cycle 2 only by hormone treatment over vehicle. Data represented as mean±SEM. Scale bars, 100 µm in a, b, and d. Panel g shows FOXA2 expression (within the dashed lines) and HOXA 11 expression (outside the dashed lines). Panel h shows acetylated a-tubulin expression in organoids only; at day 10; at day 26-14 days of CEP; and at day 26 with 14 days of vehicle.

FIG. 10a-FIG. 10f. Decidualization of PSC-ESF/EEO co-culture to Cycle 3. Related to FIG. 5 a. Schematic of hormone treatment paradigm. b. Bright phase image of co-culture at the end of Cycle 3, 78 days in culture. c. Expression of markers of cell proliferation and apoptosis at the end of Cycle 3. d. Quantification of percentage of stromal and epithelial cells positive for Ki67 (Cycle 1 n=4, Cycle 2 n=3, Cycle 3 n=1) and cleaved Caspase 3 (Cycle 1 n=4, Cycle 2 n=3, Cycle 3 n=1) across all 3 hormone cycles. e. Expression of endometrial stromal and glandular epithelial cell markers VIM (red), HOXA11 (green) KRT7 (magenta) and FOXA2 (red) at the end of Cycle 3. f. Expression of decidualization markers IGFBP1 (red), HAND2 (green), Connexin 43 (green), and cilia as marked by acetylated a-tubulin along the apical surface. Data represented as mean±SEM in d. Scale bars, 50 µm in e, and f.

FIG. 11a-FIG. 11d. Preparation of PSC-ESF for purification and collection by FACS for RNA isolation. Related to FIG. 5 a. Schematic of viral transduction and co-culture. b. Timeline of cell collection by FACS used for RNA-sequencing. c. Representative brightfield phase and red fluorescence (PSC-ESF) images from the end of Cycle 1. d. Representative FACS plot from the end of Cycle 2 showing separation of (red) PE+ and PE− cells. Only PE+ cells were collected for RNA isolation. Scale bar, 500 µm FIG. 12*a*-FIG. 12*d*. Hedgehog signaling and other pathways uniquely upregulated by decidualized co-culture PSC-ESF and not decidualized primary ESF enrich for pathways relevant to decidualization. Related to FIG. 5 *a*. Schematic of treatment paradigm for inhibition of Hedgehog signaling. Co-cultures were cultured in vehicle treatment media with either 10 uM cyclopamine (+) or vehicle (EtOH, −). After 48 h co-cultures were harvested for RNA and qPCR analysis. b. Gene expression of direct downstream mediators of IHH signaling: GLI1 and GLI2. GLI1 is significantly upregulated in expression in co-cultures and significantly downregulated by cyclopamine treatment (d12 v.− **p=value<0.0001; −v.+**p-value<0.0001, n=2). GLI2 was similarly regulated without statistical significance. (d12 v.−ns p-value=0.0953; −v.+ns p-value−v.+p-value=0.2661). c. A list of top transcription factor (TF) binding sites shared by genes significantly upregulated in decidualized co-cultured PSC-ESF over decidualized monolayer ESF control from the ChIP Enrichment Analysis (ChEA) and Encyclopedia of DNA Element (ENCODE) database. (Lachman, A., 2010; ENCODE Project Consortium, 2011) d. Top 10 pathways enriched in decidualized co-cultured PSC-ESF over decidualized monolayer ESF as analyzed by the integrated Bioplanet 2019 platform. Both enrichment analyses done using Enrichr with a 2-fold cutoff ((http://amp.pharm.mssm.edu/Enrichr/).

Figures 13A, 13B:
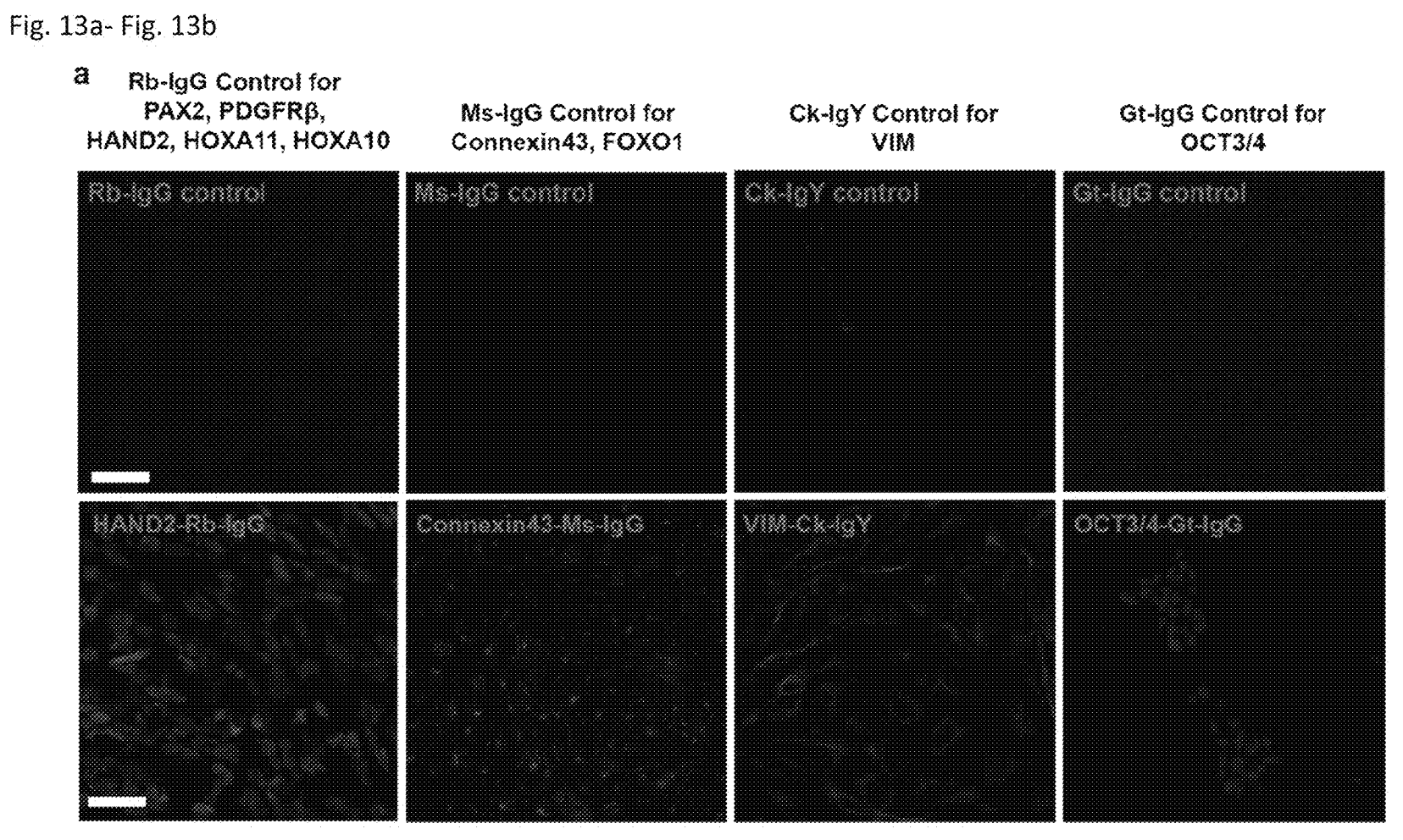

FIG. 13*a*-FIG. 13 *b*. Isotype controls for monolayer and co-culture immunocytochemical analysis. Related to FIGS. 1, 2, 3, and 4. a. ICC of cells along the PSC-ESF differentiation protocol stained with cell type-specific antibodies and their respective species-specific isotype controls. b. ICC of co-culture organoids stained with species-specific isotype controls for listed epithelial and stromal cell markers of respective species. The stromal-epithelial cell interface is represented by the perforated line. Isotype control concentrations were determined by the highest concentration of antibody used for each species and are available in Table 2. Scale bars, 50 μm in a and b.

DETAILED DESCRIPTION

Terminology

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

A range includes each individual member. Thus, for example, a group having 1-3 members refers to groups having 1, 2, or 3 members.

As used herein, "about" means within 5% of a stated concentration range, density, temperature, time frame, etc.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

As used herein, the term "stem cell" refers to cells that are undifferentiated or partially differentiated cells that can differentiate into various types of cells and proliferate indefinitely to produce more of the same stem cell. They are the earliest type of cell in a cell lineage. Stem cells are found in both embryonic and adult organisms, but may have slightly different properties in each. They are usually distinguished from progenitor cells, which cannot divide indefinitely, and precursor or blast cells, which are usually committed to differentiating into one cell type.

As used herein, the term "pluripotent" stem cell refers to a cell that is not capable of growing into an entire organism, but is capable of giving rise to cell types originating from all three germ layers, i.e., mesoderm, endoderm, and ectoderm, and may be capable of giving rise to all cell types of an organism. Pluripotency can be a feature of the cell per see, e.g. in certain stem cells, or it can be induced artificially. Examples of pluripotent stem cells include, but are not limited to, embryonic stem cells (ES), embryonic stem cells derived from a cloned embryo obtained by nuclear transplantation (ntES), spermatogonial stem cells ("GS cells"), embryonic germ cells ("EG cells"), induced pluripotent stem cells (iPS) and multipotent cells derived from cultured fibroblasts. In some embodiments, ES cells and/or iPS cells such as human iPS cells are used in the methods and compositions disclosed herein.

As used herein, the term "embryonic stem cell" refers to cells that are totipotent and derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Embryonic stem cells can be obtained directly from suitable tissue, including, but not limited to human tissue, or from established embryonic cell lines. In one embodiment, embryonic stem cells are obtained as described by Thomson et al. (U.S. Pat. Nos. 5,843,780 and 6,200,806; Science 282:1145, 1998; Curr. Top. Dev. Biol. 38:133 ff, 1998; Proc. Natl. Acad. Sci. U.S.A. 92:7844, 1995 which are incorporated by reference herein in their entirety).

As used herein, the terms "induced pluripotent stem cell" or "iPSC", which are used interchangeably herein, refer to pluripotent cells derived from differentiated cells. For example, iPSCs can be obtained by overexpression of transcription factors such as Oct4, Sox2, c-Myc and Klf4 according to the methods described in Takahashi et al. (Cell, 126: 663-676, 2006). Other methods for producing iPSCs are described, for example, in Takahashi et al. Cell, 131: 861-872, 2007 and Nakagawa et al. Nat. Biotechnol. 26: 101-106, 2008; which are incorporated herein by reference herein in their entirety.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be susceptible to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. The subject therapy will desirably be administered during the symptomatic stage of the disease, and in some cases after the symptomatic stage of the disease.

Technology Overview

Treatments for endometrial and reproductive diseases are lacking due to a limitation of models to effectively characterize drug action and effectiveness to safely enroll patients and vulnerable populations for clinical trials.

Differentiation protocols from pluripotent stem cells to endometrial stromal fibroblasts (ESF) have been described but result in low purity and low yield in embryoids and have not been successful in relatively pure monolayer cultures. Endometrial co-cultures have been reported using primary ESF and endometrial epithelial cells. The two technologies have never been combined and the co-culture, even with primary cells, has never been described or characterized to be long-term. By way of example, the inventors have demonstrated the induced PSC-ESF cells can be maintained at the precursor stage for up to 3 passages, approximately one month. Once differentiated, PSC-ESF containing stromal cell/epithelial organoids can be maintained up to 3 months with multiple passages.

Disclosed herein is a novel technology to overcome this barrier to drug development. The disclosed technology includes a method to differentiate induced pluripotent stem cells (iPSC) from patients to endometrial stromal cells (PSC-ESF), the majority cell type of the endometrium. Further, we have described a multicellular organoid model using PSC-ESF and epithelial organoids derived from term placenta. This model is able to functionally respond to hormone treatment and withdrawal of a hormone treatment which induce decidualization, thus allowing the study of drug effects on the entire endometrial cycle. It also will enable examination of drug effects on interactions of the model with trophoblastic cells, thus providing a potential screen for drug effects in human pregnancy. In addition to the uses of the protocol for drug development and screening, the protocol can be utilized to generate cells for cell replacement therapies, for use as a vehicle for cellular gene therapy, and/or as a vehicle for targeted drug delivery to the female reproductive tract or in diseases such as endometriosis where the target cells reside outside of the reproductive tract.

Additional applications and advantages of the disclosed technology include, but is not limited to: drug screen for effects on human endometrium; drug screen for effects on the process of implantation on the human endometrium/decidua; testing for drug processing by human endometrium/decidua for subsequent effects on placenta/fetus; provision of cells for cell replacement therapies or as a vehicle for gene therapy or drug delivery. In some embodiments, the present technology provides a model comprising human cells, and can eliminate the need for currently inadequate animal (e.g., rodent) models. Moreover, the disclosed methods and compositions provide a model comprising two cell types of the human endometrium, and the model is cyclical in that it is responsive to hormone treatment, withdrawal, and retreatment, thus enabling the study of the endometrium across an entire hormone cycle.

Accordingly, the present technology fills an unmet need for human models of the endometrium that can be established from diseased or healthy patient backgrounds (iPSC and term placenta) and that can be used to study endometrial responses and cell behavior across hormone cycles and drug treatment. The present technology provides value, at least because it offers an additional model for studying and screening disease and drugs for human endometrium/decidua and implantation, thus enabling drug development for women and pregnant women.

Cells

While in some embodiments, human cells are preferred, the cells to be used in the methods and compositions related to cell differentiation and tissue constructs of the present disclosure are not limited to cells from human sources, and the methods of treatment, and drug screening are not limited to human subjects. Cells from other mammalian species including, but not limited to, equine, canine, porcine, bovine, feline, caprine, murine, and ovine sources can be used. Cell donors may vary in development and age. Cells can be derived from donor tissues of embryos, neonates, or older individuals including adults.

In the methods and compositions disclosed herein, pluripotent stem cells are of female origin (XX).

In some embodiments, the pluripotent stem cells (PSCs) used in the methods and compositions disclosed herein are induced pluripotent stem cells (iPSCs). In some embodiments, the iPSC are derived from a subject suffering from, or diagnosed with a disease or condition. In some embodiments, the cells include one more genetic mutations known to cause a medical disease or condition when the genetic mutation is present in a human subject. In some embodiments, the disease or condition affects the endometrium.

In some embodiments, other types of PSC are used, such as, but not limited to embryonic stem cells.

In some embodiments, the pluripotent stem cells (PSCs) used in the methods and compositions disclosed herein have been genetically engineered or genetically modified. In some embodiments, the PSC have been genetically modified to comprise one or more mutations that are known to cause or are suspected to cause a disease or condition.

In some embodiments, the PSCs are modified to produce recombinant cell products, growth factors, hormones, peptides, or proteins (e.g., including but not limited to detectable reporter proteins, and therapeutic proteins) for a continuous amount of time or as needed when biologically, chemically, or thermally signaled due to the conditions present in culture or in a transplant environment. Procedures for obtaining recombinant or genetically modified cells are generally known in the art.

In some embodiments, PSCs are modified to express a detectable reporter gene (e.g., a fluorescent reporter gene, a reporter gene for colorimetric detection). By of example, such cells can be used to derive endometrial organoids or tissues having, for example, fluorescently labeled structures, or cell types. Such organoids would be advantageous to rapidly assess cell lineage, response, condition, reaction, behavior, etc. for example, during drug testing. In some embodiments, it may be advantageous to obtain PSCs comprising a dual reporter system in which different cell types are labeled with different reporter proteins for rapid identification and cell tracking.

Cell Culture Tissue/Organoid Culture Considerations

Disclosed herein are methods for obtaining endometrial stromal fibroblast cells (PSC-ESF) from pluripotent stem cells, such as induced pluripotent stem cells. The resulting PSC-ESF decidualized in monolayer and are able co-culture with EEO and respond to hormone in co-culture. The present disclosure also provides methods of obtaining a three-dimensional, multilayered endometrial tissue composition using the PSC-ESF.

In some embodiments, the differentiation protocol comprises the following steps: (a) culturing pluripotent stem cells (PSCs) with a first Wnt/β-catenin agonist for about 4 days; (b) culturing the cells of (a) with a second Wnt/β-catenin agonist for about 4 days; (c) culturing the cells of (b) with Bone Morphogenetic Protein 2 (BMP-2) and β-estradiol, or culturing the cell with mycophenolic acid (MPA) for about 4 days; wherein the cultured cells of (c) comprise PSC-ESF cells. In some embodiments, the method further comprises combining dissociated cells from endometrial epithelial organoids (EEO), and dissociated PSC-ESF in a porous substrate comprising extracellular matrix components; culturing the combined cells in the porous substrate for about 10 days, wherein the combined cells self-assemble to form a three-dimensional human endometrial tissue comprising an outer layer of PSC-ESF and an inner layer of epithelial cells, and wherein the three-dimensional human endometrial tissue is responsive to cyclic hormone treatment.

In some embodiments, to begin a differentiation protocol of the present technology, a confluent culture of pluripotent stem cells can be chemically, enzymatically or mechanically dissociated from a surface, such as Matrigel® or a chemically defined substrate (e.g., a hydrogel), into clumps, aggregates, or single cells.

In some embodiments, pluripotent stem cells or stem cell aggregates are cultured in the presence of a Rho kinase (ROCK) inhibitor. Kinase inhibitors, such as ROCK inhibitors, are known to protect single cells and small aggregates of cells. See, e.g., U.S. Patent Application Publication No 2008/0171385, incorporated herein by reference as if set forth in its entirety; and Watanabe K, et al., "A ROCK inhibitor permits survival of dissociated human embryonic stem cells," Nat. Biotechnol. 25:681-686 (2007). In some embodiments, ROCK inhibitors increase pluripotent cell survival on chemically defined surfaces. Exemplary ROCK inhibitors suitable for use herein include, but are not limited to: (S)-(+)-2-methyl-1-[(4-methyl-5-isoquinolinyl) sulfonyl] homopiperazine dihydrochloride (informal name: H-1152), 1-(5-isoquinolinesulfonyl) piperazine hydrochloride (informal name: HA-100), 1-(5-isoquinolinesulfonyl)-2-methy 1 piperazine (informal name: H-7), 1-(5-isoquinolinesulfo-nyl)-3-methy 1 piperazine (informal name: iso H-7), N-2-(methylamino) ethyl-5-isoquinoline-sulfonamide dihydro-chloride (informal name: H-8), N-(2-aminoethyl)-5-isoquinolinesulphonamide dihydrochloride (informal name:

H-9), N-[2-p-bromocinnamylamino)ethyl]-5-isoquinoline-sulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methy 1-4-glycyl-1-(4-methylisoqui-nolinyl-5-sulfonyl) homopiperazine dihydrochloride (informal name: glycyl H-1152) and (+)-(R)-trans-4-(1-amino-ethyl)-N-(4-pyridyl) cyclohexanecarboxamide dihydrochloride (informal name: Y-27632). The kinase inhibitor can be provided at a concentration sufficiently high that the cells survive and remain attached to the surface. An inhibitor concentration between about 3 µM to about 15 µM, or about 5 µM to about 10 µm can be suitable. At lower concentrations, or when no ROCK inhibitor is provided, undifferentiated cells typically detach, while differentiated cells remain attached to the defined surface.

In some embodiments, cells are cultured with a first and a second Wnt/β-catenin agonist. In some embodiments, the first and the second Wnt/β-catenin agonists are the same. In some embodiments, the first and the second Wnt/β-catenin agonists are different. In some embodiments, the Wnt/β-catenin agonist comprises an inhibitor of GSK3. In some embodiments, the inhibitor of GSK3 is selected from CHIR99021, lithium chloride (Li Cl), 6-bromoindirubin-3'-oxime (BIO), or recombinant WNT protein, such as human WNT7A, or a combination thereof. In some embodiments, cells are cultured for about 3 days, about 4 days, or about 5 days in the presence of a first Wnt/β-catenin agonist. In some embodiments, the cells are cultured for about 4 days in the presence of a first Wnt/β-catenin agonist. In some embodiments, cells are cultured for about 3 days, about 4 days, or about 5 days in the presence of a second Wnt/β-catenin agonist. In some embodiments, the cells are cultured for about 4 days in the presence of a second Wnt/β-catenin agonist. In some embodiments, the first Wnt/β-catenin agonist comprises CHIR99021. In some embodiments, the second Wnt/β-catenin agonist comprises recombinant human WNT7A.

In some embodiments, the first Wnt/β-catenin agonist is provided at about 1-20 µM, 2-15 µM, 3-10 µM, or at about 5, 6, 7, 8, or 9 µM. In some embodiments, the first Wnt/β-catenin agonist is provided at about 8 µM. In some embodiments, the first Wnt/β-catenin agonist comprises CHIR99021.

In some embodiments, the second Wnt/β-catenin agonist is provided at about 10-200 ng/mL, about 20-180 ng/mL, about 50-150 ng/mL, or about 60, 70, 80, 90, 100, 110, 120, 130 or 140 ng/mL. In some embodiments, the second Wnt/β-catenin agonist is provided at about 100 ng/mL. In some embodiments, the second Wnt/β-catenin agonist comprises human recombinant WNT7A.

In some embodiments, after culturing with a first and a second Wnt/β-catenin agonist, cells are cultured with a Bone Morphogenetic Protein (BMP). In some embodiments, the BMP comprises BMP-2 or BMP-4. As is known in the art, BMP-4 and BMP-2 share significant protein sequence similarity and phylogenetically cluster together. BMP-2 and BMP-4 also bind BMP receptors in the same sequence and result in the same heterodimers (Wang et al., 2014). In some embodiments, cells are cultured for about 3 days, about 4 days, or about 5 days in the presence of a BMP. In some embodiments, the cells are cultured for about 4 days in the presence of a BMP. In some embodiments, BMP comprises BMP-2. In some embodiment, BMP comprises BMP-4.

In some embodiments, the BMP is provided at about 1-20 ng/mL, about 2-18 ng/mL, about 3-15 ng/mL, or about 4, 5, 6, 7, 8, 9, 10, 11, 12, 13, or about 14 ng/mL. In some embodiments, the BMP is provided at about 10 ng/mL. In some embodiments, the BMP comprises BMP-2. In some embodiment, BMP comprises BMP-4.

In some embodiments, after culturing with a first and a second Wnt/β-catenin agonist, cells are cultured with an estrogen, such as estradiol (E$_2$) (also known as β-estradiol, and used interchangeably herein with E$_2$), or diethstilbestrol a synthetic form of the human female estrogen, which has been used on primary hESF in vitro (see. e.g, Gellersen and Brosens, 2014). In some embodiments, cells are cultured for about 3 days, about 4 days, or about 5 days in the presence of β-estradiol. In some embodiments, the cells are cultured for about 4 days in the presence of β-estradiol.

In some embodiments, the β-estradiol is provided at about 1-20 nM, 2-18 nM, 3-15 nM, or at about 4, 5, 6, 7, 8, 9, 10, 11, 12, 13, or about 14 nM. In some embodiments, β-estradiol is provided at about 10 nM.

In some embodiments, after culturing with a first and a second Wnt/β-catenin agonist, cells are culture with a combination of a BMP and β-estradiol. In some embodiments, cells are cultured for about 3 days, about 4 days, or about 5 days in the presence of a BMP and β-estradiol. In some embodiments, the cells are cultured for about 4 days in the presence of a BMP and β-estradiol.

In some embodiments, after culturing with a first and a second Wnt/β-catenin agonist, cells are cultured in the presence of mycophenolic acid (MPA). In some embodiments, MPA is provided at about 0.1 to about 10 μM, about 0.5-5 μM or about 0.6, 0.7, 0.8, 0.9, 1.0, 1.1, 1.2, 1.5, 1.4, 1.5, 2, 3, 4, or about 5 μM. In some embodiments, MPA is provided at about 1.0 μm. In some embodiments, cells are cultured for about 3 days, about 4 days, or about 5 days in the presence of a MPA. In some embodiments, the cells are cultured for about 4 days in the presence of MPA.

In some embodiments, cells, organoids, co-cultures, or other three-dimensional, multilayered human endometrial tissue composition of the present disclosure are treated to induce decidualization. In some embodiments, decidualization is induced by culturing with estradiol (E$_2$), followed by culturing with E$_2$, 8-bromoadenosine-cAMP (cAMP), and medroxyprogesterone 17-acetate (MPA).

In some embodiments, cells, organoids, co-cultures or tissue compositions are cultured with E$_2$ for about 1 day, about 2 days, about 3 days, or about 4 days. In some embodiments, cells, organoids, co-cultures or tissue compositions are cultured with E$_2$ for about 2 days. In some embodiments, cells, organoids, co-cultures or tissue compositions are then cultured with E$_2$, cAMP and MPA for about 8, 9, 10, 11, 12, 13, 14, 15, or about 16 days. In some embodiments, cells, organoids, co-cultures, or tissue compositions are cultured for about 14 days.

In some embodiments, the E$_2$ concentration is about 1-20 nM, 2-18 nM, 3-15 nM, or at about 4, 5, 6, 7, 8, 9, 10, 11, 12, 13, or about 14 nM. In some embodiments, E$_2$ is provided at about 10 nM. In some embodiments, cAMP is provide at about 0.1-1.0 mM, about 0.2, 0.3, 0.4, 0.5, 0.6, 0.7, 0.8 or 0.9 mM. In some embodiments, the cAMP is provided at about 0.5 mM. In some embodiments, MPA is provided at about 0.5-2.0 μM, about 0.7-1.5 μM or about 0.8, 0.69, 1.0, 1.1, 1.2, 1.3 or about 1.4 μm. In some embodiments, MPA is provided at about 1.0 μM.

Exemplary Porous Substrates

In recent years, polyethylene glycol (PEG)-based hydrogels cross-linked with defined concentrations of extracellular matrix proteins have become a chemically-defined alternative to matrices such as Matrigel®. In exemplary embodiments, the methods provided herein can comprise culturing, embedding, or encapsulation of cells in a chemically defined, porous biomaterial such as a hydrogel. The term "hydrogel" refers to a highly hydrated porous material comprising synthetic or biological components formed when an organic polymer (natural or synthetic) is cross-linked via covalent, ionic, or hydrogen bonds to create a 3D open-lattice structure that entraps water molecules to form a gel. Hydrogels appropriate for constructing 3D endometrial organoids of the present disclosure include, without limitation, synthetic hydrogels, bioactive hydrogels, biocompatible hydrogels, cytocompatible hydrogels, chemically defined hydrogels, chemically-defined synthetic hydrogels, and proteolytically degradable hydrogels. As used herein, "bioactive" is intended to indicate the ability to facilitate a cellular or tissue response, such as differentiation of a pluripotent stem cell, promotion of cellular attachment, promotion of cell self-assembly, and promotion of cell-cell interactions. As used herein, the term "biocompatible" refers to the ability of a polymer or hydrogel to perform as a substrate that will support cellular activity, including the facilitation of molecular and mechanical signaling systems, in order to permit proper cell self-assembly or cellular function such as tissue formation, production of soluble bioactive molecules (e.g., growth factors), specific cell behaviors such as migration and proliferation. In some cases, "biocompatibility" means the absence of components having cell- or tissue-damaging effects. As used herein, the term "cytocompatible" means the hydrogel material is substantially non-cytotoxic and produces no, or essentially no, cytotoxic degradation products, while the term "proteolytically degradable" as used herein means that the crosslinked backbone can be cleaved enzymatically or nonenzymatically to break down the scaffold network As used herein, the term "chemically defined" means that the identity and quantity of each component of a composition (e.g., a hydrogel) is known. An important goal in the fields of pluripotent stem cell culture and directed differentiation of pluripotent stem cells is to develop culture materials and culture media that provide improved performance consistency and reproducibility. In some cases, a chemically defined hydrogel for use in deriving a endometrial organoids as disclosed herein comprises a minimal number of defined components/ingredients.

Exemplary Tissue Support Matrices

In some embodiments, a 3D endometrial tissue construct is provided with or incorporated onto or into a support structure for construction of a new tissue. Support structures can be scaffolds, meshes, solid supports, tubes, porous structures, and/or a hydrogel. A support structure can be a tissue engineering scaffold, matrix, or material forming a matrix. Support structures can be biodegradable or non-biodegradable, in whole or in part. As used herein, the term "biodegradable" means that a material degrades or breaks down into its component subunits by a biochemical process. The support can be formed of a natural or synthetic polymer, metal such as titanium, bone or hydroxyapatite, or a ceramic. Natural polymers include, without limitation, collagen, hyaluronic acid, polysaccharides, and glycosaminoglycans. Synthetic polymers include, without limitation, polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters.

Exemplary Culture Media and Culture Conditions

The methods disclosed herein employ cell culture methods known in the art. For example, PSCs maintained using commercially available cell culture techniques can be used for this differentiation protocol (see e.g., Dakhore et al., 2018, herein incorporated by reference in its entirety) By way of example, Advanced RPMI (Gibco) culture media was used for differentiation. However, other commercially available culture media containing amino acids, vitamins, inorganic salts, and proteins (albumin, transferrin, and insulin) will also work, https://www.thermofisher. com/order/catalog/product/12633012#/12633012). Commercially available media options are available and are well known to the skilled artisan.

Biomarker Detection

Any appropriate method can be used to detect expression of biological markers characteristic of the cell types described herein. For example, the presence or absence of one or more biological markers can be detected using, for example, Western blotting, ELISA assays and related antibody techniques, RNA sequencing, immunohistochemistry, polymerase chain reaction, qRT-PCR, or other technique that detects or measures gene expression (RNA or protein). Quantitative methods for evaluating expression of markers at the protein level in cell populations are also known in the art. For example, antibody related techniques such as ELISA-type assays, Western blotting, flow cytometry can be used to determine the fraction of cells in a given cell population that express or do not express biological markers of interest. Differentiated cell identity is also associated with downregulation of pluripotency markers such as NANOG and OCT4.

Disease and Conditions

In some embodiments, the present technology is useful to screen for drugs, to identify those with likely therapeutic benefit in the treatment of diseases or medical conditions that affect the endometrium. In addition, the present technology is useful for developing models of diseases and conditions. By way of example but not by way of limitation, disease and medical conditions include endometriosis, endometrial cancer, amenorrhea, implantation failure.

Therapeutic Applications of the PSC-ESF and Engineered Endometrial Tissue Compositions In some embodiments, the PSC-ESF cells, or the engineered endometrial tissue compositions of the present disclosure may be used for cell or tissue replacement therapies or as a vehicles for gene therapy or drug delivery. By way of example, in some embodiments, the cells and/or tissues of the present technology are administered to a subject, (e.g., transplanted into a subject), to replace and/or treat diseased or damaged tissue.

EXEMPLARY EMBODIMENTS

Presented below are non-limiting, exemplary embodiments of the present technology.

1. A method of obtaining human endometrial stromal fibroblasts (PSC-ESF), comprising: a) culturing pluripotent stem cells (PSCs) with a first Wnt/β-catenin agonist for about 4 days; (b) culturing the cells of (a) with a second Wnt/β-catenin agonist for about 4 days; (c) culturing the cells of (b) with Bone Morphogenetic Protein 2 (BMP-2) and β-estradiol for about 4 days; wherein the cultured cells of (c) comprise PSC-ESF cells.

2. The method of embodiment 1, wherein the first Wnt/β-catenin agonist comprises an inhibitor of GSK3.

3. The method of embodiment 2, wherein the inhibitor of GSK3 is one or more selected from CHIR99021, lithium chloride (Li Cl), and 6-bromoindirubin-3'-oxime (BIO).

4. The method of embodiment 3, wherein the inhibitor of GSK3 is CHIR99021.

5. The method of any of the previous embodiment, wherein the second Wnt/β-catenin agonist comprises a Wnt protein.

6. The method of embodiment 5, wherein the Wnt protein comprises WNT7 protein.

7. The method of embodiment 1, wherein the cells of (b) are optionally frozen prior to continuing to step (c).

8. The method of embodiment 1, wherein the pluripotent stem cells are induced pluripotent stem cells (iPSCs).

9. The method of embodiment 1, wherein the first Wnt/β-catenin agonist is CHIR99021, and the second Wnt/β-catenin agonist is WNT7 protein.

10. The method of embodiment 1, wherein the cells of (c) express progesterone receptor (PR), estrogen receptor (ESR), WNT5, and platelet derived growth factor receptor beta (PDGFRβ).

11. The method of embodiment 1, wherein the PSCs comprise genetically modified cells.

12. The method of embodiment 11, wherein the PSC are genetically modified to express a selectable marker.

13. The method of embodiment 1, wherein the PSCs comprise a genetic mutation known to cause a medical disease or condition when the mutation is present in a human subject.

14. The method of embodiment 1, wherein the PSCs are derived from a subject suffering from or diagnosed with a disease or disorder that affects the endometrium.

15. The method of embodiment 1, wherein the PSCs are induced PSCs (iPSCs).

16. The method of embodiment 1, wherein the cells of (a), (b), and (c) comprise a monolayer.

17. A method of obtaining a three-dimensional, multilayered human endometrial tissue composition responsive to cyclic hormone treatment, comprising: (a) combining dissociated cells from endometrial epithelial organoids (EEO), and dissociated PSC-ESF in a porous substrate comprising extracellular matrix components; (b) culturing the combined cells in the porous substrate for about 10 days, wherein the combined cells self-assemble to form a three-dimensional human endometrial tissue comprising an outer layer of PSC-ESF and an inner layer of epithelial cells, and wherein the three-dimensional human endometrial tissue is responsive to cyclic hormone treatment.

18. The method of embodiment 17, wherein the EEOs are derived from decidual glands harvested from term postpartum placenta, and wherein the EEO cells express EpCAM, FOXA2, Ki67 and PR.

19. The method of embodiment 17, wherein the PSC-ESF are derived according to the method of embodiment 1.

20. The method of embodiment 17, wherein the porous substrate comprises a semi-solid culture medium.

21. The method of embodiment 20, wherein the porous substrate comprises a three-dimensional (3D) porous biomaterial.

22. The method of embodiment 21, wherein the 3D porous biomaterial is a chemically defined hydrogel.

23. The method of embodiment 17, wherein the porous substrate comprises Matrigel.

24. The method of embodiment 17, wherein the combined cells of (b) are cultured in the porous substrate in organoid expansion media (ExM).

25. The method of embodiment 17, wherein outer layer of PSC-ESF and an inner layer of epithelial cells are in direct contact.

26. The method of embodiment 17, wherein the outer layer of PSC-ESF cells interface with the inner layer of epithelial cells along the Laminin+ basolateral surface of the epithelial cells.

27. The method of embodiment 17, wherein the cells from endometrial epithelial organoids (EEO), the PSC-ESFs or both comprise genetically modified cells.

28. The method of embodiment 17, wherein the cells from endometrial epithelial organoids (EEO), the PSC-ESFs or both comprise a genetic mutation known to cause a medical disease or condition when the genetic mutation is present in a human subject.

29. The method of embodiment 17, wherein the cells from endometrial epithelial organoids (EEO), the PSC-ESFs, or both are derived from a subject suffering from or diagnosed with a disease or disorder that affects the endometrium.

30. An engineered, three-dimensional, multilayered human endometrial tissue composition comprising an outer layer of PSC-ESF and an inner layer of epithelial cells, wherein outer layer of PSC-ESF and an inner layer of epithelial cells are in direct contact, and wherein the outer layer of PSC-ESF cells interface with the inner layer of epithelial cells along the Laminin+ basolateral surface of the epithelial cells.

31. The engineered endometrial tissue composition of embodiment 30, further comprising a scaffold.

32. The engineered endometrial tissue composition of embodiment 31, wherein the scaffold is biodegradable or bioabsorbable.

33. The engineered endometrial tissue composition of embodiment 32, wherein the scaffold is a synthetic matrix.

34. The engineered endometrial tissue composition of embodiment 30, wherein the composition is capable of viable transplantation and engraftment to a human subject.

35. A method of testing a compound for effects on endometrial tissue, the method comprising: (a) contacting a test compound to a three-dimensional multilayered human endometrial tissue composition of embodiment 30; and (b) detecting an effect of the agent on one or more cell types within the contacted endometrial tissue.

36. The method of embodiment 35, wherein detecting comprises performing a method selected from the group consisting of RNA sequencing, gene expression profiling, transcriptome analysis, and protein expression analysis.

37. The method of embodiment 35, wherein the compound is screened for an effect on gene expression and wherein detecting comprises assaying for differential gene expression relative to an uncontacted endometrial tissue composition.

38. Use of a three-dimensional multilayered endometrial composition of embodiment 30 in a drug discovery screen.

39. A method for modeling decidualization of the human endometrium, comprising: (a) culturing the three-dimensional, multilayered human endometrial tissue composition of embodiment 30 with estradiol ($E_2$) for about 2 days; (b) culturing the cells of (a) with 8-bromoadenosine-cAMP (cAMP), medroxyprogesterone 17-acetate, and $E_2$ for about 14 days; wherein the cells of (b) express prolactin (PRL), forkhead box O1 (FOXO1), insulin growth factor binding protein (IGFBP1), gap junction protein alpha 1 (GJA1), and heart and neural crest derivatives expressed transcript 2 (HAND2).

40. The method of embodiment 39, further comprising: (d) culturing the cells for about 10 days in the absence of cAMP, medroxyprogesterone 17-acetate, and $E_2$; and (e) repeating steps (a) and (b).

EXAMPLES

Described herein are directed monolayer differentiation methods for generating human ESF lineage cells from PSCs. This results in ESF progenitor cells that are capable of self-organizing with primary EEOs from term placenta to form a 3D, hormone responsive cycling model of the human endometrium.

Example 1. Differentiation Protocol Embodiment: Summary

Disclosed herein are methods for obtaining endometrial stromal fibroblast cells from pluripotent stem cells, such as induced pluripotent stem cells. The present disclosure also provides methods of obtaining a three-dimensional, multi-layered endometrial tissue composition. By way of example, but not by way of limitation, a summary of a differentiation protocol directed to obtaining the stromal fibroblast cells, and co-culture protocol directed to obtaining the endometrial tissue model is provided below.

Pluripotent stem cells maintained on Matrigel and mTseR1 (a standard, feeder-free cell culture medium) were dissociated to single-cell level and plated on Matrigel coated plate in mTseR1 with 10 uM Y27632. 24 hrs later, media was changed to a growth factor-free basal media with 8 uM CHIR99021. 4 days later, media was changed with the same basal media supplemented with 100 ng/mL WNT7A. 4 days later, media was changed with the same basal media to one supplemented with 10 ng/mL BMP2 and 10 nM $E_2$. The cells will reach confluence between 10 and 12 days after treatment and at day 12 will be passaged for co-culture. Cultured endometrial epithelial organoids (EEO) will be fragmented by manual titration. The two cells will be mixed together in 20-25 uL of phenol red-free Matrigel and placed in a dome to gelatinize on tissue culture plastic in a 37 C 5% $CO_2$ incubator. Initial media is an expansion media, known in the art, and containing RSPO1, FGF10, EGF, A83-01, Noggin, and HGF. Hormone treatment used 0.5 mM 8-Br-cAMP, 1 uM MPA, and 10 nM $E_2$ in 2% charcoal-stripped FBS, phenol red-free basal media.

REFERENCES

1. Generation of a Three-Dimensional Collagen Scaffold-Based Model of the Human Endometrium; Abbas Y; Interface Focus, 2020.
2. Scaffold-Free Endometrial Organoids Respond to Excess Androgens Associated With Polycystic Ovarian Syndrome; Wiwatpanit T; J Clin Endocrinol Metab, 2020.
DAKHORE, S., NAYER, B. & HASEGAWA, K. 2018. Human Pluripotent Stem Cell Culture: Current Status, Challenges, and Advancement. *Stem Cells Int,* 2018, 7396905.
WANG, R. N., GREEN, J., WANG, Z., DENG, Y., QIAO, M., PEABODY, M., ZHANG, Q., YE, J., YAN, Z., DENDULURI, S., IDOWU, O., LI, M., SHEN, C., HU, A., HAYDON, R. C., KANG, R., MOK, J., LEE, M. J., LUU, H. L. & SHI, L. L. 2014. Bone Morphogenetic Protein (BMP) signaling in development and human diseases. *Genes Dis,* 1, 87-105.

Example 2—Pluripotent Stem Cell Derived Endometrial Stromal Fibroblasts in a Cyclic Hormone Responsive Co-Culture Model of Human Decidua A variety of human diseases and pregnancy related disorders reflect endometrial dysfunction. However, rodent models do not share fundamental biological processes with the human endometrium, such as cyclic menstruation, and no existing human cell cultures recapitulate the cyclic interactions between endometrial stromal and epithelial compartments necessary for decidualization and implantation. Here we report a protocol to differentiate human induced pluripotent stem cells into endometrial stromal fibroblasts (PSC-ESF) that are highly pure and able to decidualize. Co-culture of PSC-ESF with placenta-derived endometrial epithelial cells generated multicellular organoids that were used to examine stromal-epithelial interactions. Co-cultures exhibited specific endometrial markers in the appropriate compartments, organization with cell-polarity, and hormone responsiveness of both cell types. Further, they cyclically responded to hormone withdrawal followed by hormone retreatment, recapitulating a central feature of the human decidua. This advance enables mechanistic studies of the cyclic responses that characterize the human endometrium.

The human endometrium cyclically proliferates, differentiates, and sheds in response to hormones. This cyclic process, also known as spontaneous decidualization, occurs in response to ovulation in the absence of a fertilized oocyte and implantation (Kin et al., 2015). In the event of successful fertilization, implantation of a blastocyst results in further differentiation in response to molecular signaling and cellular invasion by fetal trophectoderm. Many laboratory animal models, such as mice and rats, lack both spontaneous decidualization and the cellular profile and dynamics of human placentation and thus are imperfect models for many of the unique features of the human endometrium (Hemberger et al., 2020).

Human endometrial stromal fibroblasts (hESF) established from patient biopsies have been widely used to understand the process of decidualization. While these primary cells have greatly informed the mechanisms governing hESF function, they have provided only limited knowledge of the factors governing the development of hESF. Numerous studies have demonstrated the presence of a stem cell population in the basalis layer of the endometrium capable of generating hESF (Yin et al., 2019, Schwab and Gargett, 2007, Masuda et al., 2012). The ability to identify and isolate adult endometrial mesenchymal stem cells (eMSC) is a significant advance for the study of endometrial disease, however the mechanisms for maintenance and expansion of the eMSC and subsequent differentiation into hESF remain to be defined (Gurung et al., 2018). Further, it is unknown whether the etiology of endometrial and reproductive disease is developmental or develops de novo in the adult. There is therefore a need to develop techniques for generating large numbers of highly pure hESF from pluripotency.

In the past decade, induced pluripotent stem cells (iPSC) have proven to be invaluable for the study of both normal development and human disease. Differentiation protocols from iPSC to many cell types of interest have been continually optimized for improved yield, purity, and functional application. However, the development of differentiation protocols for hESF-like cells from iPSC has just begun (Miyazaki et al., 2018). This initial protocol used embryoid bodies to produce hESF-like cells that responded to hormones to decidualize, but it remains to be determined whether these cells interact with other endometrial cell types and faithfully model endometrial development or disease states.

While ESFs represent the bulk of the cells in the endometrium, epithelial cells also participate in decidualization and are necessary for endometrial processes related to implantation. Three-dimensional (3D) hormone responsive organoid models of the human epithelium have been established by several groups from endometrial biopsy and first trimester placenta (Turco et al., 2017, Boretto et al., 2017). While decidual ESF are also present when endometrial epithelial organoid (EEO) cultures are being established (Male et al., 2012, Haider et al., 2019), they do not associate with the EEOs and are not maintained over time in cocultures (Turco et al., 2017, Marinic and Lynch, 2019, Boretto et al., 2017). Endometrial spheroids containing both stromal and epithelial cell can be generated from endometrial biopsies, but they cannot be maintained long term, and have not been characterized for epithelial and stromal decidualization and interactions (Wiwatpanit et al., 2020).

Here we describe a directed monolayer differentiation protocol for generating human ESF lineage cells from PSCs. This results in ESF progenitor cells that are capable of selforganizing with primary EEOs from term placenta to form a 3D, hormone responsive cycling model of the human endometrium.

Differentiation of PSC to Endometrial Stromal Progenitors

Figures 7A, 7B, 7C, 7D, 7E, 7F, 7G, 7H, 7I, 7J, 7K, 7L:
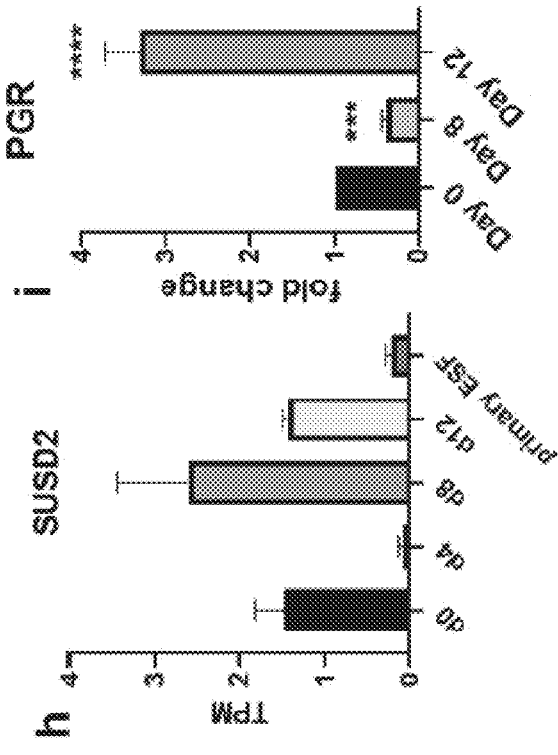
Figures 7A, 7B, 7C, 7D, 7E, 7F, 7G, 7H, 7I, 7J, 7K, 7L:
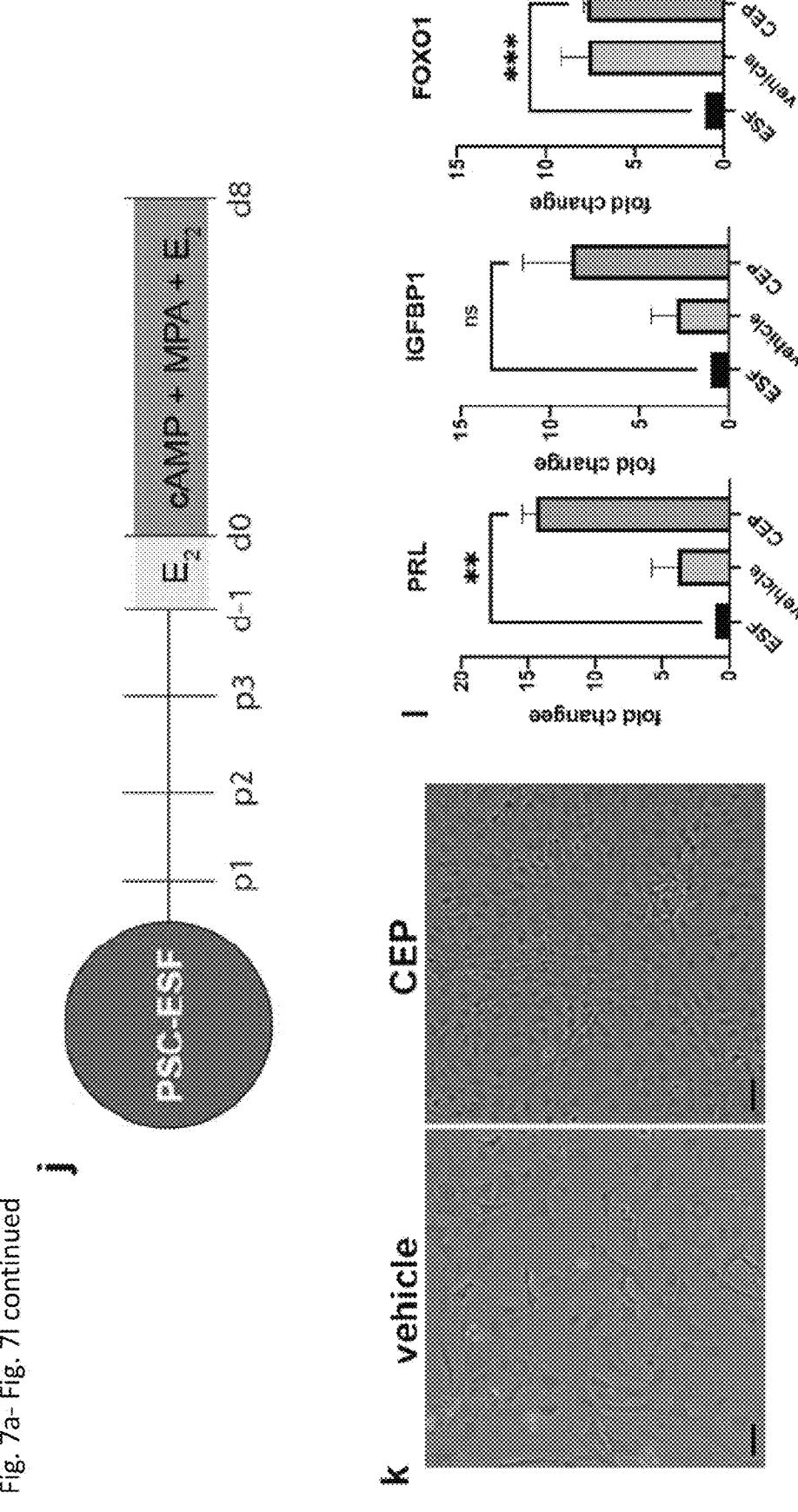

Generation of ESF from pluripotent stem cells (PSC) involves sequential differentiation of the cells through a series of intermediate progenitor cells species (FIG. 6). The first step (FIG. 1a) requires the specification of intermediate mesoderm (IM), a common mesodermal progenitor for both nephric and reproductive tracts (Yucer et al., 2017). We tested several IM-generating protocols used previously in kidney and fallopian tube cell differentiation from PSC (Takasato et al., 2014, Yucer et al., 2017, Morizane et al., 2015), and determined that treatment of PSC with CHIR99021 (804), a glycogen synthase kinase 3 (GSK3) inhibitor that activates canonical WNT/B-catenin signaling, resulted in a rapid expansion of cells that could subsequently be differentiated further to the endometrial lineage (FIG. 7a, b). We observed high levels of mesodermal-specific Brachyury (TBXT) gene expression, and concurrent reduction of pluripotency markers OCT3/4 and SOX2 in 2 days (FIG. 1b, d). LHX1 and PAX2, two transcription factors expressed in the intermediate mesoderm (IM), also were detected at this time (FIG. 1c, d). We observed that there was no increase in ectoderm lineage marker, SOX2, and a low but significant increase in expression of endoderm and mesendoderm marker SOX17 (FIG. 1b, c). At day 4 of differentiation, TBXT expression was decreased, LHX1 and PAX2 expression was either maintained or increased, and expression of anti-Müllerian hormone receptor 2 (AMHR2), a specific marker of Müllerian duct mesenchyme, increased (FIG. 1b, c, e).

To preferentially expand the Müllerian duct mesenchyme population, at day 4 we continued activating the WNT/B-catenin pathway with WNT7A (100 ng/ml) treatment from day 4-8. WNT7A treatment further induced the Müllerian mesenchyme specific AMHR2 but did not induce the epithelium specific marker WNT7A (FIG. 1e), indicating that the WNT7A treatment promoted mesenchymal rather than epithelial differentiation. The Müllerian duct is patterned along the anterior-posterior axis to develop into the fallopian tubes (HOXA9), endometrium (HOXA10 and HOXA11), cervix (HOXA11), and vagina (HOXA13) (Du and Taylor, 2015). We found that at day 8 of differentiation, HOXA10 and HOXA11, but not HOXA9 and HOXA13 (FIG. 1f) were significantly upregulated, substantiating the appropriate regionalization of the cells. Immunocytochemical (ICC) analyses validated the qPCR results with increasing nuclear expression of the HOXA11 transcription factor from day 0 to day 8 (FIG. 1g). The expression of mesenchymal lineage markers platelet derived growth factor beta (PDGFRβ) and vimentin (VIM) supported specification to the stromal cell type (FIG. 1h). HOXA11 was confirmed to be co-expressed with mesenchymal markers AMHR2 and VIM (FIG. 1h, i). Upon quantification, we found that 78.55+8.17% of DAPI+ cells expressed both AMHR2 and HOXA11, while 92.27+ 5.15% of the DAPI+ cells were positive for HOXA11 alone (FIG. 1i, j). Further, 93.31+1.46% of the cells were Ki67+, confirming that the cells at day 8 are in cell cycle (FIG. 1i, j). PSC-ESP at day 8 of differentiation could be frozen and thawed for subsequent differentiation, generating cells with appropriate proliferative properties and lineage-specific marker expression (FIG. 7f, g). In toto, these findings indicate that developmentally and regionally appropriate endometrial stromal progenitors, which we termed PSC-ESP, were generated at this point of the differentiation protocol.

Maturation of PSC-ESP to Hormone Responsive Endometrial Stromal Fibroblasts

Figures 2A, 2B, 2C, 2D, 2E, 2F, 2G, 2H, 2I:
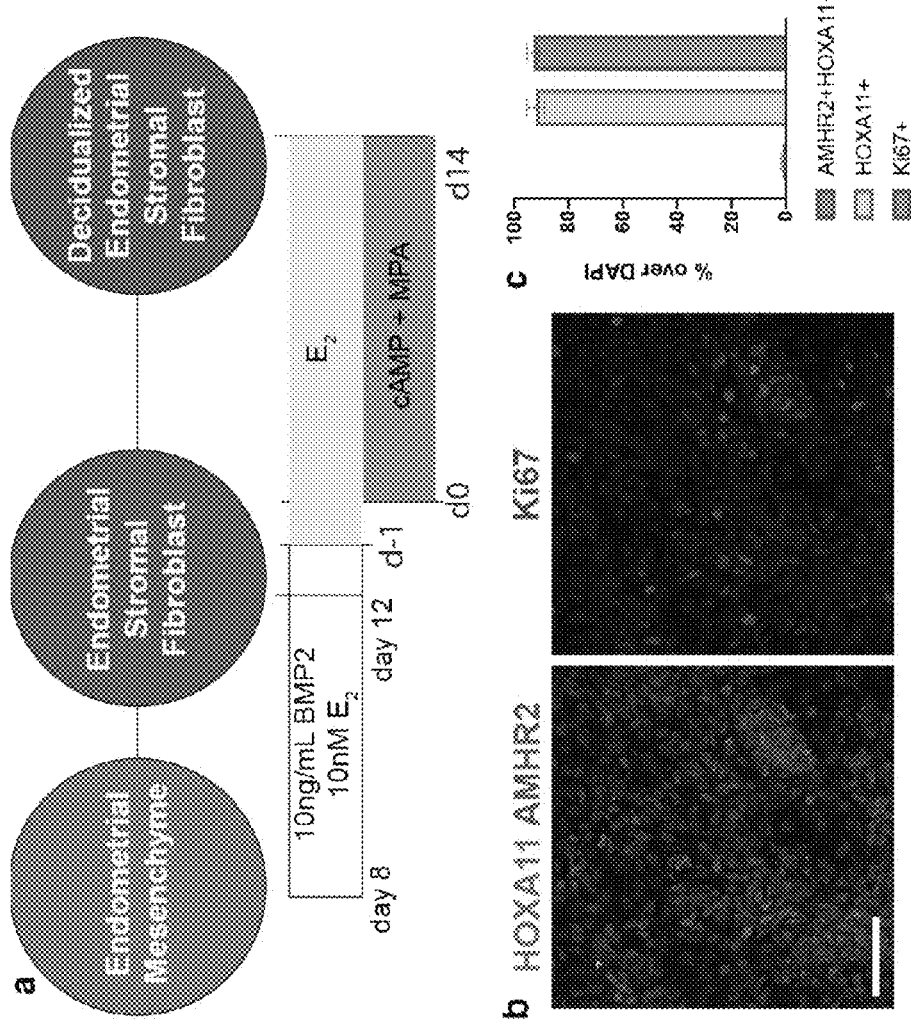
Figures 2A, 2B, 2C, 2D, 2E, 2F, 2G, 2H, 2I:
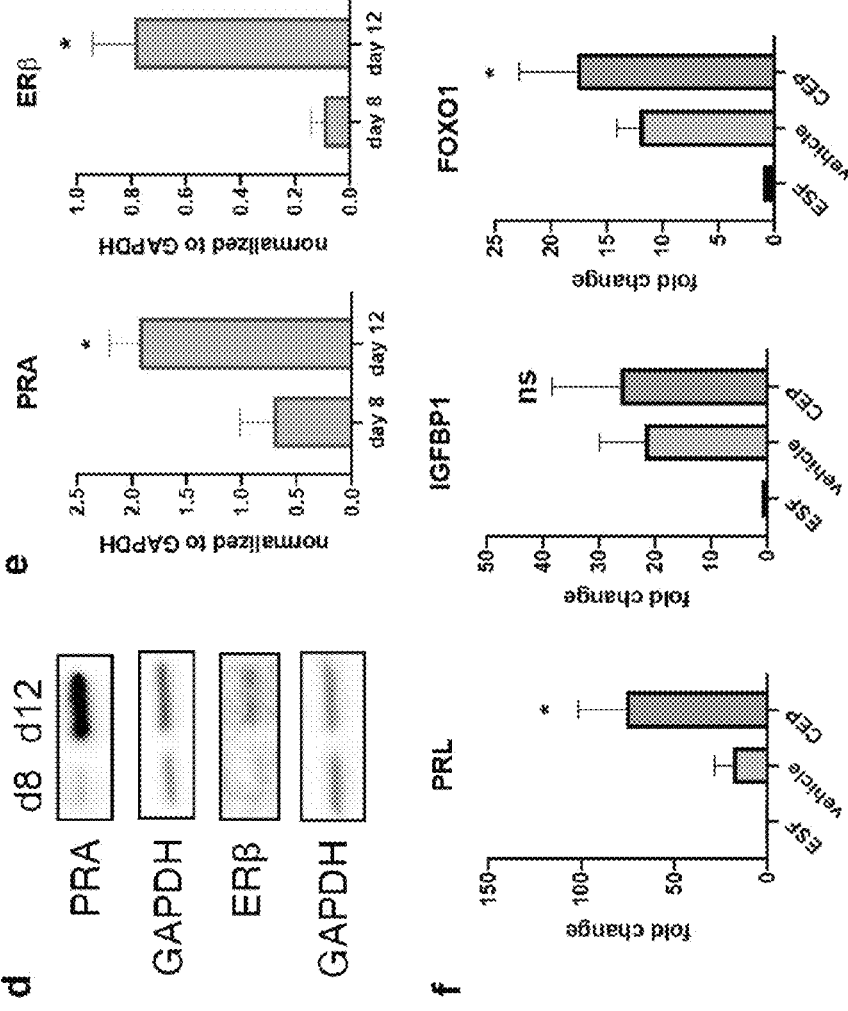
Figures 2A, 2B, 2C, 2D, 2E, 2F, 2G, 2H, 2I:
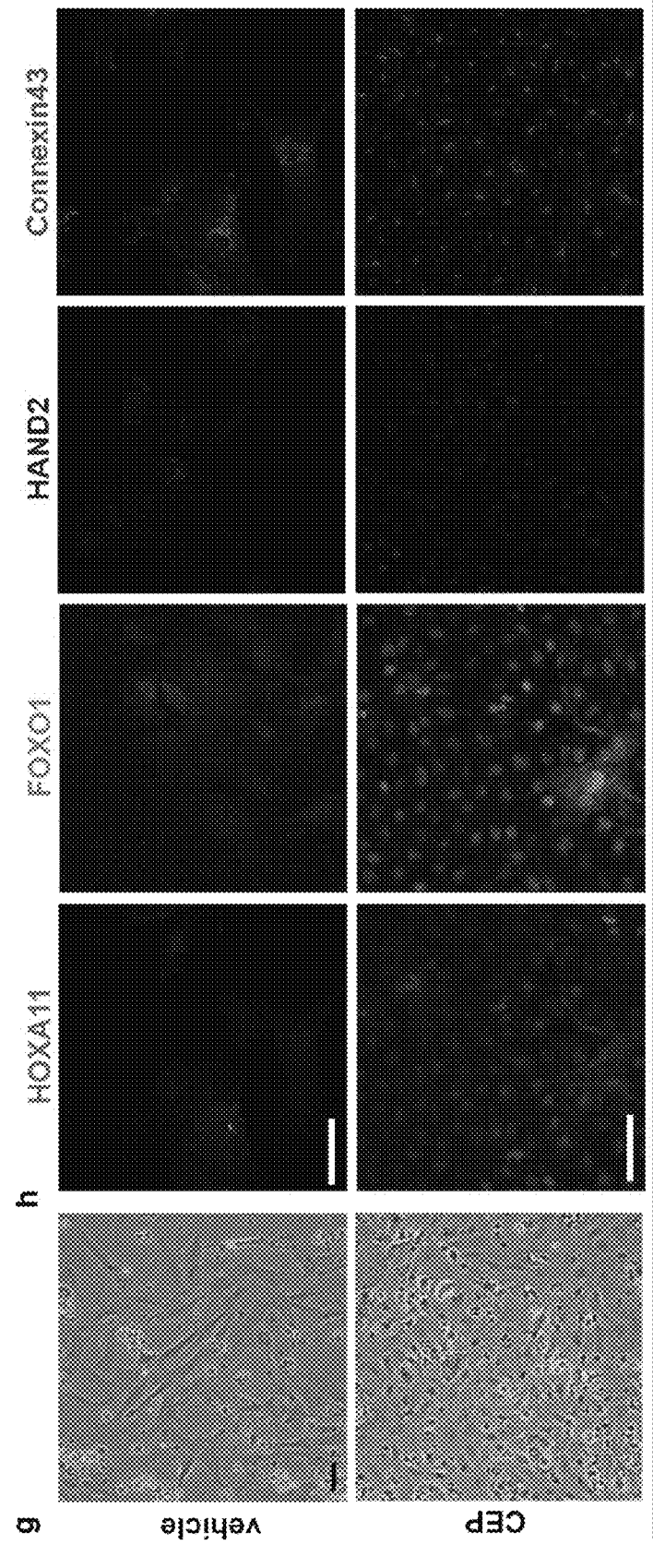
Figures 2A, 2B, 2C, 2D, 2E, 2F, 2G, 2H, 2I:
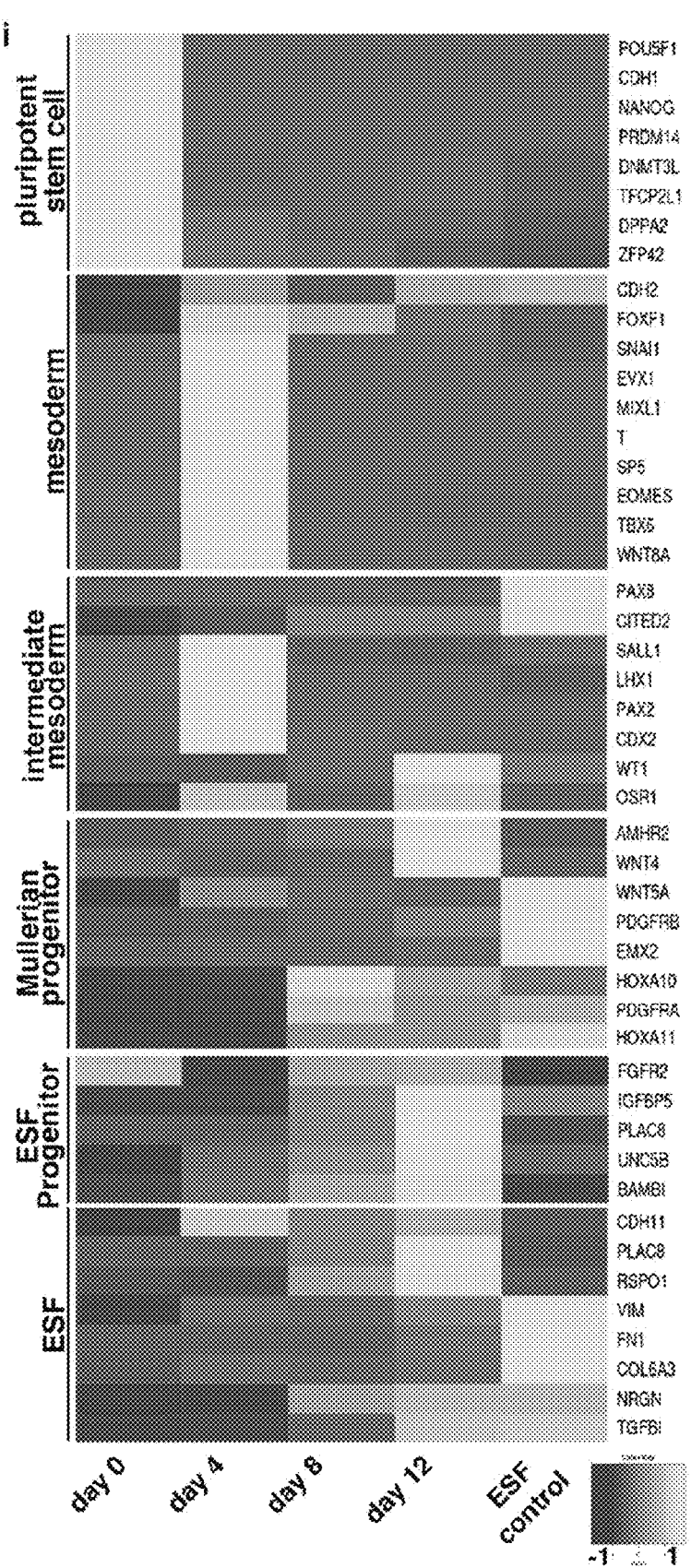

We next sought to further mature the PSC-ESP and to promote expression of progesterone receptor (PR) and estrogen receptor (ER) to enable decidualization responses. To accomplish this, day 8 PSC-ESP were treated for 4 days with bone morphogenetic protein 2 (BMP2, 10 ng/ml) and β-estradiol ($E_2$, 10 nM), which regulate PR and ER expression in endometrial stromal cells (Fullerton et al., 2017, Li et al., 2013, Lee et al., 2007, McLean et al., 2000, Ing and Tornesi, 1997) (FIG. 2a). AMHR2 is only expressed in the developing endometrial mesenchyme whereas HOXA10 and HOXA11 expression is maintained in adult ESF (Saatcioglu et al., 2019). At day 12 of differentiation, the PSC-ESP continued to express the mesenchymal marker VIM (FIG. 7c), but no longer expressed AMHR2 (FIG. 2b). Regionalization was maintained as measured by HOX family transcripts, HOXA10 expression (FIG. 7d,e) as well as HOXA11 expression in 92.04+1.73% of the cells (FIG. 2b,c). Loss of AMHR2, while maintaining HOXA10, HOXA11 and Ki67 expression, is consistent with further maturation of the cells into ESF (FIG. 2b, c). Importantly, we detected increased expression of progesterone receptor (PGR) RNA by qPCR (FIG. 7i) and type A PR (PR-A) and estrogen receptor beta (ERβ) proteins by immunoblots in day 12 cells compared to day 8 (FIG. 2d, e). These findings suggest that at day 12 of differentiation, PSC-ESP have matured to PSC-ESF containing the molecular machinery to respond to hormone signals.

The PSC-ESF typically reached confluence at this time point and were passaged either for maintenance or for decidualization with 8-bromoadenosine-cAMP (cAMP), $E_2$, and medroxyprogesterone 17-acetate (CEP) as previously described (Aghajanova et al., 2009). After 14 days of this decidualization treatment with CEP, the cells acquired a more compact, rounded morphology, while the vehicle treated cells remained fibroblast-like (FIG. 2g). Transcripts of the decidualization markers, prolactin (PRL) and forkhead box O1 (FOXO1) were significantly increased over untreated primary ESF after CEP treatment (FIG. 2f). Transcripts of another commonly used decidualization marker, insulin growth factor binding protein (IGFBP1), also were increased after decidualization although this increase was not significant compared to vehicle treated controls. The PSC-ESF achieved the same decidualization response when treated after three passages (FIG. 7j, k, l). Immunocytochemistry demonstrated the expected nuclear expression of HOXA11, FOXO1, and HAND2 with CEP treatment (FIG. 2h). Gap junction protein, connexin43, was redistributed in response to CEP treatment to be perinuclear and to line the cuboidal cell border (FIG. 2h). Taken together, these findings suggest that day 12 PSC-ESF respond appropriately to decidualization signals.

Figures 1A, 1B, 1C, 1D, 1E, 1F, 1G, 1H, 1I, 1J:
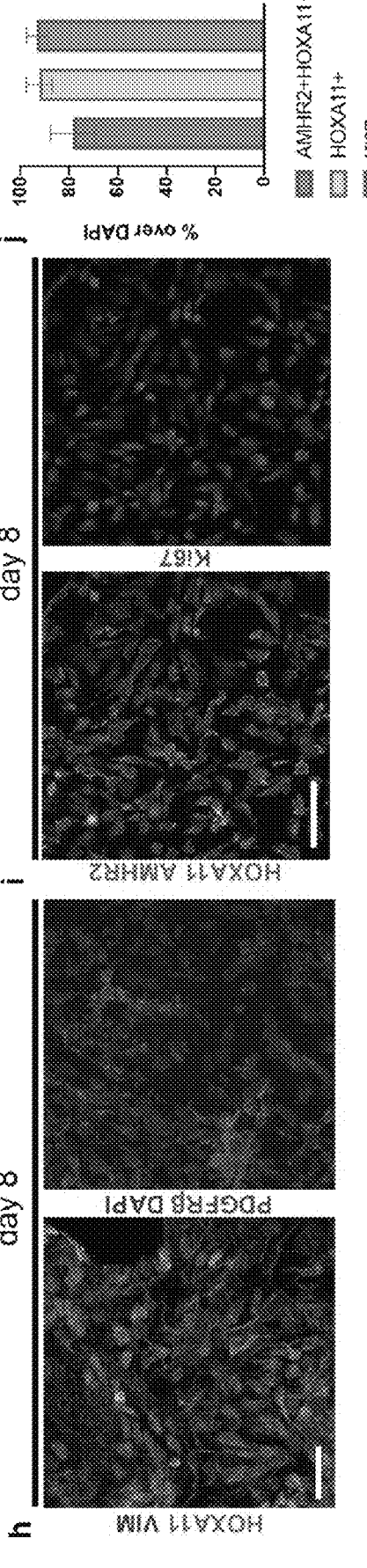

To investigate the developmental transcriptomic profiles of cells along the differentiation protocol, we measured gene expression of PSC derived cells at day 0, 4, 8, and 12 of differentiation by RNA sequencing and evaluated the expression of established molecular markers that reflect fate commitment along the endometrial stromal cell lineage (FIG. 2i). At day 4 of differentiation, mesoderm and IM genes were most highly expressed while pluripotency genes were no longer expressed—supportive of the previous findings with select markers (FIG. 1). Day 8 PSC-ESP expression was most represented by genes of the ESF progenitor developmental phase. As expected, adult ESF genes are most highly expressed at day 12, similar to ESF control. (Saatcioglu et al., 2019). These expression data along with the protein expression data indicate that this protocol replicated the normal lineage progression from pluripotent stem cells through various developmental stages leading to adult ESF.

Interestingly, ESF progenitor genes are highly expressed at day 12 but not in cultured primary ESF controls. This suggests PSC-ESF likely possess progenitor qualities that distinguish the cells from primary ESF in culture.

PSC-ESF and EEO Self-Organize to Form a Co-Culture Model of Human Decidua

Figures 3A, 3B, 3C, 3D, 3E, 3F, 3G:
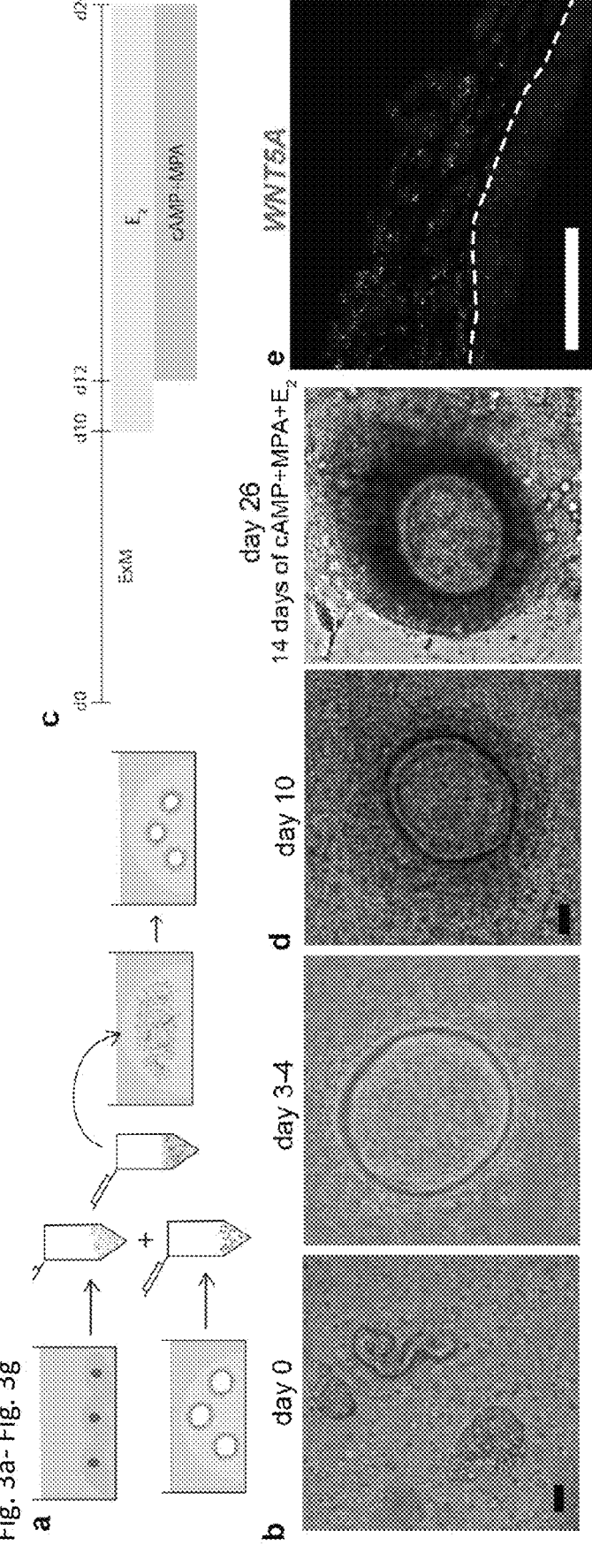
Figures 3A, 3B, 3C, 3D, 3E, 3F, 3G:
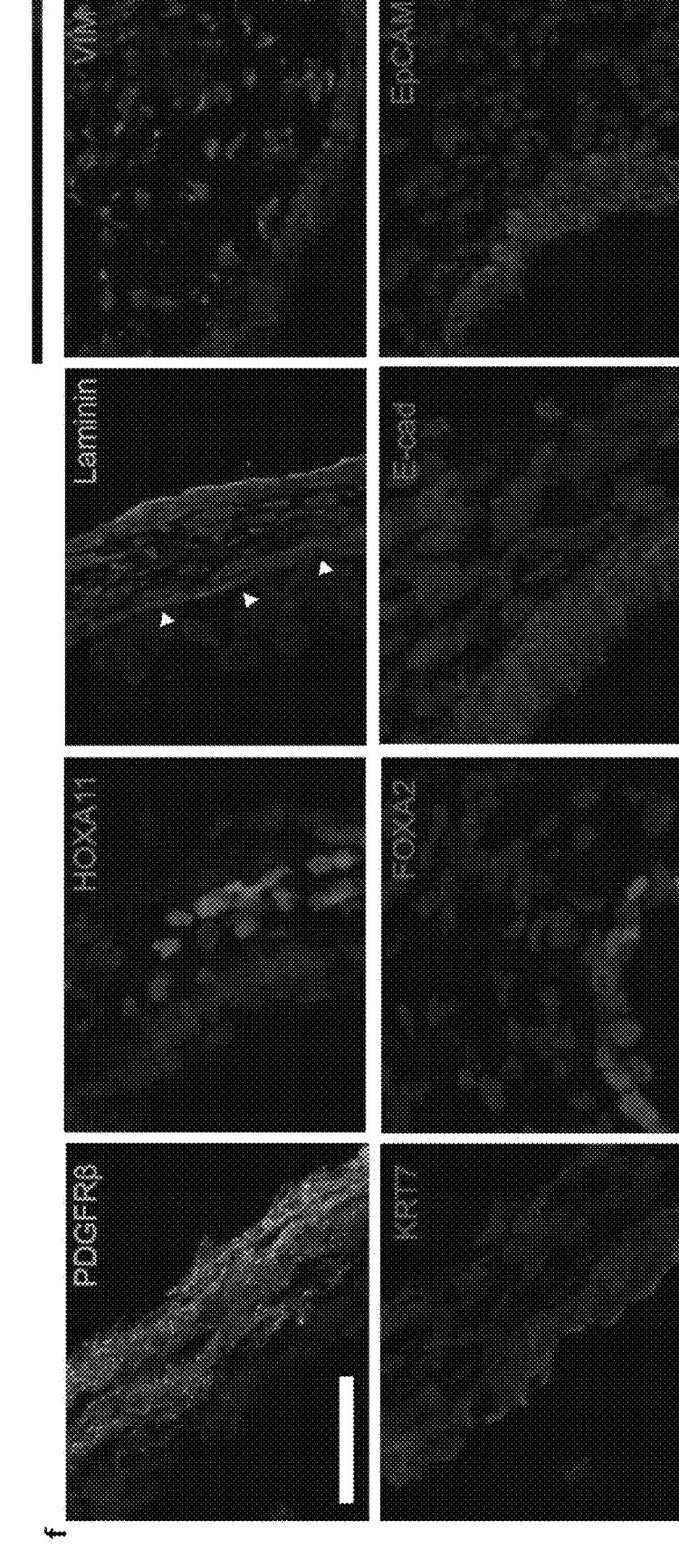
Figures 8A, 8B, 8C, 8D, 8E, 8F, 8G, 8H:
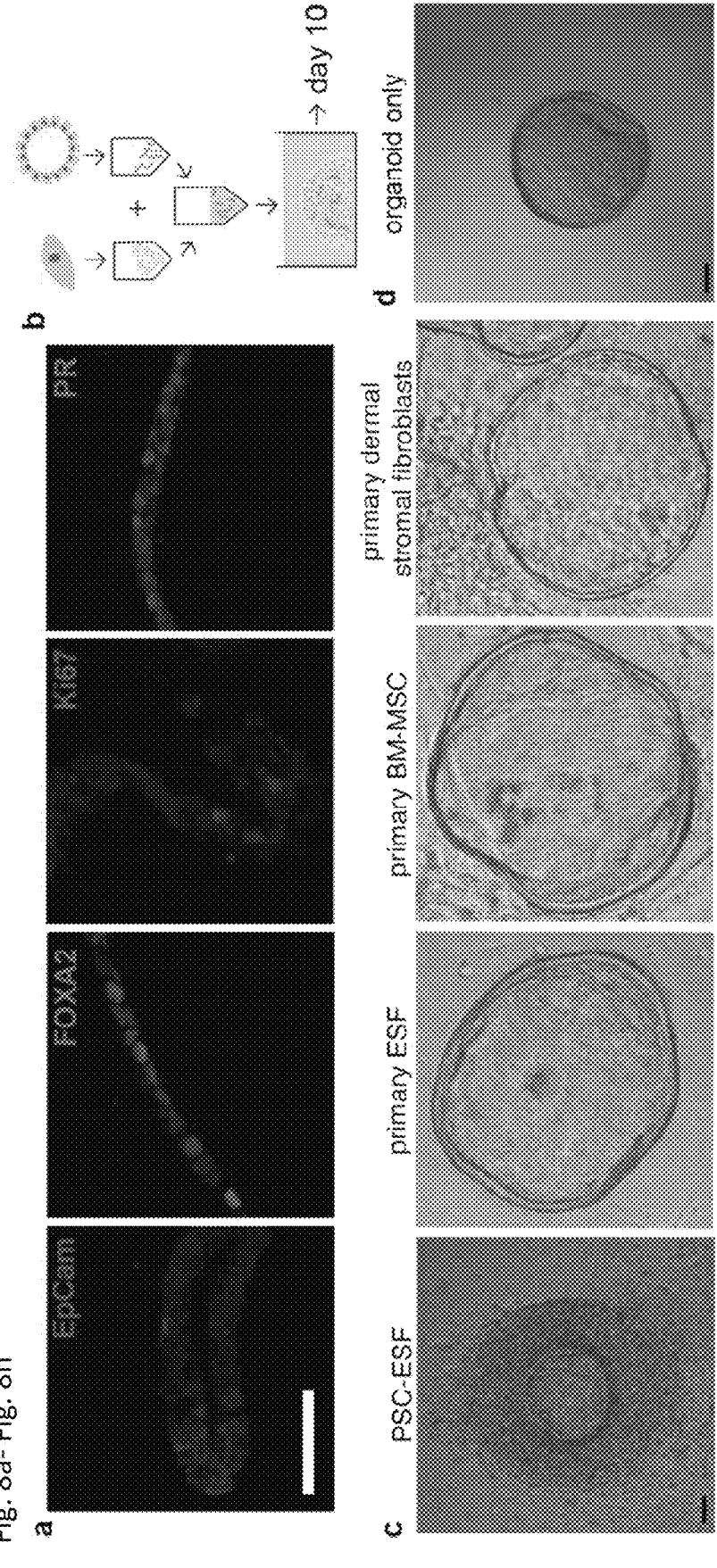
Figures 8A, 8B, 8C, 8D, 8E, 8F, 8G, 8H:
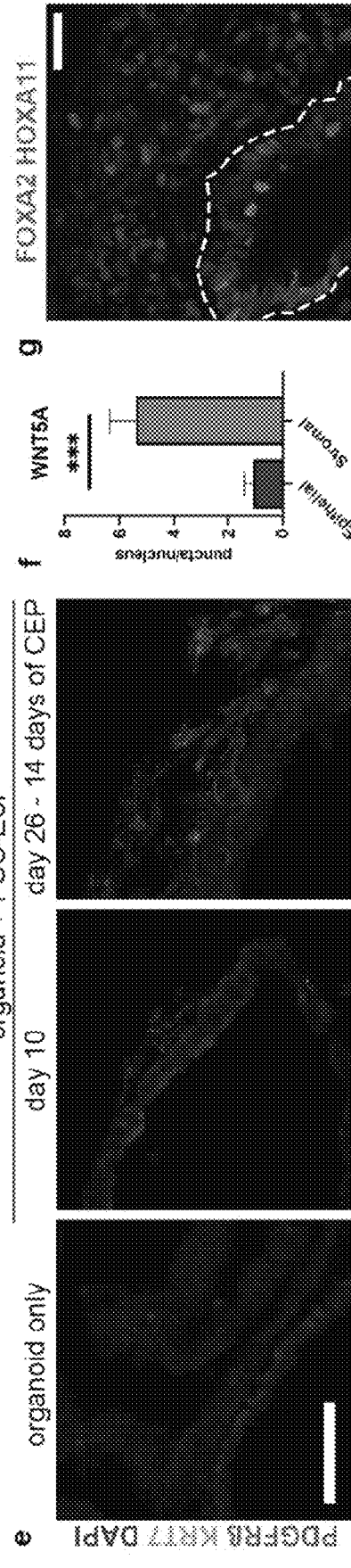

In vivo, decidualization and implantation processes are accomplished by the coordination of dESF and epithelial cells. We therefore explored whether PSC-ESF can be cocultured with endometrial epithelial cells as 3 dimensional (3D) organoids. We adapted published methods to generate endometrial epithelial organoids (EEO) from decidual glands harvested from term postpartum placenta (Turco et al., 2017, Marinic et al., 2020), and validated EEO cell type specificity with immunocytochemical staining of endometrial epithelium expressed markers (FIG. 8a). To establish the co-cultures (FIG. 3a), EEO and PSC-ESF each were dissociated separately and then mixed in Matrigel to allow self-assembly in organoid Expansion Media (ExM). In 3-4 days, we observed co-culture formation with an outer layer of PSC-ESF and an inner layer of epithelial cells (FIG. 3b). This interaction was maintained for 10 days in hormone-free ExM. We found that this interaction was specific to PSC-ESF as no interaction was formed between EEO and other stromal and progenitor cell types: primary ESF, primary bone marrow derived mesenchymal stem cells, and primary dermal stromal fibroblasts (FIG. 8c).

At day 10, EEO and PSC-ESF co-cultures or EEO only were subsequently treated with a 16-day decidualization treatment (FIG. 3c). During this time, we observed thickening of the outer stromal cell layer in the co-cultures, while EEO only cultures remain largely unchanged (FIG. 3d, FIG. 8d). ICC analysis at the end of the decidualization period found an expansion of the PDGFRβ+ PSC-ESF population (FIG. 8e). Further characterization at day 26 of the co-culture demonstrated that PSC-ESF expressed ESF enriched transcript, WNT5A (FIG. 3e, FIG. 8f), as well as ESF specific proteins HOXA11 (FIG. 3f, FIG. 8g). In addition to endometrial specific markers, the PSC-ESF outer layer expressed stromal proteins PDGFRβ, VIM, and Laminin. EEO cultures retain cell polarity as evidenced by Laminin expression along a single, basolateral, surface (Turco et al., 2017) In vivo, ESF interface with the basement membrane of the epithelial cells (Jin, 2019), This indicates that co-cultured EEO and PSC-ESF interfaced with appropriate cell polarity along the Laminin+ basolateral surface of the EEOs.

(FIG. 3f). KRT7, EpCAM, E-cadherin staining specifically marked the epithelial cell layer while FOXA2 positivity confirmed the glandular origin of the cells (FIG. 3f, FIG. 8g).

We sought to determine whether both cell types in the co-culture responded appropriately to decidualization signals. ICC analysis post decidualization revealed the expected pattern of nuclear PR as well as cytoplasmic FOXO1 in EEO (FIG. 3g) (Vasquez et al., 2018). Luminal and superficial glandular epithelium are ciliated along the apical surface during the secretory phase; similarly, EEOs have been reported to become ciliated, as marked by Acetylated-a-tubulin (AcTUB), after hormone treatment with cAMP+P4+E$_2$+PRL, or E$_2$ alone (Turco et al., 2017, Haider et al., 2019). We found that co-cultured EEO gained AcTUB expression along the apical surface, after CEP treatment in comparison to vehicle or untreated EEO (FIG. 8h). The stromal compartment of the co-culture responded to decidualization with increased expression of cytoplasmic FOXO1, nuclear HAND2 and membrane-associated connexin43 when compared to co-cultures treated with vehicle alone (FIG. 3g). In summary, these findings suggest that the PSC-ESF and EEO specifically self-organize in an orientation that would be found in vivo, express endometrial specific stromal and epithelial cell markers, and respond to hormone treatment to express markers and structures of the decidua in vivo.

PSC-ESF and EEO Respond to Cyclic Hormone Treatment

Figures 4A, 4B, 4C, 4D, 4E, 4F, 4G, 4H:
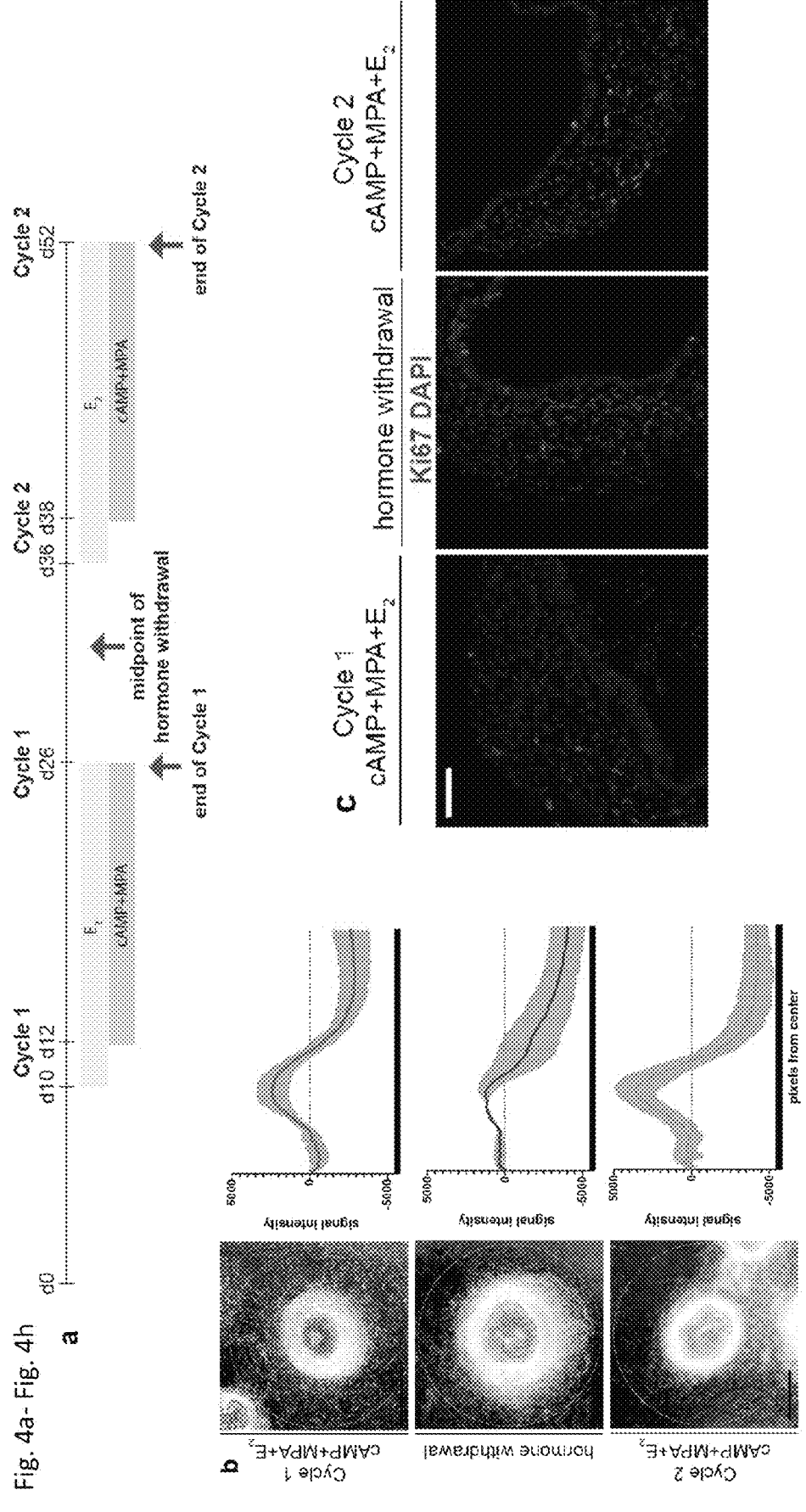
Figures 4A, 4B, 4C, 4D, 4E, 4F, 4G, 4H:
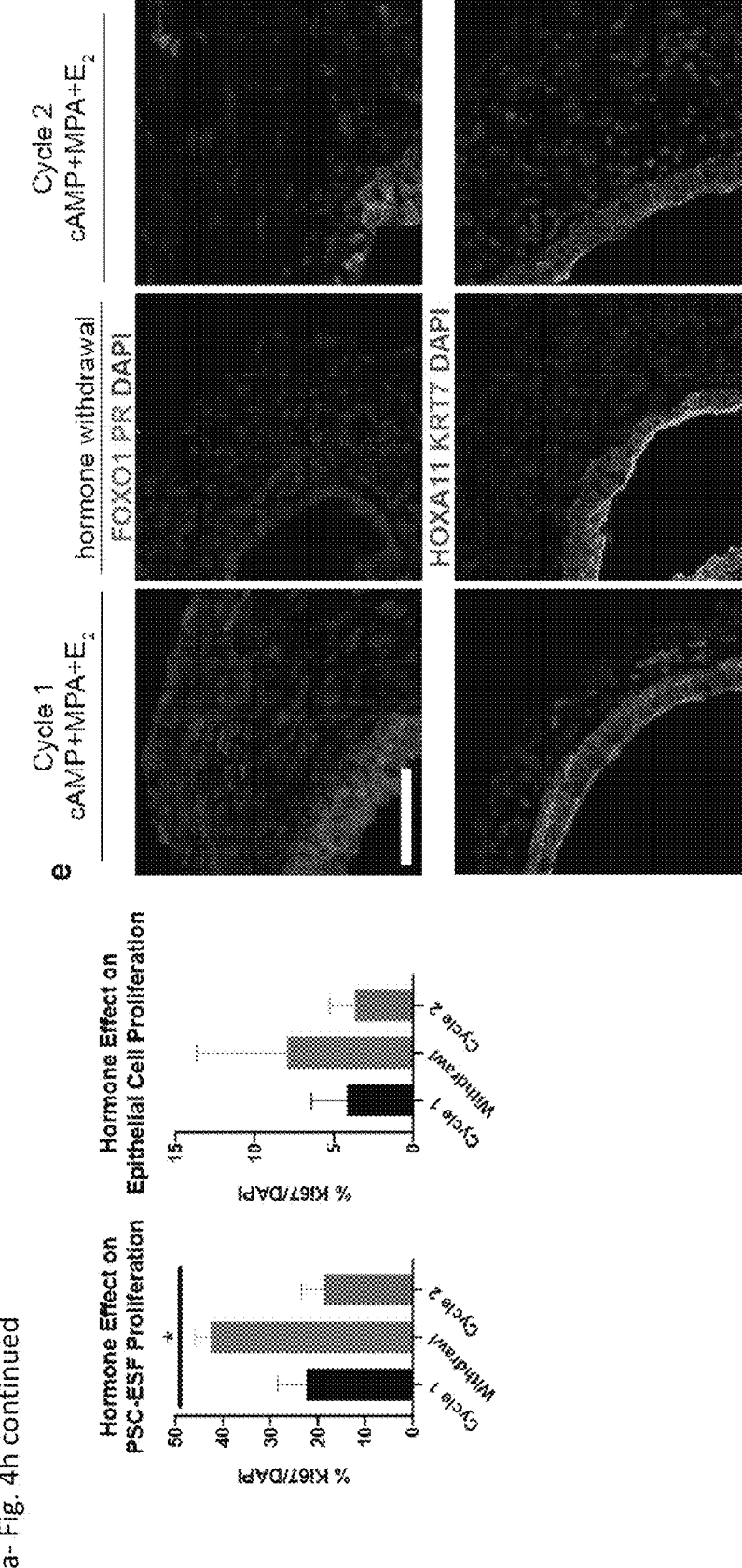
Figures 4A, 4B, 4C, 4D, 4E, 4F, 4G, 4H:
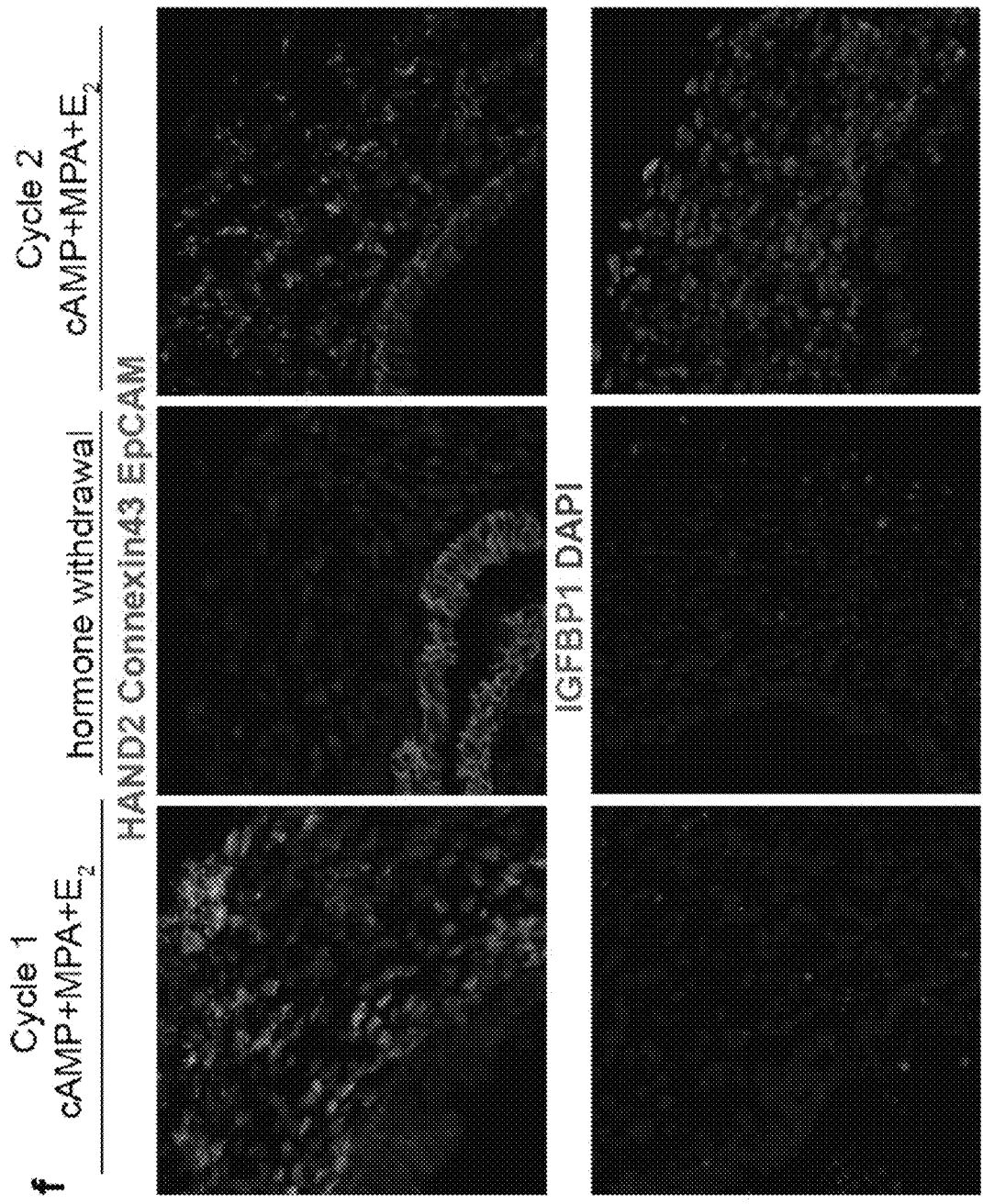
Figures 4A, 4B, 4C, 4D, 4E, 4F, 4G, 4H:
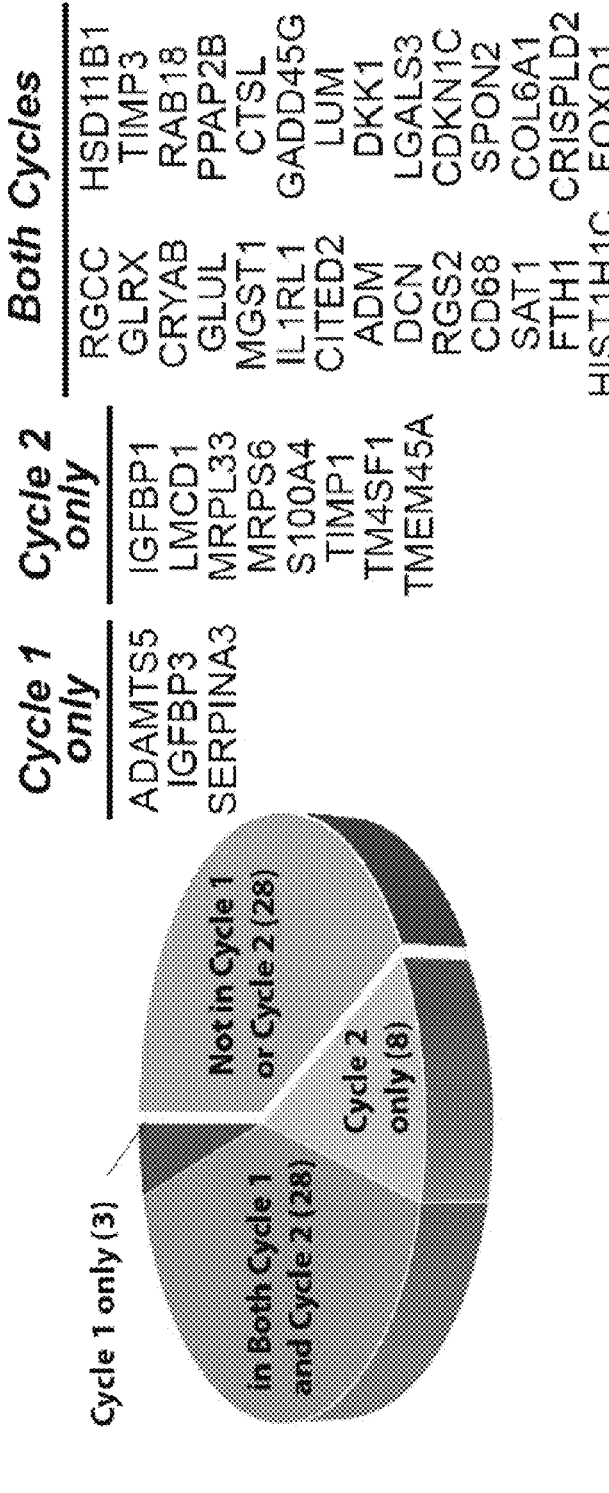
Figures 4A, 4B, 4C, 4D, 4E, 4F, 4G, 4H:
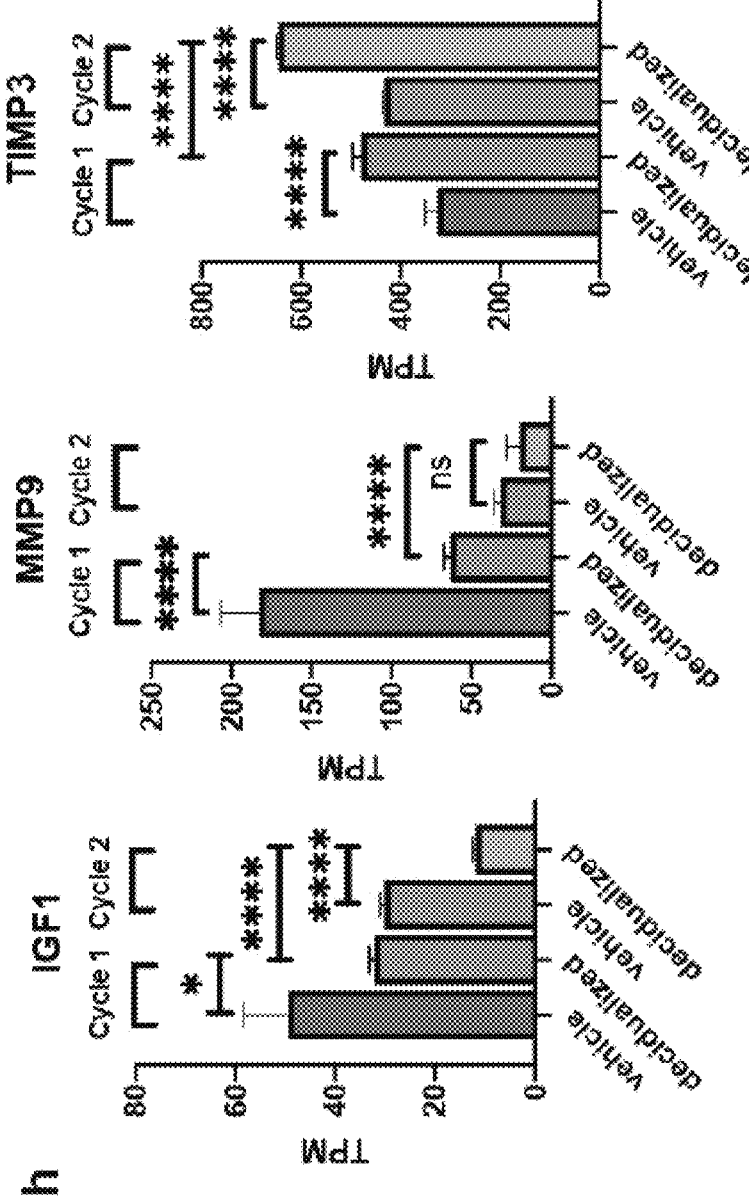

In human endometrium, the decidua is shed and reconstituted in response to cyclic changes in hormones during the menstrual cycle. We therefore asked whether the organoids similarly respond to cyclic decidualization cues. To test this hypothesis, we needed to determine how to maintain the co-cultures for prolonged treatments. Co-cultures dissociated to single cells did not reform co-cultures or EEO (data not shown). However, when co-cultures were replated into fresh Matrigel as whole organoids, they continued to expand and demonstrated morphological responses to changes in hormone treatment. Co-cultures were exposed to two periods of 16-day decidualization (CEP) treatment, referred to as Cycle 1 and Cycle 2, and separated by a 10-day period of hormone withdrawal (ExM) (FIG. 4a). Morphological examination of the organoids showed a dense stromal cell layer at the end of both Cycle 1 and Cycle 2. However, during the period of hormone withdrawal there was thinning and dispersion of the stromal cell layer. These changes in stromal layer thickness and density were quantified by measuring signal intensity radially from the center of the EEO (FIG. 4b). Co-cultures at the end of Cycle 1 and Cycle 2 had distinct peaks and sharp drop offs in signal intensity supportive of densely formed stromal cell layers. During hormone withdrawal there was still a peak of signal indicating the maintenance of the stromal cell layer proximal to the EEO, but there was a less sharp drop off in signal, supportive of the morphologic appearance of dispersion of the stromal cell layer (FIG. 4b) Endometrial biopsies from women at various stages of menstrual cycle have identified an increase in Ki67$^+$ cells during menses when compared to the cells in secretory phase (Vaskivuo et al., 2000). We therefore asked whether cycling of hormonal signals alters cell proliferation in the organoids similar to that observed in vivo. ICC analysis using antibodies against Ki67 (FIG. 4c, 4d) and phosphorylated histone H3 (FIG. 9a) across the three time points showed a significant increase in the number of Ki67$^+$ stromal (42.55%) but not epithelial (7.97%) cells after hormone withdrawal compared to the end of each decidualization cycle (stroma—22.36% Cycle 1, 18.72% Cycle 2; epithelium—4.17% Cycle 1, 3.71% Cycle 2; FIG.

Figures 9A, 9B, 9C, 9D, 9E, 9F, 9G, 9H:
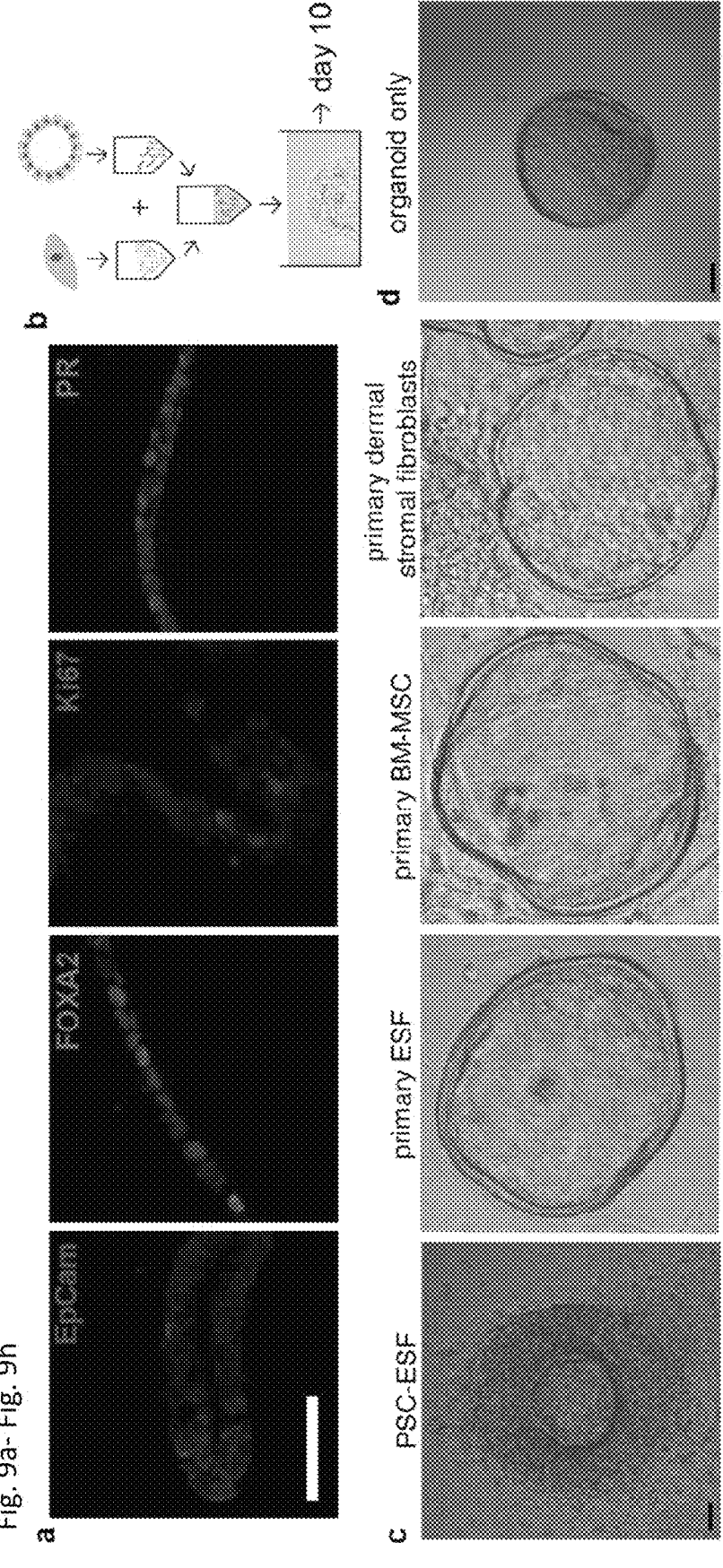
Figures 9A, 9B, 9C, 9D, 9E, 9F, 9G, 9H:
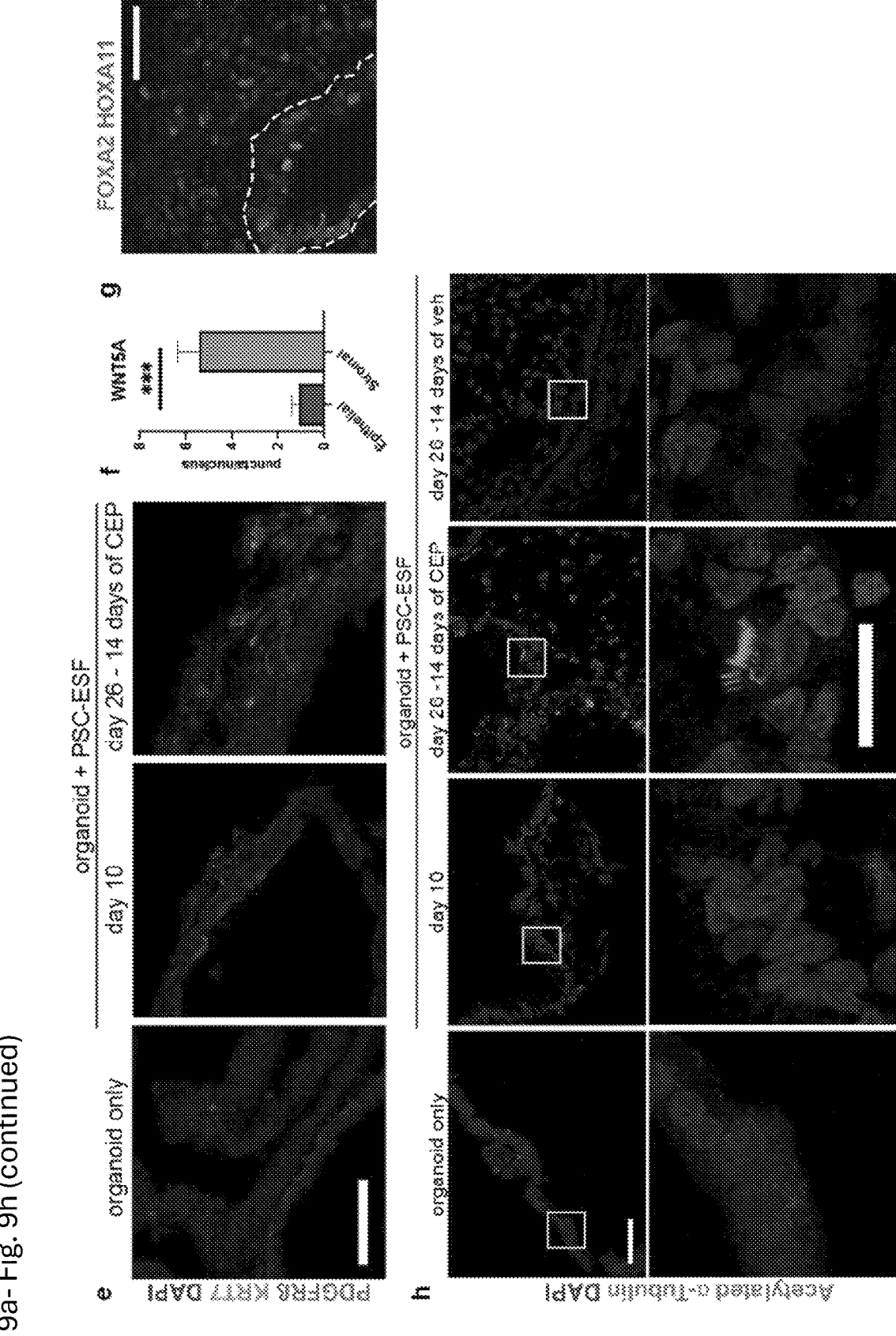

4d). Conversely, the percentage of Cleaved Caspase 3+(CC3) cells in the stromal and epithelial compartments were increased at the end of Cycle 1 and Cycle 2 while the percentage was decreased upon hormone withdrawal (FIG. 9b, c). Thus, cyclic changes in hormonal signals alter the proliferative properties of the stromal and epithelial compartment in the organoid similar to endometrial responses in vivo.

Figures 10A, 10B, 10C, 10D, 10E, 10F:
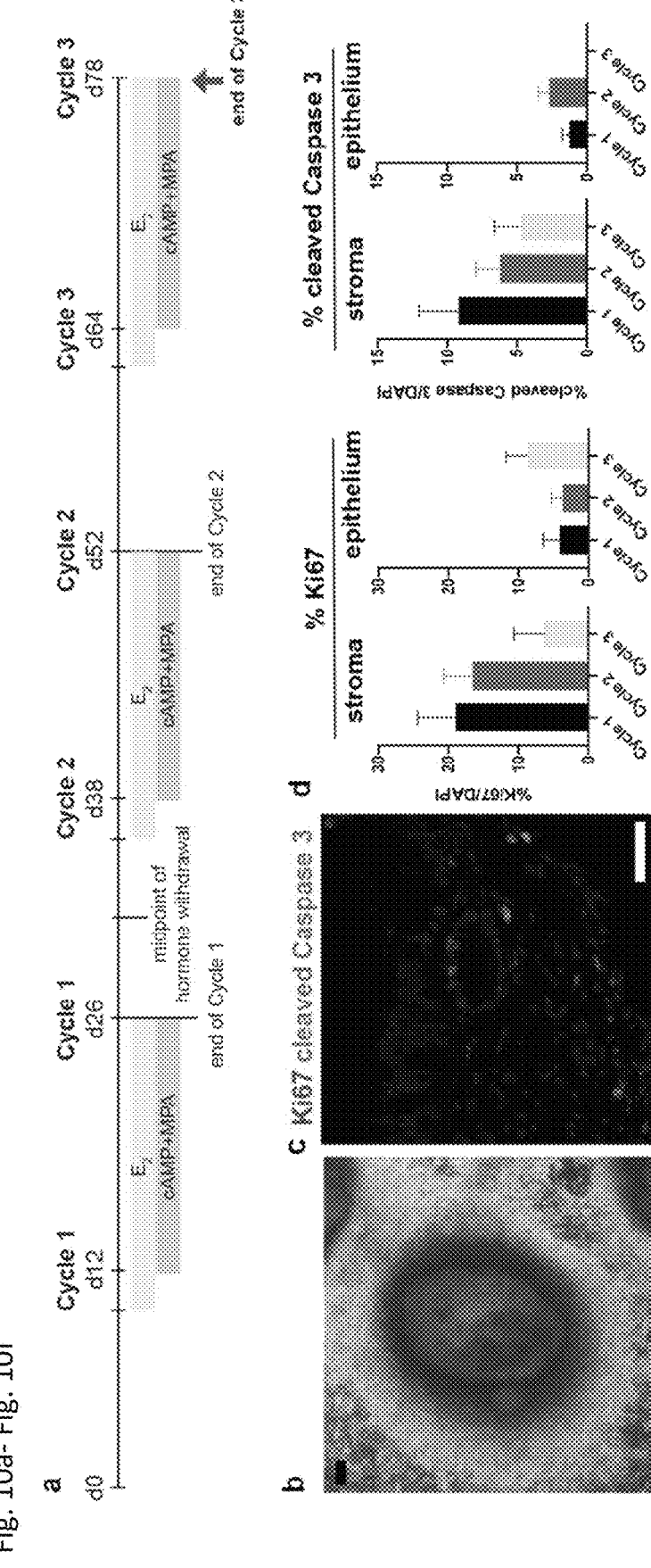
Figures 10A, 10B, 10C, 10D, 10E, 10F:
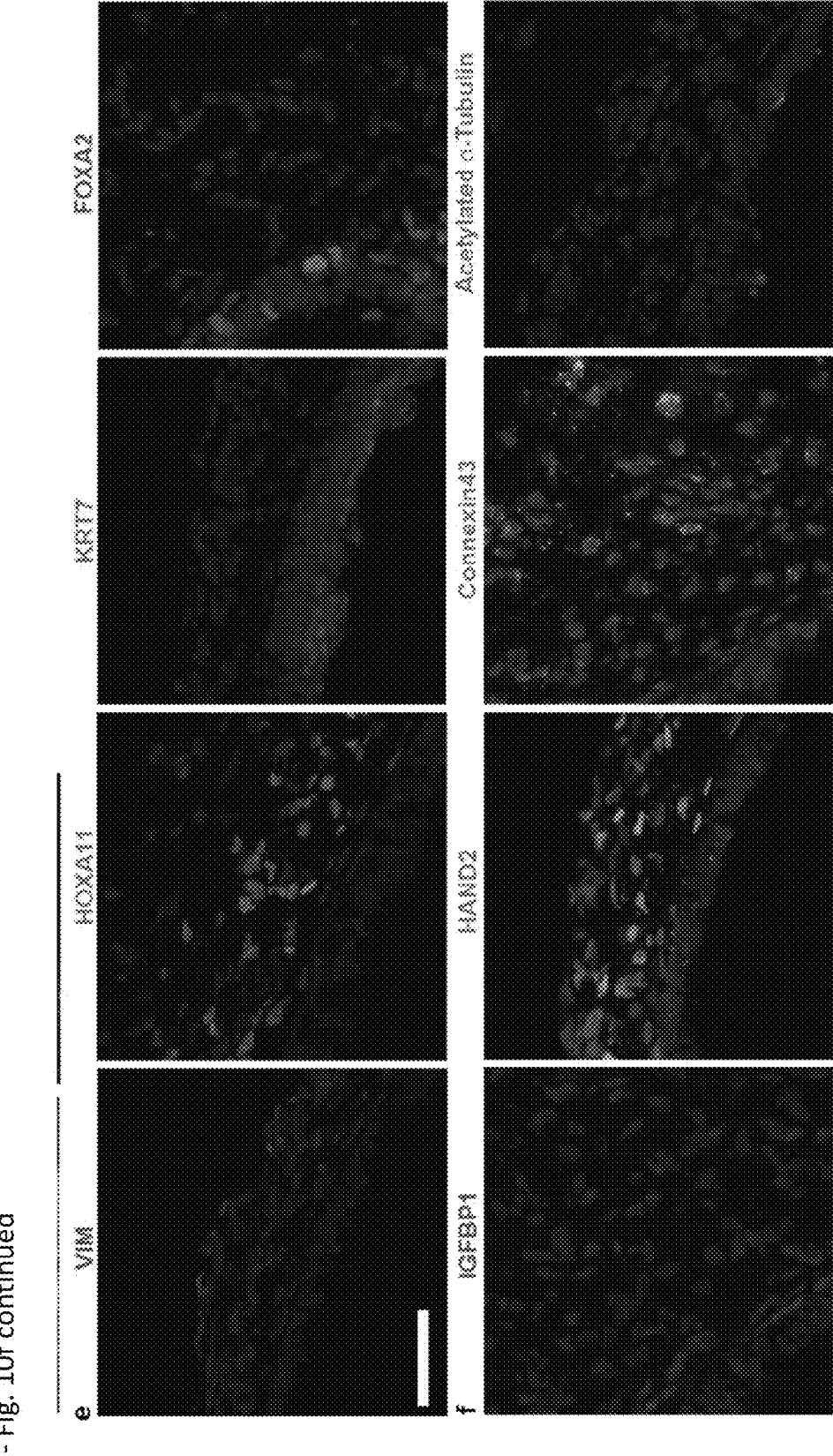
Figures 11A, 11B, 11C, 11D:
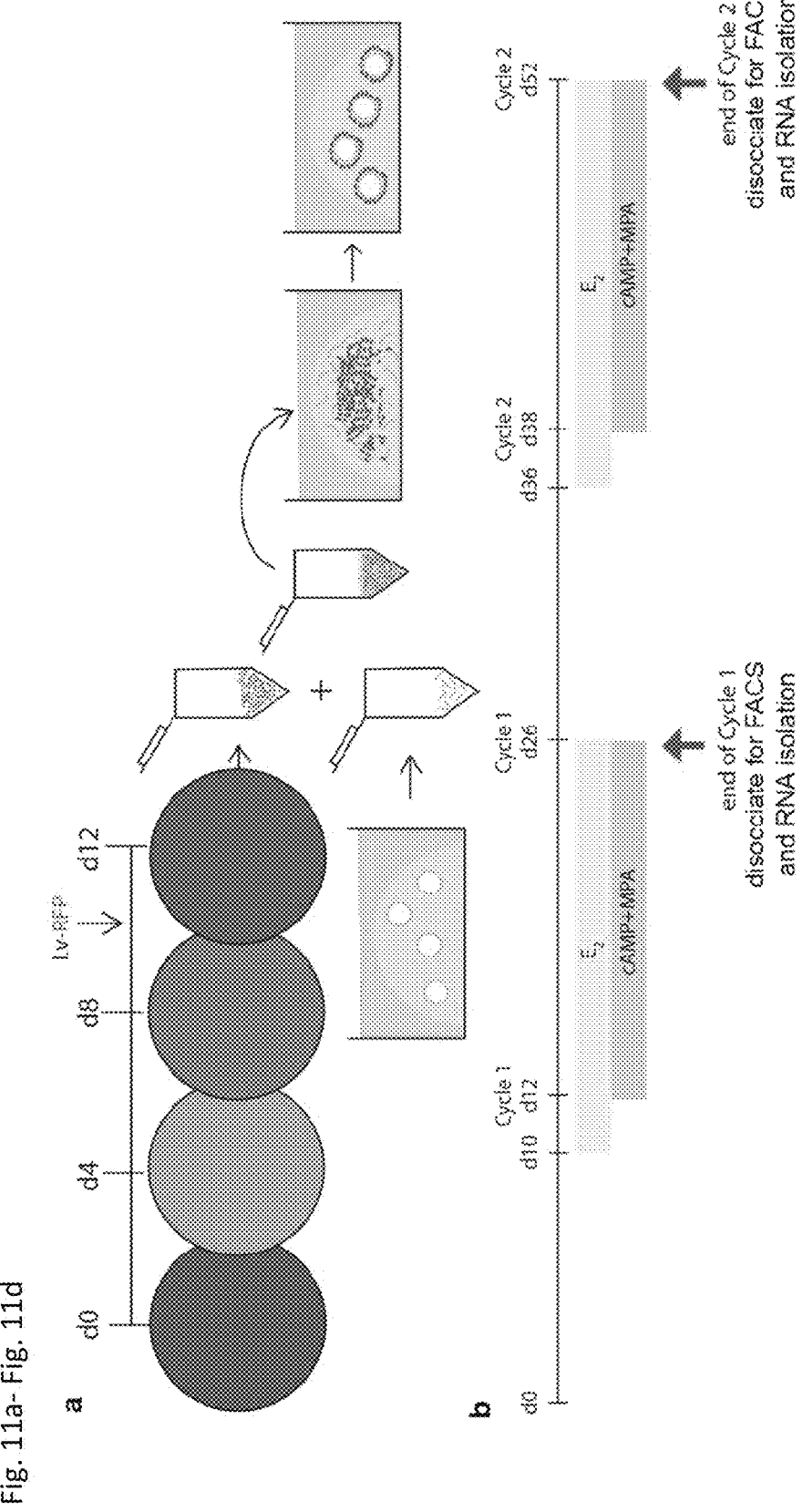

The increase in proliferative markers was associated with a decrease in expression of decidualization related genes after hormone withdrawal. In the epithelium, immunostaining for the decidualization markers PR and FOXO1 was observed both at the end of Cycle 1 and of Cycle 2 but was absent at the withdrawal time point (FIG. 4e). Further, the stroma exhibited a similar cyclic hormone response in expression of HOXA11 (FIG. 4e), HAND2, and connexin43 (FIG. 4f). However, these changes in expression were not observed when the co-cultures were maintained in vehicle at the same time points (FIG. 9d). There were some differences in the stromal markers between Cycle 1 and Cycle 2. Importantly, IGFBP1 was highly upregulated at the end of Cycle 2 while HAND2 was decreased compared to Cycle 1 (FIG. 4f), suggesting progressive differentiation of the stromal compartment between Cycle 1 and Cycle 2. A third cycle of 16 days of hormone treatment following cycle 2 continued the trend of stromal differentiation, with retention of cell type specific markers and further reduction in proliferation without increased apoptosis (FIG. 10). This suggests that the decidualization potential of progenitors in the stromal compartment of the organoids may peak at Cycle 2.

The decidualization responses in PSC-ESF at Cycle 1 and Cycle 2 were more thoroughly characterized using RNA-sequencing. PSC-ESF were labelled at day 10 of differentiation in monolayer by transduction with a lentivirus overexpressing the red fluorescent protein, RFP (FIG. 11), and the labelled cells were used to generate the co-culture organoids. At the end of Cycle 1 and of Cycle 2, after hormone or vehicle treatment, RFP$^+$ cells were selected by fluorescence activated cell sorting for RNA isolation and sequencing. In order to characterize the decidualization response of the sorted PSC-ESF, we took advantage of recent studies characterizing the expression profiles of first trimester placenta and endometrial tissue by single-cell RNA-sequencing (scRNAseq). These studies reported the existence of two to three distinct ESF subtypes within the decidua with only one of those populations enriching for commonly used in vitro dESF markers. We used the expression profiles of the dESF populations from three separate studies to compile a list of dESF enriched genes (Vento-Tormo et al., 2018, Suryawanshi et al., 2018, Wang et al., 2018). The genes selected had expression levels 2-fold or greater than other populations with 5 transcripts per million or greater. Of the 67 genes, 28 were significantly upregulated in decidualized compared to vehicle treated ESF at both Cycle 1 and Cycle 2 (FIG. 4g). Three additional genes were significantly upregulated in Cycle 1 only while 8 additional genes were significantly upregulated in Cycle 2 only. Although decidualized gene expression was largely the same in Cycle 1 and Cycle 2, a greater number of genes was enriched by decidualization in Cycle 2 which suggests a progressively increased response to hormone treatment. Notably, IGFBP1 was significantly upregulated in Cycle 2 compared to Cycle 1, consistent with the IGFBP1 ICC (FIG. 4f). IGF signaling plays essential roles in the hormone responsive expansion and differentiation of stromal progenitors during decidualization (Ganeff et al., 2009). The higher IGFBP1 protein expression at the end of Cycle 2 suggested that co-cultured stromal cells progressively differentiate and decrease responsiveness to IGF signaling with time in culture. Consistent with reported in vivo expression profiles of IGF1 in stromal cells at different decidualization stages (Vento-Tormo et al., 2018), we found that IGF1 transcript was reduced in decidualized cells relative to vehicle controls, and lower in vehicle and decidualized Cycle 2 than in decidualized Cycle 1 (FIG. 4h).

We next investigated how IGFBP1 expression is differentially regulated in Cycle 1 and Cycle 2. In ESF, matrix metalloproteinases (MMPs) are expressed dynamically in accordance with the menstrual phase and are described to process IGFBP family proteins in ESF (Coppock et al., 2004, Goffin et al., 2003, Vassilev et al., 2005). We found that the menstrual phase associated gelatinase, MMP9, was repressed by decidualization in both cycles (Goffin et al., 2003, Vassilev et al., 2005) Interestingly, MMP9 expression was also higher after decidualization in Cycle 1 than in Cycle 2 (FIG. 4h). Tissue inhibitor of metalloproteinases 3 (TIMP3), an inhibitor of MMPs that is enriched in the late secretory phase in the cycling endometrium (Goffin et al., 2003), was induced by decidualization and is expressed most highly at the end of Cycle 2 (FIG. 4h), consistent with a late menstrual cycle enriched expression pattern in vivo. The patterns of MMP9 and TIMP3 expression align with their functions in processing IGFBP1 and inhibition of MMPs respectively. Further, the gradual increase in TIMP3 and decrease in MMP9 expression, as well as the decrease in HAND2 and increase in IGFBP1 after decidualization treatment support the hypothesis that the PSC-ESF are maturing over time.

Finally, we considered GO terms enriched by hormone treatment over vehicle in PSC-ESF in Cycle 1 and Cycle 2. In both Cycle 1 and Cycle 2, there was significant enrichment of GO terms related to response to cAMP, response to estrogen, progesterone metabolic process—consistent with the transduction of hormone signals, as well as terms for placenta development and female pregnancy, supportive of PSC-ESF decidualization (FIG. 9e). However, when we consider the top 10 GO terms enriched for by decidualization in Cycle 1 alone, many of the terms are related to proliferation. By contrast, Cycle 2 top terms were related to hypoxia and progesterone process (FIG. 9f). Taken together, these findings suggest that while hormone responses of PSC-ESF in Cycle 1 and Cycle 2 were largely similar, the distinct expression profiles in each cycle suggest that PSC-ESF reached a more differentiated state at the end of Cycle 2.

Convergence of Gene Expression by PSC-ESF and Primary ESF, and Gain of in Vivo-Like Epithelial and Hormone Signaling after Co-Culture Next we compared the transcriptomic profiles of PSC-ESF from all the time points throughout the differentiation protocol with cultured primary ESF and cultured primary ESF treated for decidualization, first by principle component analysis to assess of the relationships among samples based on their gene expression profiles. We observed a progressive reduction in dissimilarity between PSC-ESF and the ESF control during the differentiation protocol, with day 12 PSC-ESF and the co-cultured PSC-ESF being the least divergent from ESF controls (FIG. 5a).

Co-cultured Cycle 1 and Cycle 2 PSC-ESF are unique in this dataset in that the cells and RNA were collected directly after adherence to epithelial cells rather than cell culture plastic (control ESF), or cell culture plastic coated with Matrigel (day 12 PSC-ESF). To investigate epithelial-stromal interactions, we compared expression of signaling pathway specific transcripts between monolayer control ESF and day 12 PSC-ESF with co-cultured cells without hormone treatment at the end of Cycle 1 and Cycle 2 (FIG. 5b). Specifically, Notch, Indian hedgehog (IHH), and leukemia inhibitory factor (LIF) signaling pathways were selected as they are important signals originating from epithelium to the stroma of the endometrium (Hantak et al., 2014). The monolayer cells in general had lower expression of Notch, LIF, and IHH signaling components when compared to the co-cultured cells. Expression of Notch activating ligands DLL1 and JAG2 as well as transcriptional readouts of activated Notch signaling, HEYL, HEY2, and HES1/2/4, were more highly expressed in the co-cultured cells. LIF receptor (LIFR) was highly expressed in all populations of PSC-ESF. However, downstream mediators such as SOCS3, STAT3, JAK1, and JAK2 were more highly expressed in the co-cultured cells.

Figures 12A, 12B, 12C, 12D:
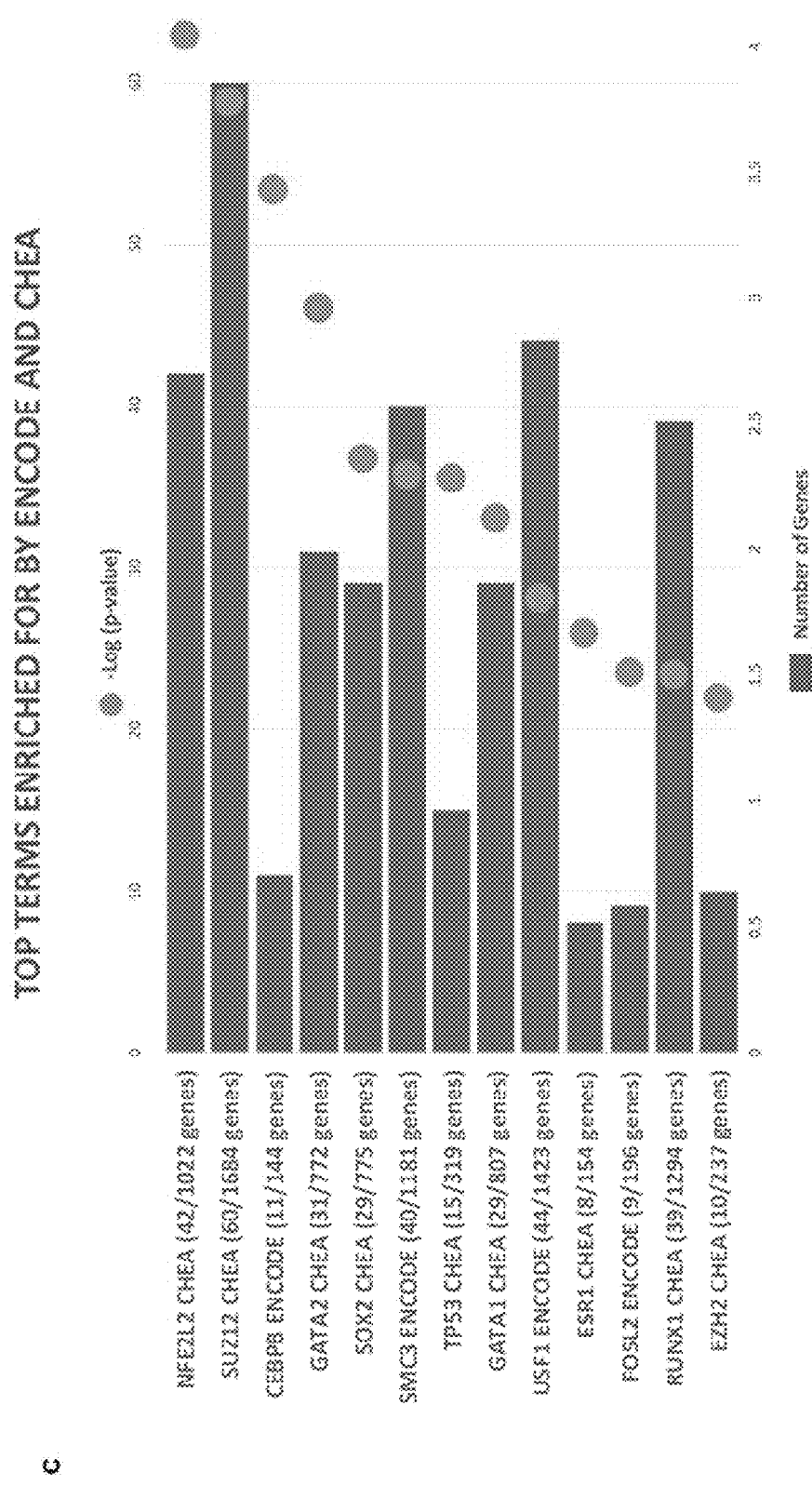
Figures 12A, 12B, 12C, 12D:
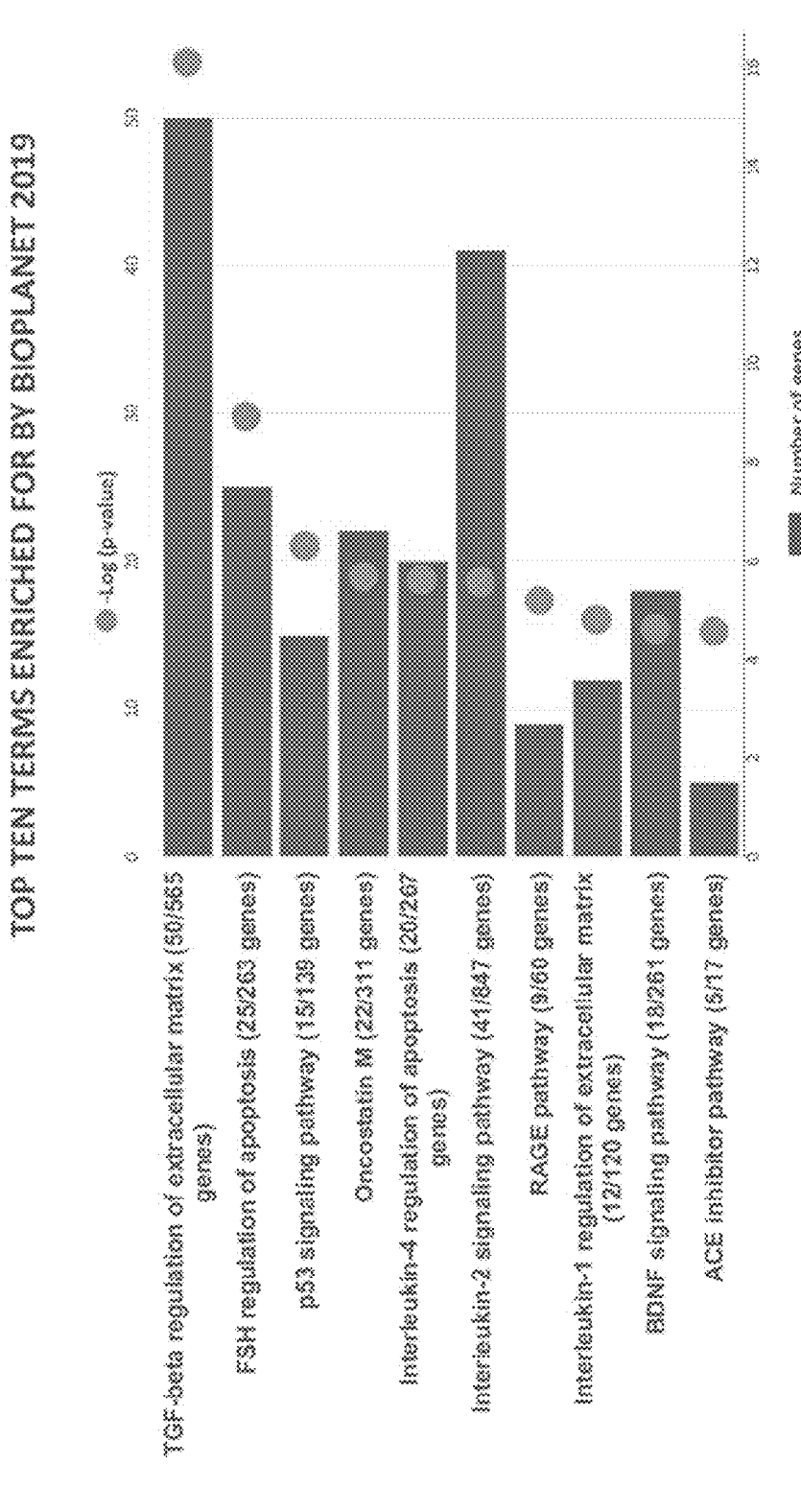

In vivo, IHH signals from the epithelium to the stroma, activating BMP2 expression in ESF (Van Sinderen et al., 2014, Su et al., 2016, Egashira and Hirota, 2013). IHH receptor PTCH1 and SMO as well as downstream signaling proteins GLI3/4 were highly expressed in all populations of PSC-ESF but not in primary ESF control, while mediators PTCH2, HHIP, and STK36 as well as downstream signal GLI1 were gained after co-culture. This gain in hedgehog signaling could be inhibited by the SMO antagonist, cyclopamine, as demonstrated by a reduction in GLI1/2 expression (FIG. 12a, b). Interestingly, we observed high expression of NOTCH 1/3 receptors, LIFR, and IHH receptors SMO and PTCH1 in day 12 PSC-ESF but not in control ESF, and this expression pattern was maintained after co-culture. The expression of these receptors could be one way in which PSC-ESF are primed for co-culture. Together, this analysis suggests that co-cultured PSC-ESF are responsive to epithelial signals.

Next, we wanted to determine the epithelial contribution to PSC-ESF decidualization. We compared genes upregulated in decidualized co-cultured PCS-ESF at Cycle 1 and Cycle 2 over vehicle with genes upregulated in decidualized monolayer control ESF over vehicle. 445 genes were identified to be upregulated by co-culture (FIG. 5c, shared by Cycle 1 and Cycle 2). Using ChIP Enrichment Analysis (ChEA) and the Encyclopedia of DNA Element (ENCODE) database, we found that decidualized co-culture PSC-ESF upregulated genes that shared transcription factor binding sites relevant to decidualization, such as CEBPB, ESR1, and FOLS2 (FIG. 12c) (Gellersen and Brosens, 2014). The NCATS integrated BioPlanet 2019 pathway analysis of the same 445 genes, identified TGF-ß regulation of extracellular matrix as the most enriched pathway (FIG. 12d).

BMP2, a member of the TGF B family, is necessary for decidualization (FIG. 5d). BMP2 in ESF can be activated by hormone treatments, such as P4 and cAMP, which directly increase BMP2 expression to mediate decidualization in hESF (Lee et al., 2007). In the mouse, stromal BMP2 is further amplified indirectly by $P_4$ activated IHH from the luminal epithelium (Lee et al., 2007). Increased stromal BMP2 subsequently mediates decidualization by activating WNT (WNT4) signaling, FK506-binding proteins (FKBP5), and prostaglandin (PTGS1) (Li et al., 2013). To examine the hormone mediated activation of IHH signaling in co-cultured PSC-ESF, we analyzed expression of IHH and BMP signaling targets after decidualization. We found that expression of NR2F2, a transcription factor that mediates IHH activation of BMP2, was gained after co-culture and further amplified by hormone treatment in PSC-ESF (FIG. 5e). HOXA10, a mediator of stromal hormone response, was not increased by co-culture. However, it trended towards an increase after hormone treatment, though without statistical significance (FIG. 5e). Importantly, we observed that BMP2 and BMP2 signaling targets (WNT4, FKBP5, and PTGS1) also were increased in expression in response to co-culture, while BMP2, FKBP5, and PTGS1 were further increased by hormone treatment (FIG. 5e). When we inhibited HH signaling during hormone treatment phase of co-culture with cyclopamine (FIG. 12a), we observed a significant reduction of NR2F2 and well as HOXA10 (FIG. 5f). BMP2 trended towards a reduction, although without statistical significance. Together, these analyses demonstrate the gain of biologically relevant epithelial-stromal and hormone signaling by PSC-ESF in co-culture with EEO.

Overall, our results show that we have successfully differentiated PSC to ESF, and that when co-cultured with EEOs, PSC-ESF respond to epithelial and hormone signals and progressively mature with repeated exposure to decidualization signals.

Discussion

We have described a monolayer differentiation protocol for generating large numbers of highly purified human ESF lineage cells from iPSCs. Moreover, the PSC-ESF generated by this protocol are capable of responding to decidualization signals while maintaining a progenitor potential that enables them to self-organize with primary EEOs to form a 3D, hormone responsive cycling model of the human endometrium. These advances should help to accelerate understanding of the mechanisms underlying normal and abnormal endometrial function.

The marked difference between the biology of the human endometrium and most animal models highlights the need for human models of the cycling endometrium. Human specific studies, using primary ESF and ex vivo explants from endometrial and decidual biopsy, are limited by the restricted group of patients from whom biopsies are readily available which also limits the breadth of genetic backgrounds that can be studied easily (Muruganandan et al., 2020). Moreover, ESF obtained by biopsy cannot be used to explore the earlier events regulating lineage commitment and differentiation of the cells from stem/progenitor cells.

Generation of PSC-ESF from pluripotent stem cells in a stepwise, monolayer protocol thus is an important advance for the study of endometrial development and disease. The relatively high purity and monolayer differentiation of ESF-lineage cells in our protocol will facilitate technically challenging gene-editing studies and analyses investigating development and adult function. Ultimately the ability to generate isogenic ESF for any individual may lead to cell replacement therapies for human disorders.

Upon comparison, we find that our differentiation protocol differs from the embryoid body protocol previously published by Miyazaki, et. al, 2018 in several regards. Of note although both protocols initiate differentiation to ESF with IM induction, we used 4 days of 8 μM CHIR99021 on a monolayer of hPSC, while the previous protocol treated embryoid bodies (EB) with 1.5 days of 5 mM CHIR99021 and 1.5 days of retinoic acid and bFGF. While we did not test the latter, other protocols with IM intermediates suggest that it may be necessary to adjust initial IM induction treatments dependent on cell lines (Morizane et al., 2015). Our monolayer culture approach allowed us to easily quantify the purity of the intermediate progenitors and select for conditions that generate ESF-PSC at the highest efficacy. It is unclear whether cells produced by the Miyazaki protocol would have the ability to self-organize and interact with EEO. Importantly the ability to generate PSC-ESF as a monolayer will facilitate genetic manipulation by viral or transgene transfection of the cells, easy purification or selection of cells, rapid assessment of the effects of experimental treatments, and ultimately transplantation.

PSC-ESF co-cultures with primary EEO from the decidua of term placenta self-organized into organoids that exhibit endometrial markers in the appropriate compartments, organization with appropriate cell-polarity, and hormone responsiveness of both cell types. Prior studies have employed a number of different approaches to study the epithelial-stromal signaling relationship in humans. Reports of EEO establishment, either from endometrial biopsy or from first trimester placenta, all report a purification of the EEO population with the loss of ESF overtime (Turco et al., 2017, Deane et al., 2017, Boretto et al., 2017, Fitzgerald et al., 2019, Haider et al., 2019). Similarly, we found that primary ESF isolated with the EEO from decidua of term placenta, are unable to associate with the EEO in the same culture conditions (FIG. 8c). Further, stromal and mesenchymal stem cells from other organ systems do not associate with EEO to for co-culture. However, primary ESF and primary epithelial cells from endometrial biopsy can aggregate to form hormone responsive spheroids (Wiwatpanit et al., 2020). Another group engineered a collagen scaffold that could support primary ESF and primary epithelial cells seeded on top to simulate the luminal epithelium (Abbas et al., 2020). However, both of these reports relied on primary cells and did not maintain these co-cultures beyond a 14-day hormone cycle or characterize epithelial-stromal signaling.

Our co-culture model could be maintained up to 78 days and responded to hormone treatment, withdrawal, and reapplication. After hormone treatment, Cycle 1 and Cycle 2 PSC-ESF had a very similar decidualization responses. Interestingly, FOXO1 expression in PSC-ESF is nuclear when decidualized in monolayer (FIG. 2h.) whereas decidualization while in co-culture resulted in more cytoplasmic expression. In vivo, FOXO1 expression and localization in ESF is influenced by epithelial progesterone response. Nuclear FOXO1 expression is characteristic of mid secretory dESF while cytoplasmic FOXO1 is characteristic of late secretory dESF, suggesting that hormone treatment while in co-culture resulted in a later decidualization state (Vasquez et al., 2018).

We also observed that Cycle 2 expressed a greater number of decidualization markers, and there was an increase over time in expression of genes relevant to regulation of decidualization, such as IGFBP1. Further, by cycle 3 there was a continued enrichment for decidualization markers with reduced proliferation. This suggests that the progenitor population may be progressively depleted in the co-cultures in the absence of a stem cell population capable of repleting the progenitors. The expression pattern of IGF, MMP, and TIMP family members we observed in Cycle 1 vs. Cycle 2 (FIG. 4h) is consistent with enrichment for proliferation in cycle 1 compared to the subsequent cycles. Importantly, the proliferation responses to both cycles of hormone treatment and withdrawal matched what is found using human endometrial biopsies as well as mouse models of menses and repair (Vaskivuo et al., 2000, Armstrong et al., 2017). While characterization and further optimization of the co-culture beyond Cycle 2 is needed, our model should be an invaluable resource for studying molecular mechanisms of various etiologies of amenorrhea and endometriosis (Nawaz and Rogol, 2020, Scotti et al., 2000).

Previous work has established that early in development stromal cells direct Müllerian epithelial cell fate. Similar experiments conducted using adult mouse grafts found that vaginal epithelial cell plasticity is lost (Cunha, 1976). Our findings demonstrate epithelial to stromal signaling in the endometrial co-cultures. It is possible that bidirectional signaling occurs in adult cycling decidua, reflecting a maturation process that differs from early developmental events that specify lineage commitment. Recent scRNAseq studies of human first trimester placenta has catalogued expression of receptor-ligand pairs in epithelial and stromal cells (Vento-Tormo et al., 2018). Further, several pathways of importance have been described extensively in mouse models of decidualization (Gellersen and Brosens, 2014). Our analysis of hormone induced epithelial IHH to stromal BMP2 signaling offers an example of how our current data set and model can be used synergistically with these studies to identify putative signals that influence human endometrial function and disease.

The endometrial epithelial-stromal cell signaling relationship appears to be important for the maintenance and differentiation of either ESF progenitors/stem cells, or bipotent endometrial stem cells (Yin et al., 2019, Jin, 2019, Saatcioglu et al., 2019). Interestingly, analysis of genes enriched in co-cultured PSC-ESF compared to monolayer cultures identified an enrichment for SOX2 transcription factor binding sites (FIG. 12c). SOX2 expression is associated with pluripotency and ectoderm lineages, however, SOX2 expression has also been described in CD146+PDG-FRb+ putative adult endometrial mesenchymal stem cell (eMSC)populations (Schuring et al., 2011, Schwab and Gargett, 2007). Analysis of gene expression across all differentiation and co-culture time points revealed that SUSD2, a widely used eMSC marker, was expressed mostly highly at day 8 of differentiation (FIG. 7h), a time at which the cells were highly proliferative. Our co-culture studies performed with day 12 PSC-ESF cells appear to demonstrate limited cycling capacity, as demonstrated by the progressive reduction in proliferative Ki67+ cells and maintenance of decidualization markers with increasing cycle number. This suggests a progressive transition from an early stem/progenitor cell to a more committed precursor and finally differentiated stroma. Future PSC-ESP and EEO co-culture experiments with day 8 PSC-ESP will determine whether the presence of less committed PSC-ESP enhance and extend cyclic hormone responses in co-cultures. Another important future application of the described protocol is the possibility that the maturation treatment could be applied or adapted for maturation of other adult progenitor populations, such as eMSC.

We expect that our model will facilitate mechanistic studies of reproductive disease-related genes as identified by animal models and, importantly, human GWAS and gene regulatory mapping studies (Hallman et al., 2019, Zondervan et al., 2016, Sakabe et al., 2020). For example, recent studies have reported that a novel causal locus and candidate gene, HAND2, is associated with gestational length (Sakabe et al., 2020). During decidualization, HAND2 expression is increased by the stromal population to regulate epithelial cell proliferation and differentiation to prepare for implantation. We describe an increase in HAND2 in our PSC-ESF in response to decidualization while co-cultured with EEO. Future studies could characterize how changing expression of HAND2 in PSC-ESF affects the decidualization profile of PSC-ESF, the function of epithelial cells, and the interaction between the two cell populations.

Finally, human implantation and subsequent placentation have never been studied in vitro. We believe that our report is a first step in the study of these unique, yet elusive processes. The model we characterized could be the scaffold for the addition of the luminal epithelial cells so that the appropriate implantation interface, as well as signaling could be studied. Stromal-epithelial cross talk as well cyclic responses to hormone treatment present an exciting start for the study of even more complex interactions with co-cultured placenta trophoblasts or eventually blastocysts Materials and Methods Monolayer Cell Culture and Differentiation: Both embryonic (H7) and iPS (reprogrammed from Coriell fibroblast GM03651 by Sendai virus (ThermoFisher #A16517) following manufacturer's instruction) cells lines of female origin (XX) were used for differentiation as well as co-culture. Cells were cultured in mTeSR1 media (STEMCELL Technologies #85875) and on Corning Matrigel hESC-Qualified Matrix (Corning™ #354277) coated tissue culture plastic plates. Lot specific dilution factor volume provided by the manufacturer is diluted into 24 mL of cold DMEM/F12 (ThermoFisher Scientific #11320-082). To coat: 1 mL of this solution is applied to 1 well of a 6 well plate (9.6 cm$^2$) and incubated at RT for 1 hr or 37 C for 30 min. To differentiate, PSC were dissociated to single-cell level using Accutase (EMD Millipore #SCR005). Once at single cell level, equal volume mTeSR1 was added to stop dissociation and cells were pelleted at 0.2e3 rcf for 5 min. Supernatant was discarded and the remaining pellet of PSC was resuspended in mTeSR1 and 10 μM Y27632 (Reprocell #04-0012-02) and plated onto Corning Matrigel hESC-Qualified Matrix coated tissue culture plates at 3×10$^5$ per 3.8 cm$^2$ or equivalent density. Media is replaced with Differentiation Basal Media (Advanced RPMI 1640 (Gibco #12633020), 1× Gluatmax (Gibco #35050061) and 804 CHIR99021 (STEMCELL Technologies #72054). After 4 days, the media is changed to Differentiation Basal Media containing 100 ng/mL recombinant Human WNT7A (R&D Systems #3008-WN-025). The final differentiation treatment media was Differentiation Basal Media with 10 ng/mL Recombinant Human BMP2 (R&D Systems #355-BM010), and 10 nM β-estradiol (E$_2$, Millipore Sigma #E2758-250MG). While it varies by cell line, the expected yield at day 12 off differentiation when starting with 3×10$^5$ stem cells is 0.6×10$^6$-13.2×10$^6$ PSC-ESF.

To passage, differentiated cells were dissociated using Accutase and pelleted at 0.2×10$^3$ rcf for 5 min. The supernatant was discarded, and the remaining pellet of PSC was resuspended in Differentiation Basal Media at a density of 3×10$^6$ per 2 cm$^2$ on Corning Matrigel hESC Qualified Matrix coated plates. Cells can be maintained in Differentiation Basal Media for up to 3 passages for monolayer decidualization.

For decidualization treatment, cells are pretreated with 10 nM E$_2$ in DMEM/F12, no phenol red (ThermoFisher Scientific #21041025), 1× Glutamax, and 1×ITS-A (ThermoFisher Scientific #51300044) for 1 day. Then media is changed to contain 2% charcoal stripped FBS (ThermoFisher Scientific #12676029). Decidualization treatment media contained 0.5 mM 8-BrcAMP (Tocris #1140), 1 μM Medroxyprogesterone 17-acetate (Millipore Sigma #M1629), and 10 nM E$_2$. Vehicle media contained equal volume of EtOH (Millipore Sigma #E7023) and Cell Culture Grade Water (Corning #25055CVC).

To freeze cells for storage long term, PSC-ESP at day 8 of differentiation were dissociated using Accutase and pelleted at $0.2 \times 10^3$ rcf for 5 min. A minimum of $2 \times 10^6$ cells are resuspended in 1 mL Recovery Cell Culture Freezing Medium (ThermoFisher Scientific #12648010) and transferred to a cryovial (ThermoFisher Scientific #377224). To thaw, cryovials are removed from liquid nitrogen storage and placed directly into 37 C water bath for <1 min. Directly mix the thawed cells in Differentiation Basal Media prior to pelleting, spin at $0.2 \times 10^3$ rcf for 5 min. Resuspend the pellet in Differentiation Basal Media and plate at a density of $2 \times 10^6$ cells per 9.6 cm$^2$ on Matrigel coated plates. Continue with differentiation from day 8. Organoid Cell Culture: Endometrial epithelial organoids isolated from term placenta were maintained as published in the literature (Marinic et al., 2020, Turco et al., 2017). Briefly, decidual tissue was minced in a dish, followed by digestion in collagenase V (0.4 mg/ml)/dispase II (1.25 U/ml) solution (Sigma #C9263 and #D4693) in RPMI-1640 (ThermoFisher Scientific #11875127) with 10% Fetal Bovine Serum (Thermo Fisher Scientific, 26140-079) for at least 20 min at 37° C. with shaking. Once glands are loosened from the tissue, the digestion was stopped by dilution with RPMI-1640. The digest was filtered through several 100 μm sieves. Larger gland elements were collected by inverting the sieves over the Petri dish and washing them off. The glands were collected in low binding tubes (Eppendorf #022431081) and pelleted by centrifugation at $0.6 \times 10^3$ rcf for 6 min, re-suspended in Advanced DMEM/F12 (Thermo Fisher Scientific #12634010) and pelleted again. After removing the supernatant, gland elements were mixed with 20× volume of phenol red free Matrigel at a 100% concentration (Corning #356231). 20-25 μl droplets were plated per well of a 48-well plate (Thomas Scientific #1156F01). They were put in the humidified cell culture incubator at 37° C. and 5% CO$_2$ to solidify for 15 min, overlaid with 250 μl of organoid media (Turco et al., 2017) and returned to the incubator. Organoid media contains 1× N2 supplement (ThermoFisher Scientific #17502048), 1× B27 supplement minus vitamin A (ThermoFisher Scientific #12587010), 100 ug/mL Primocin (Invivogen #ant-pm-1), 1.25 mM N-Acetyl-L-cysteine (Sigma #A9165-5G), 1× Glutamax (Gibco #35050061), 50 ng/mL recombinant human EGF (Peprotech #AF-100-15), 100 ng/mL recombinant human Noggin (Peprotech #120-10C), 500 ng/mL recombinant human Rspondin-1 (Peprotech #120-38-50 UG), 100 ng/mL recombinant human FGF-10 (Peprotech #100-26-25UG), 50 ng/mL recombinant human HGF (Peprotech #100-39H-25UG), 500 nM A83-01 (R&D Systems #2939/10), 10 nM Nicotinamide (Sigma #N0636) in Advanced DMEM/F12 (ThermoFisher Scientific #12634010) and was exchanged every 3 days.

To prepare for co-culture, the organoids were treated as though for passaging (Turco et al., 2017). In brief, matrigel domes and organoids were collected and dissociated by manual trituration (300×), diluted with Advanced DMEM/F12, and pelleted by centrifugation at $0.6 \times 10^3$ rcf for 6 min. The pellet was resuspended in 1004, of Advanced DMEM/F12 and the dissociation (80×), dilution, and pelleting was repeated. Approximately 3-4 organoids 500-800 um in size are fragmented by manual titration 300×, followed by an additional 80×. Size of fragments were not entirely uniform. The fragmented 3-4 organoids were split at a 1:3-1:5 ratio by resuspension into 60-1004, of 100% Matrigel. 20-254, of organoid+Matrigel is mixed with $1.5 \times 10^5$ of freshly derived PSC-ESF, of ESC or iPSC origin, and plated as described above. Organoid media was adapted for co-culture and is referred to as expansion media (ExM). ExM contains 1× N2 supplement (ThermoFisher Scientific #17502048), 1× B27 supplement minus vitamin A (ThermoFisher Scientific #12587010), 100 ug/mL Primocin (Invivogen #ant-pm-1), 1.25 mM NAcetyl-L-cysteine (Sigma #A9165-5G), 1× Glutamax (Gibco #35050061), 50 ng/mL recombinant human EGF (Peprotech #AF-100-15), 500 ng/mL recombinant human Rspondin-1 (Peprotech #120-38-50UG), 100 ng/mL recombinant human FGF-10 (Peprotech #100-26-25UG), 50 ng/mL recombinant human HGF (Peprotech #100-39H-25UG), 500 nM A83-01 (R&D Systems #2939/10), 10 nM Nicotinamide (Sigma #N0636) in Advanced DMEM/F12 (ThermoFisher Scientific #12634010).

To cyclically treat the co-cultures: After 14 days of treatment, the co-culture was replated to prepare for prolonged culture. To replate: Spent media was replaced with 5004, Cell Recovery Solution (Fisher Scientific #CB-40253) per well of a 48-well plate (Denville Scientific #1156F01). The entire plate was incubated on ice for 1 hr to dissolve the Matrigel. The co-culture solution was collected and spun down at $0.6 \times 10^3$ rcf for 6 min. The supernatant was removed, and the pellet was resuspended in 20-254, of fresh phenol-red free Matrigel to be plated in a well of a 48-well plate. During the first 10 days, the co-cultures were maintained free of hormone treatment in ExM. To start cycle 2, co-cultures were treated with the same decidualization paradigm with 2 days of 10 nM E$_2$ followed by 14 days of 0.5 mM 8-Br-cAMP, 1 μM MPA, and 10 nM E$_2$. The co-cultures were replated in hormone free ExM for 10 days, after which, the same 16 days decidualization treatment was applied to reach Cycle 3. Primary Cell Cultures: Deindentified primary ESF cultures were established from fresh endometrial biopsies and provided to us by the Serdar Bulun lab to use as controls for qPCR during protocol development and controls for organoid co-culture. Primary ESF are cultured in media containing DMEM/F12, 10% Hyclone FBS (Fisher Scientific #SH3007003), and 1× Glutamax and used for experiments before passage 6. Bone marrow derived mesenchymal stem cells of female origin (XX) were purchased from ATCC (ATCC® PCS-500-012). Cells were cultured in MSCGM Mesenchymal Stem Cell Growth Medium BulletKit (LONZA #PT-3001) and used for experiment before passage 3. Human dermal stromal fibroblasts of female origin (XX, GM03651) used for iPSC reprogramming were cultured in media containing DMEM/F12, 10% Hyclone FBS, and 1× Glutamax and used for experiment before passage 5. All three primary cells were handled separately and were mixed with EEO for co-culture at the same ratio of $1.5 \times 10^5$ cells per 20-254, of organoid+Matrigel and plated as described above. Primary cell and organoid cultures were maintained for up to 26 days. Representative images from day 10 are shown.

qRT-PCR: RNA Isolation was performed using the RNAqueous-Micro Total RNA Isolation Kit (ThermoFisher Scientific #AM1931) following manufacturer's instructions. DNAse treatment and reverse transcription were performed using SuperScript IV VILO Master Mix with ezDNase Enzyme (ThermoFisher Scientific #11766050) following manufacturer's instructions. Quantitative PCR was performed using SYBR Green PCR Master Mix (ThermoFisher Scientific #4312704) using the QuantStudio 7. ESC and iPSC differentiated cells were used for analysis. A list of primers can be found in Table 1.

TABLE 1

| | Primers | | | |
|---|---|---|---|---|
| Gene | Forward Primer | Seq. ID NO: | Reverse Primer | Seq. ID NO: |
| GAPDH | ACACCATGGG GAAGGTGAAG | 1 | GTGACCAGGC GCCCAATA | 2 |
| BRACHYURY | GCCCTCTCCC TCCCCTCCAC GCACAG | 3 | CGGCGCCGTT GCTCACAGAC CACA GG | 4 |
| LHX1 | ATGCAACCTG ACCGAGAAGT | 5 | CAGGTCGCTA GGGGAGATG | 6 |
| PAX2 | GCAACCCCGC CTTACTAAT | 7 | AACTAGTGGC GGTCATAGGC | 8 |
| OCT3/4 | GAC AGG GGG AGG GGA GGA GCT AGG | 9 | CTT CCC TCC AAC CAG TTG CCC CAA AC | 10 |
| SOX2 | GGGAAATGGG AGGGGTGCAA AAGAGG | 11 | TTGCGTGAGT GTGGATGGGA TTGGTG | 12 |
| SOX17 | CGCTTTCATG GTGTGGGCTA AGGACG | 13 | TAGTTGGGGT GGTCCTGCAT GTGCTG | 14 |
| AMHR2 | CGACCACATT GTCCGATTTA TCA | 15 | CCCTTGGGAT GCAGTTCCA | 16 |
| WNT7A | CTGTGGCTGC GACAAAGAGA A | 17 | GCCGTGGCAC TTACATTCC | 18 |
| HOXA9 | TACGTGGACT CGTTCCTGCT | 19 | CGTCGCCTTG GACTGGAAG | 20 |
| HOXA10 | CTCGCCCATA GACCTGTGG | 21 | GTTCTGCGCG AAAGAGCAC | 22 |
| HOXA11 | CGGCCACACT GAGGACAA | 23 | CTGAAGAAGA ACTCCCGTTC CA | 24 |
| HOXA13 | CTGCCCTATG GCTACTTCGG | 25 | CCGGCGGTAT CCATGTACT | 26 |

TABLE 1-continued

| | Primers | | | |
|---|---|---|---|---|
| Gene | Forward Primer | Seq. ID NO: | Reverse Primer | Seq. ID NO: |
| PGR | AGCCAAGAAG AGTTCCTCTG TA | 27 | TTGACTTCGT AGCCCTTCCA | 28 |
| PRL | CATCAACAGC TGCCACACTT | 29 | CGTTTGGTTT GCTCCTCAAT | 30 |
| FOXO1 | TGATAACTGG AGTACATTTC GCC | 31 | CGGTCATAAT GGGTGAGAGT CT | 32 |
| IGFBP1 | CTATGATGGC TCGAAGGCTC | 33 | TTCTTGTTGC AGTTTGGCAG | 34 |
| GLI1 | CCAACTCCAC AGGCATACAG GAT | 35 | CACAGATTCA GGCTCACGCT TC | 36 |
| GLI2 | AAGTCACTCA AGGATTCCTG CTCA | 37 | GTTTTCCAGG ATGGAGCCAC TT | 38 |
| NR2F2 | TCATGGGTAT CGAGAACATT TGC | 39 | TTCAACACAA ACAGCTCGCT C | 40 |
| BMP2 | GGAACGGACA TTCGGTCCTT | 41 | CACCATGGTC GACCTTTAGG A | 42 |

Immunoblotting: Cellular proteins were solubilized in M-PER (Bio-Rad) and protein concentrations were determined by Pierce BCA protein Assay kit (ThermoFisher Scientific #23227), subjected to electrophoresis on 4-15% polyacrylamide gels (Bio-Rad #4561085), transferred to PVDF (Millipore #IPVH00010), and blocked with Blotto (Santa Cruz Biotechnology #2325) in Tris-Buffered Saline (Bio-Rad #1706435). Primary antibodies (Table 2) for PR, ERβ, and GAPDH. Secondary antibodies were goat-anti-rabbit-HRP (CST #7074S), horse-anti-mouse-HRP (CST #7076. Membranes were incubated with enhanced chemiluminescent substrate (Thermo Fisher #34095) and developed using Azure c600 Imager. Quantitation of blots was performed with ImageJ (NIH). ESC and iPSC differentiated cells were used for analysis.

TABLE 2

| | Antibodies | | | | | |
|---|---|---|---|---|---|---|
| Protein | Source | Species | Catalog # | ICC-monolayer | ICC-organoid sections | WB |
| Ck-IgY control (1 mg/mL) | R&D Systems | Ck-IgY | AB-101-C | 1:2000 | 1:4000 | |
| Gt-IgG control 0.4 mg/mL | Santa Cruz Biotechnologies | Gt-IgG | sc-2028 | 1:500 | 1:400 | |
| Ms-IgG control (1 mg/mL) | Santa Cruz Biotechnologies | Ms-IgG | sc-2025 | 1:100 | 1:100 | |
| Rb-IgG control (5 mg/mL) | Abcam | Rb-IgG | ab37415 | 1:500 | 1:5000 | |
| Acetylated α-Tubulin | Millipore Sigma | Ms-IgG2b | T7451 | | 1:800 | |
| AMHR2 | Abcam | Ms-IgG1 | ab64762 | 1:5000 | 1:5000 | |

TABLE 2-continued

Antibodies

| Protein | Source | Species | Catalog # | ICC-monolayer | ICC-organoid sections | WB |
|---|---|---|---|---|---|---|
| Cleaved Caspase 3 | Cell Signaling Technologies | Rb-IgG | 9661 | | 1:400 | |
| connexin43 | Santa Cruz Biotechnologies | Ms-IgG2a | sc-271837 | 1:50 | 1:50 | |
| E-cadherin | Cell Signaling Technologies | Rb-IgG | 3195S | | 1:50 | |
| EpCam | Cell Signaling Technologies | Ms-IgG1 | 2929S | | 1:500 | |
| Estrogen Receptor beta 1 | Abcam | Ms-IgG2a | ab187291 | | | 1:400 (0.5 ug/mL) |
| FOXA2 (HNF-3β) | Santa Cruz Biotechnologies | Ms-IgG1 | sc-271103 | | 1:50 | |
| FOXO1 | Cell Signaling Technologies | Ms-IgG1 | 14952S | 1:100 | 1:100 | |
| GAPDH | Milipore Sigma | Ms-IgG1 | MAB374 | | | 1:2000 |
| Hand2 | Abcam | Rb-IgG | ab200040 | 1:100 | 1:500 | |
| phospho-Histone H3 | Upstate | Rb-IgG | 06-570 | | 1:1000 | |
| HOXA10 | Sino Biological | Rb-IgG | 103169-T08-100 | | 1:5000 | |
| HOXA11 | ThermoFisher Scientific, Invitrogen | Rb-IgG | PA5-57341 | 1:1000 | 1:1000 | |
| IGFBP1 | Peprotech | Rb-IgG | 350-10 | | 1:2500 | |
| Ki67 | MilliporeSigma | Ms-IgG1 | MAB4190 | 1:500 | 1:50 | |
| Laminin | MilliporeSigma | Rb-IgG | L9393 | | 1:500 | |
| OCT 3/4 (N-19) | Santa Cruz Biotechnologies | Gt-IgG | sc-8628 | 1:500 | | |
| PAX2 | Abcam | Rb-IgG | ab79389 | 1:500 | | |
| PDGFRβ | Abcam | Rb-IgG | ab32570 | | 1:1000 | |
| PR | Abcam | Rb-IgG | ab16661 | | 1:400 | 1:200 |
| VIM | MilliporeSigma | Ck-IgY | AB5733 | 1:1000 | 1:2000 | |

Immunocytochemistry: Monolayer cultures: cells cultured on Matrigel coated coverslips were washed with 1×DPBS (Corning #21031CV) before fixing the cells using 4% Formaldehyde solution (Millipore Sigma #P6148) for 20 min at room temperature. After 20 min, cells are washed 3 times with 1×DPBS. Prior to staining, cells were blocked for 1 hr at RT in PBS (Fisher Scientific #AM9625), 0.1% BSA (Millipore Sigma #A7906), 0.25% Triton-X (Millipore Sigma #T8787), and 10% Normal Goat Serum (Jackson Immuno Research #005-000-121). Primary Antibodies were diluted into the same buffer for incubation at 4° C. overnight. Coverslips were washed 3 times with PBS, then incubated at RT for 1 hr with secondary antibodies and Hoechst (ThermoFisher Scientific #H3569) diluted 1:2000 in the blocking buffer. Stained sections were mounted in ProLong Gold (Molecular Probes #P36930). Images were acquired with a Leica SP5 confocal microscope. Isotype dilutions were determined based off of the highest primary antibody concentration used for the given species. Organoid Co-cultures: Organoids were recovered from Matrigel as previously describe and fixed in 4% Formaldehyde for 1 hr at 4° C. After washing 3 times with PBS, the organoids were cryoprotected in 30% sucrose for 1 hr to overnight at 4° C. The organoids were collected and embedded in OCT matrix (Tissue-Tek) and sectioned on a cryostat (Leica CM3050S) at 8 μm thickness and collected on microscope slides. Sections were washed with PBS and blocked with blocking media (10% Normal Goat Serum 1% BSA and 0.25% Triton-X) for 1 hr at room temperature. Primary antibodies were diluted in blocking media to incubate overnight at 4°

C. Sections were washed 3 times with PBS, then incubated at RT for 1 hr with secondary antibodies and Hoechst (ThermoFisher Scientific #H3569) diluted 1:2000 in the blocking buffer. Stained sections were mounted in ProLong Gold (Molecular Probes #P36930). Images were acquired with a Leica SP5 confocal microscope. Isotype dilutions were determined based off of the highest primary antibody concentration used for the given species (FIG. 13). ESC and iPSC differentiated cells were used to confirm expression patterns in both monolayer and co-culture. A list of antibodies used is available in Table 2.

In Situ Hybridization: WNT5A transcripts in co-culture organoids with ESC differentiated PSC-ESF were detected using the RNAscope Multiplex Fluorescent Reagent Kit v2 Assay following manufacturer's protocol for Fixed frozen tissue. Pretreatment was optimized for organoid sections as follows. Slides were washed with 1×PBS and incubated with 5-8 drops of RNAscope Hydrogen Peroxide at RT for 10 min followed by washing 3-5 times with distilled water. Slides were then treated with 3-5 drops of Protease III and incubated for 30 min at 40° C. using the HybEZ Oven, followed by 3-5 washed with distilled and proceeding with the manufacture's protocol for the RNAscope Assay as published. WNT5A probe (#604921) was visualized on the Cl channel and TSA Plus fluorescein at 1:1000 dilution. Sections were also counterstained with ~3-5 drops of Hoechst (ThermoFisher Scientific #H3569) for 30 s at RT. Remove Hoechst and mount the sections in ProLong Gold for imaging on a Leica SP5 confocal microscope. The fluorescent puncta associated with WNT5A transcripts were quantified using a modified speckle-counting pipeline with Cell-Profiler (v4.1.3, https://cellprofiler.org), as labeled by RNAscope in situ hybridization (ACDBio).

Cell Density Analysis: Bright phase images were acquired with the CoolSNAP Dyno camera (Digital Imaging Systems). Using Image J, images were Inverted and the Radial Profile Angle Plugin was applied. Average signal intensity values were obtained from the center to 500 pixels radially outward for each organoid. Signal intensity values were normalized to the center value. 3 organoids were quantified for each time point presented; 9 organoids were quantified total. ESC and iPSC differentiated cells were used for this analysis and quantification.

RNAseq: RNA Isolation: RNAeasy Minikit (Qiagen #74104) was used to isolated RNA from ESC differentiated cells for sequencing. Monolayer cells were dissociated to single cell suspension using Accutase and pelleted. RNA was isolated following manufacturers protocol. pLOC-Tur-boRFP (Horizon) used to transduce constitutive RFP expression in PSC derived cells. The virus was added to adherent cultures with 4 ug/mL of polybrene (EMD Millipore #TR-1003-G) in differentiation media. The next day, media containing virus was removed and replaced with fresh differentiation media. The day after, cells were dissociated to a single-cell suspension to be sorted by FACS. RFP+ cells were collected, pelleted, and RNA was isolated following manufacturers protocol. RNA quality was accessed by a Bioanalyzer 2100 (Agilent technology) with a RIN value cutoff of 6.9.RNA-seq libraries were generated by TruSeq stranded total RNA library prep kit (Illumina) and TruSeq RNA CD Index Plate. Differential expression: Read counts per gene and TPMs were calculated with Salmon (Patro et al., 2017) version 0.12.0. The transcript set was obtained from Gencode GRCh37 (https://www.gencodegenes.org/). Estimated counts were used in exploratory analysis (transformed with DESeq2's rlog function for principal component analysis) and in DESeq2 (Love et al., 2014) version 1.24.0 to identify differentially expressed genes (adjusted p-value≤0.05 and absolute fold-change of ≥2). Svaseq (Leek, 2014) identified 6 surrogate variables that were used in the DESeq2 analysis. The heatmaps show Z-scores of mean TPMs per gene. All comparisons can be found in Supplementary File 1 (data not shown).

Gene Ontology: The human Gene Ontology (GO) associations of GO terms (Ashburner et al., 2000) to genes and the GO database were downloaded on Jan. 22, 2016 from http://geneontology.org/geneassociations and terms and parent terms were assigned to Gencode GRCh37 genes. A hypergeometric test was used to calculate the statistical significance of the difference of the number of genes associated with a given GO term in a particular gene set and the universe of all genes (p<0.05). p-Values were corrected with the R package p.adjust function using the ide method. NCATS Bioplanet 2019, CHEA, and ENCODE: The NCATS Bioplanet 2019 (Huang et al., 2019), CHEA (Lachmann et al., 2010), and ENCODE (Consortium, 2011) enrichment analysis were completed using Enrichr, an online resource tool. (Chen et al., 2013, Kuleshov et al., 2016).

Statistical Analysis: Data was analyzed using GraphPad Prism software (version 8.4.3), and statistical significance was assigned at a predetermined cutoff of p<0.05. Comparisons between pairs of experimental groups were performed using Student's t-test. Comparisons between three or four groups were done using One-way Anova with Tukey's paired comparisons test for correction for multiple comparisons. Statistical tests are indicated in the figure legends.

Sample number as indicated in the figure legends (n=x) represent independent experiments. For coculture experiments, a sample number (n), represents an independent experiment containing multiple individual organoid+ PSC-ESF co-cultures. All data are presented as mean±standard error of the mean (SEM).

REFERENCES

ABBAS, Y., BRUNEL, L. G., HOLLINSHEAD, M. S., FERNANDO, R. C., GARDNER, L., DUNCAN, I., MOFFETT, A., BEST, S., TURCO, M. Y., BURTON, G. J. & CAMERON, R. E. 2020. Generation of a three-dimensional collagen scaffold-based model of the human endometrium. Interface Focus, 10, 20190079.

AGHAJANOVA, L., HAMILTON, A., KWINTKIEWICZ, J., VO, K. C. & GIUDICE, L. C. 2009. Steroidogenic enzyme and key decidualization marker dysregulation in endometrial stromal cells from women with versus without endometriosis. Biol Reprod, 80, 105-14.

ARMSTRONG, G. M., MAYBIN, J. A., MURRAY, A. A., NICOL, M., WALKER, C., SAUNDERS, P. T. K., ROSSI, A. G. & CRITCHLEY, H. O. D. 2017. Endometrial apoptosis and neutrophil infiltration during menstruation exhibits spatial and temporal dynamics that are recapitulated in a mouse model. Sci Rep, 7, 17416.

ASHBURNER, M., BALL, C. A., BLAKE, J. A., BOTSTEIN, D., BUTLER, H., CHERRY, J. M., DAVIS, A. P., DOLINSKI, K., DWIGHT, S. S., EPPIG, J. T., HARRIS, M. A., HILL, D. P., ISSEL-TARVER, L., KASARSKIS, A., LEWIS, S., MATESE, J. C., RICHARDSON, J. E., RINGWALD, M., RUBIN, G. M. & SHERLOCK, G. 2000. Gene ontology: tool for the unification of biology. The Gene Ontology Consortium. Nat Genet, 25, 25-9.

BORETTO, M., COX, B., NOBEN, M., HENDRIKS, N., FASSBENDER, A., ROOSE, H., AMANT, F., TIMMERMAN, D., TOMASSETTI, C., VANHIE, A., MEULEMAN, C., FERRANTE, M. & VANKELECOM, H. 2017. Development of organoids from mouse and human endometrium showing endometrial epithelium physiology and long-term expandability. Development, 144, 1775-1786.

CHEN, E. Y., TAN, C. M., KOU, Y., DUAN, Q., WANG, Z., MEIRELLES, G. V., CLARK, N. R. & MA'AYAN, A. 2013. Enrichr: interactive and collaborative HTML5 gene list enrichment analysis tool. BMC Bioinformatics, 14, 128. CONSORTIUM, E. P. 2011. A user's guide to the encyclopedia of DNA elements (ENCODE). PLoS Biol, 9, e1001046. COPPOCK, H. A., WHITE, A., APLIN, J. D. & WESTWOOD, M. 2004. Matrix metalloprotease-3 and -9 proteolyze insulin-like growth factor-binding protein-1. Biol Reprod, 71, 438-43.

CUNHA, G. R. 1976. Stromal induction and specification of morphogenesis and cytodifferentiation of the epithelia of the Müllerian ducts and urogenital sinus during development of the uterus and vagina in mice. J Exp Zool, 196, 361-70.

DEANE, J. A., COUSINS, F. L. & GARGETT, C. E. 2017. Endometrial organoids: in vitro models for endometrial research and personalized medicine. Biol Reprod, 97, 781-783.

DU, H. & TAYLOR, H. S. 2015. The Role of Hox Genes in Female Reproductive Tract Development, Adult Function, and Fertility. Cold Spring Harb Perspect Med, 6, a023002.

41

EGASHIRA, M. & HIROTA, Y. 2013. Uterine receptivity and embryo-uterine interactions in embryo implantation: lessons from mice. Reprod Med Biol, 12, 127-132.

FITZGERALD, H. C., DHAKAL, P., BEHURA, S. K., SCHUST, D. J. & SPENCER, T. E. 2019. Selfrenewing endometrial epithelial organoids of the human uterus. Proc Natl Acad Sci USA, 116, 23132-23142.

FULLERTON, P. T., JR., MONSIVAIS, D., KOMMAGANI, R. & MATZUK, M. M. 2017. Follistatin is critical for mouse uterine receptivity and decidualization. Proc Natl Acad Sci USA, 114, E4772-E4781.

GANEFF, C., CHATEL, G., MUNAUT, C., FRANKENNE, F., FOIDART, J. M. & WINKLER, R. 2009. The IGF system in in-vitro human decidualization. Mol Hum Reprod, 15, 27-38.

GELLERSEN, B. & BROSENS, J. J. 2014. Cyclic decidualization of the human endometrium in reproductive health and failure. Endocr Rev, 35, 851-905.

GOFFIN, F., MUNAUT, C., FRANKENNE, F., PERRIER D'HAUTERIVE, S., BELIARD, A., FRIDMAN, V., NERVO, P., COLIGE, A. & FOIDART, J. M. 2003. Expression pattern of metalloproteinases and tissue inhibitors of matrix-metalloproteinases in cycling human endometrium. Biol Reprod, 69, 976-84.

GURUNG, S., WILLIAMS, S., DEANE, J. A., WERKMEISTER, J. A. & GARGETT, C. E. 2018. The Transcriptome of Human Endometrial Mesenchymal Stem Cells Under TGFbetaR Inhibition Reveals Improved Potential for Cell-Based Therapies. Front Cell Dev Biol, 6, 164.

HAIDER, S., GAMPERL, M., BURKARD, T. R., KUNIHS, V., KAINDL, U., JUNTTILA, S., FIALA, C., SCHMIDT, K., MENDJAN, S., KNOFLER, M. & LATOS, P. A. 2019. Estrogen Signaling Drives Ciliogenesis in Human Endometrial Organoids. Endocrinology, 160, 2282-2297. HALLMAN, M., HAAPALAINEN, A., HUUSKO, J. M., KARJALAINEN, M. K., ZHANG, G., MUGLIA, L. J. & RAMET, M. 2019. Spontaneous premature birth as a target of genomic research. Pediatr Res, 85, 422-431.

HANTAK, A. M., BAGCHI, I. C. & BAGCHI, M. K. 2014. Role of uterine stromal-epithelial crosstalk in embryo implantation. Int J Dev Biol, 58, 139-46.

HEMBERGER, M., HANNA, C. W. & DEAN, W. 2020. Mechanisms of early placental development in mouse and humans. Nat Rev Genet, 21, 27-43.

HUANG, R., GRISHAGIN, I., WANG, Y., ZHAO, T., GREENE, J., OBENAUER, J. C., NGAN, D., NGUYEN, D. T., GUHA, R., JADHAV, A., SOUTHALL, N., SIMEONOV, A. & AUSTIN, C. P. 2019. The NCATS BioPlanet—An Integrated Platform for Exploring the Universe of Cellular Signaling Pathways for Toxicology, Systems Biology, and Chemical Genomics. Front Pharmacol, 10, 445.

ING, N. H. & TORNESI, M. B. 1997. Estradiol up-regulates estrogen receptor and progesterone receptor gene expression in specific ovine uterine cells. Biol Reprod, 56, 1205-15.

JIN, S. 2019. Bipotent stem cells support the cyclical regeneration of endometrial epithelium of the murine uterus. Proc Natl Acad Sci USA, 116, 6848-6857.

KIN, K., NNAMANI, M. C., LYNCH, V. J., MICHAELIDES, E. & WAGNER, G. P. 2015. Cell-type phylogenetics and the origin of endometrial stromal cells. Cell Rep, 10, 1398-409.

KULESHOV, M. V., JONES, M. R., ROUILLARD, A. D., FERNANDEZ, N. F., DUAN, Q., WANG, Z., KOPLEV,

42

S., JENKINS, S. L., JAGODNIK, K. M., LACHMANN, A., MCDERMOTT, M. G., MONTEIRO, C. D., GUNDERSEN, G. W. & MA'AYAN, A. 2016. Enrichr: a comprehensive gene set enrichment analysis web server 2016 update. Nucleic Acids Res, 44, W90-7.

LACHMANN, A., XU, H., KRISHNAN, J., BERGER, S. I., MAZLOOM, A. R. & MA'AYAN, A. 2010. ChEA: transcription factor regulation inferred from integrating genome-wide ChIP-X experiments. Bioinformatics, 26, 2438-44.

LEE, K. Y., JEONG, J. W., WANG, J., MA, L., MARTIN, J. F., TSAI, S. Y., LYDON, J. P. & DEMAYO, F. J. 2007. Bmp2 is critical for the murine uterine decidual response. Mol Cell Biol, 27, 5468-78.

LEEK, J. T. 2014. svaseq: removing batch effects and other unwanted noise from sequencing data. Nucleic Acids Res, 42.

LI, Q., KANNAN, A., DAS, A., DEMAYO, F. J., HORNSBY, P. J., YOUNG, S. L., TAYLOR, R. N., BAGCHI, M. K. & BAGCHI, I. C. 2013. WNT4 acts downstream of BMP2 and functions via beta-catenin signaling pathway to regulate human endometrial stromal cell differentiation. Endocrinology, 154, 446-57.

LOVE, M. I., HUBER, W. & ANDERS, S. 2014. Moderated estimation of fold change and dispersion for RNA-seq data with DESeq2. Genome Biol, 15, 550.

MALE, V., GARDNER, L. & MOFFETT, A. 2012. Isolation of cells from the feto-maternal interface. Curr Protoc Immunol, Chapter 7, Unit 7 40 1-11.

MARINIC, M. & LYNCH, V. J. 2019. Derivation of endometrial gland organoids from term postpartum placenta. bioRxiv 753780.

MARINIC, M., RANA, S. & LYNCH, V. J. 2020. Derivation of endometrial gland organoids from term placenta. Placenta, 101, 75-79.

MASUDA, H., ANWAR, S. S., BUHRING, H. J., RAO, J. R. & GARGETT, C. E. 2012. A novel marker of human endometrial mesenchymal stem-like cells. Cell Transplant, 21, 2201-14.

MCLEAN, M., DAVIS, A. J. & REINDOLLAR, R. H. 2000. Abnormalities of Female Pubertal Development. In: FEINGOLD, K. R., ANAWALT, B., BOYCE, A., CHROUSOS, G., DUNGAN, K., GROSSMAN, A., HERSHMAN, J. M., KALTSAS, G., KOCH, C., KOPP, P., KORBONITS, M., MCLACHLAN, R., MORLEY, J. E., NEW, M., PERREAULT, L., PURNELL, J., REBAR, R., SINGER, F., TRENCE, D. L., VINIK, A. & WILSON, D. P. (eds.) Endotext. South Dartmouth (MA).

MIYAZAKI, K., DYSON, M. T., COON, V. J., FURUKAWA, Y., YILMAZ, B. D., MARUYAMA, T. & BULUN, S. E. 2018. Generation of Progesterone-Responsive Endometrial Stromal Fibroblasts from Human Induced Pluripotent Stem Cells: Role of the WNT/CTNNB1 Pathway. Stem Cell Reports, 11, 1136-1155.

MORIZANE, R., LAM, A. Q., FREEDMAN, B. S., KISHI, S., VALERIUS, M. T. & BONVENTRE, J. V. 2015. Nephron organoids derived from human pluripotent stem cells model kidney development and injury. Nat Biotechnol, 33, 1193-200.

MURUGANANDAN, S., FAN, X., DHAL, S. & NAYAK, N. R. 2020. Development of A 3D Tissue Slice Culture Model for the Study of Human Endometrial Repair and Regeneration. Biomolecules, 10.

NAWAZ, G. & ROGOL, A. D. 2020. Amenorrhea. StatPearls. Treasure Island (FL). PATRO, R., DUGGAL, G., LOVE, M. I., IRIZARRY, R. A. & KINGSFORD, C.

2017. Salmon provides fast and bias-aware quantification of transcript expression. Nat Methods, 14, 417-419.

SAATCIOGLU, H. D., KANO, M., HORN, H., ZHANG, L., SAMORE, W., NAGYKERY, N., MEINSOHN, M. C., HYUN, M., SULIMAN, R., POULO, J., HSU, J., SACHA, C., WANG, D., GAO, G., LAGE, K., OLIVA, E., MORRIS SABATINI, M. E., DONAHOE, P. K. & PEPIN, D. 2019. Single-cell sequencing of neonatal uterus reveals an Misr2+ endometrial progenitor indispensable for fertility. Elife, 8.

SAKABE, N., ANEAS, I., KNOBLAUCH, N., SOBREIRA, D. R., CLARK, N., PAZ, C., HORTH, C., ZIFFRA, R., KAUR, H., LIU, X., ANDERSON, R., MORRISON, J., CHEUNG, V. C., GROTEGUT, C., REDDY, T. E., JACOBSSON, B., HALLMAN, M., TERAMO, K., MURTHA, A., KESSLER, J., GROBMAN, W., ZHANG, G., MUGLIA, L. J., RANA, S., LYNCH, V. J., CRAWFORD, G. E., OBER, C., HE, X. & NÓBREGA, M. A. 2020. Transcriptome and regulatory maps of deciduaderived stromal cells inform gene discovery in preterm birth. bioRxiv, 2020.04.06.017079.

SCHURING, A. N., SCHULTE, N., KELSCH, R., ROPKE, A., KIESEL, L. & GOTTE, M. 2011. Characterization of endometrial mesenchymal stem-like cells obtained by endometrial biopsy during routine diagnostics. Fertil Steril, 95, 423-6.

SCHWAB, K. E. & GARGETT, C. E. 2007. Co-expression of two perivascular cell markers isolates mesenchymal stem-like cells from human endometrium. Hum Reprod, 22, 2903-11.

SCOTTI, S., REGIDOR, P. A., SCHINDLER, A. E. & WINTERHAGER, E. 2000. Reduced proliferation and cell adhesion in endometriosis. Mol Hum Reprod, 6, 610-7.

SU, R. W., STRUG, M. R., JEONG, J. W., MIELE, L. & FAZLEABAS, A. T. 2016. Aberrant activation of canonical Notch1 signaling in the mouse uterus decreases progesterone receptor by hypermethylation and leads to infertility. Proc Natl Acad Sci USA, 113, 2300-5.

SURYAWANSHI, H., MOROZOV, P., STRAUS, A., SAHASRABUDHE, N., MAX, K. E. A., GARZIA, A., KUSTAGI, M., TUSCHL, T. & WILLIAMS, Z. 2018. A single-cell survey of the human first trimester placenta and decidua. Sci Adv, 4, eaau4788.

TAKASATO, M., ER, P. X., BECROFT, M., VANSLAMBROUCK, J. M., STANLEY, E. G., ELEFANTY, A. G. & LITTLE, M. H. 2014. Directing human embryonic stem cell differentiation towards a renal lineage generates a self-organizing kidney. Nat Cell Biol, 16, 118-26.

TURCO, M. Y., GARDNER, L., HUGHES, J., CINDROVA-DAVIES, T., GOMEZ, M. J., FARRELL, L., HOLLINSHEAD, M., MARSH, S. G. E., BROSENS, J. J., CRITCHLEY, H. O., SIMONS, B. D., HEMBERGER, M., KOO, B. K., MOFFETT, A. & BURTON, G. J. 2017. Long-term, hormoneresponsive organoid cultures of human endometrium in a chemically defined medium. Nat Cell Biol, 19, 568-577.

VAN SINDEREN, M., CUMAN, C., GAMAGE, T., RAINCZUK, K., OSIANLIS, T., ROMBAUTS, L. & DIMITRIADIS, E. 2014. Localisation of the Notch family in the human endometrium of fertile and infertile women. J Mol Histol, 45, 697-706.

VASKIVUO, T. E., STENBACK, F., KARHUMAA, P., RISTELI, J., DUNKEL, L. & TAPANAINEN, J. S. 2000. Apoptosis and apoptosis-related proteins in human endometrium. Mol Cell Endocrinol, 165, 75-83.

VASQUEZ, Y. M., WANG, X., WETENDORF, M., FRANCO, H. L., MO, Q., WANG, T., LANZ, R. B., YOUNG, S. L., LESSEY, B. A., SPENCER, T. E., LYDON, J. P. & DEMAYO, F. J. 2018. FOXO1 regulates uterine epithelial integrity and progesterone receptor expression critical for embryo implantation. PLoS Genet, 14, e1007787.

VASSILEV, V., PRETTO, C. M., CORNET, P. B., DELVAUX, D., EECKHOUT, Y., COURTOY, P. J., MARBAIX, E. & HENRIET, P. 2005. Response of matrix metalloproteinases and tissue inhibitors of metalloproteinases messenger ribonucleic acids to ovarian steroids in human endometrial explants mimics their gene- and phase-specific differential control in vivo. J Clin Endocrinol Metab, 90, 5848-57.

VENTO-TORMO, R., EFREMOVA, M., BOTTING, R. A., TURCO, M. Y., VENTO-TORMO, M., MEYER, K. B., PARK, J. E., STEPHENSON, E., POLANSKI, K., GONCALVES, A., GARDNER, L., HOLMQVIST, S., HENRIKSSON, J., ZOU, A., SHARKEY, A. M., MILLAR, B., INNES, B., WOOD, L., WILBREY-CLARK, A., PAYNE, R. P., IVARSSON, M. A., LISGO, S., FILBY, A., ROWITCH, D. H., BULMER, J. N., WRIGHT, G. J., STUBBINGTON, M. J. T., HANIFFA, M., MOFFETT, A. & TEICHMANN, S. A. 2018. Single-cell reconstruction of the early maternal-fetal interface in humans. Nature, 563, 347-353.

WANG, W., VILELLA, F., MORENO, I., PAN, W., QUAKE, S. & SIMON, C. 2018. Single Cell Rnaseq Provides a Molecular and Cellular Cartography of Changes to the Human Endometrium through the Menstrual Cycle. Fertility and Sterility, 110, E2-E2.

WIWATPANIT, T., MURPHY, A. R., LU, Z., URBANEK, M., BURDETTE, J. E., WOODRUFF, T. K. & KIM, J. J. 2020. Scaffold-Free Endometrial Organoids Respond to Excess Androgens Associated With Polycystic Ovarian Syndrome. J Clin Endocrinol Metab, 105.

YIN, M., ZHOU, H. J., LIN, C., LONG, L., YANG, X., ZHANG, H., TAYLOR, H. & MIN, W. 2019. CD34(+) KLF4(+) Stromal Stem Cells Contribute to Endometrial Regeneration and Repair. Cell Rep, 27, 2709-2724 e3.

YUCER, N., HOLZAPFEL, M., JENKINS VOGEL, T., LENAEUS, L., ORNELAS, L., LAURY, A., SAREEN, D., BARRETT, R., KARLAN, B. Y. & SVENDSEN, C. N. 2017. Directed Differentiation of Human Induced Pluripotent Stem Cells into Fallopian Tube Epithelium. Sci Rep, 7, 10741.

ZONDERVAN, K. T., RAHMIOGLU, N., MORRIS, A. P., NYHOLT, D. R., MONTGOMERY, G. W., BECKER, C. M. & MISSMER, S. A. 2016. Beyond Endometriosis Genome-Wide Association Study: From Genomics to Phenomics to the Patient. Semin Reprod Med, 34, 242-54.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method comprising:
(a) culturing a monolayer of pluripotent stem cells (PSCs) with a single differentiation factor consisting of a first Wnt/β-catenin agonist, CHIR99021, for about 4 days;
(b) culturing the cells of (a) with a single differentiation factor consisting of a second Wnt/β-catenin agonist for about 4 day, wherein the second Wnt/β-catenin agonist consists of WNT7A;
(c) culturing the cells of (b) with Bone Morphogenetic Protein 2 (BMP-2) and β-estradiol for about 4 days;
wherein the cultured cells of (c) comprise a monolayer of PSC endometrial stromal fibroblasts (PSC-ESF) cells;
(d) combining:
(i) dissociated cells from endometrial epithelial organoids (EEO), and
(ii) dissociated PSC-ESF of (c);
(e) culturing the combined cells of (d) in a porous substrate comprising extracellular matrix components for at least 3 days, and
(f) during the culturing step of (e), forming, by cell self-assembly a three-dimensional human endometrial tissue comprising an outer layer of PSC-ESF and an inner layer of epithelial cells;
wherein CHIR99021 is provided in a range of about 1-20 μM, WNT7A is provided in a range of about 10-200 ng/ml, BMP-4 is provided in a range of about 1-20 ng/ml, and β-estradiol is provided in a range of about 1-20 nM; and
wherein the three-dimensional human endometrial tissue is responsive to cyclic hormone treatment.

2. The method of claim 1, wherein the EEO cells express EpCAM, FOXA2, Ki67 and PR.

3. The method of claim 1, wherein the porous substrate comprises a semi-solid culture medium or three dimensional (3D) porous biomaterial.

4. The method of claim 1, wherein the outer layer of PSC-ESF cells interface with the inner layer of epithelial cells along the Laminin+basolateral surface of the epithelial cells.

5. The method of claim 1, wherein the cells from endometrial epithelial organoids (EEO), the PSC-ESFs or both comprise a genetic mutation known to cause a medical disease or condition when the genetic mutation is present in a human subject.

6. The method of claim 1, wherein CHIR99021 is provided at about 8 μM, WNT7A is provided at about 100 ng/ml, BMP-4 is provided at about 10 ng/ml, and β-estradiol is provided at about 10 nM.

* * * * *